US012637726B2

(12) United States Patent
Yang et al.

(10) Patent No.: US 12,637,726 B2
(45) Date of Patent: May 26, 2026

(54) SPIKE-IN REFERENCE STANDARD FOR USE IN DETECTING SAMPLE TARGET FROM DNA OR RNA ORGANISM

(71) Applicants: GUANGZHOU FULEN GENE CO., LTD., Guangzhou (CN); GUANGZHOU IGENE BIOTECHNOLOGY CO., LTD., Guangzhou (CN); GENE COPOEIA, INC., Rockville, MD (US)

(72) Inventors: Shuwei Yang, Rockville, MD (US); Liancheng Huang, Guangzhou (CN); Feifei Feng, Guangzhou (CN); Longwen Su, Guangzhou (CN); Kun Lin, Guangzhou (CN); Can Tang, Guangzhou (CN); Chen Liang, Guangzhou (CN); Yuanmei Wang, Guangzhou (CN); Yanqing Cai, Guangzhou (CN); Yilin Pang, Guangzhou (CN); Chuan Shen, Guangzhou (CN); Zhixue Yu, Guangzhou (CN)

(73) Assignees: GUANGZHOU FULEN GENE CO., LTD., Guangdong (CN); GUANGZHOU IGENE BIOTECHNOLOGY CO., LTD., Guangdong (CN); GENE COPOEIA, INC., Rockville, MD (US)

( * ) Notice: Subject to any disclaimer, the term of this patent is extended or adjusted under 35 U.S.C. 154(b) by 899 days.

(21) Appl. No.: 17/998,467

(22) PCT Filed: Mar. 10, 2021

(86) PCT No.: PCT/CN2021/080053
§ 371 (c)(1),
(2) Date: Nov. 10, 2022

(87) PCT Pub. No.: WO2021/180139
PCT Pub. Date: Sep. 16, 2021

(65) Prior Publication Data
US 2024/0117451 A1 Apr. 11, 2024

(30) Foreign Application Priority Data

Mar. 10, 2020 (CN) .......................... 202010160538.4

(51) Int. Cl.
| | |
|---|---|
| *C12N 15/86* | (2006.01) |
| *C07K 16/28* | (2006.01) |
| *C12N 7/00* | (2006.01) |
| *C12N 15/11* | (2006.01) |
| *C12N 15/861* | (2006.01) |
| *C12Q 1/6851* | (2018.01) |
| *C12Q 1/6876* | (2018.01) |
| *C12Q 1/70* | (2006.01) |
| *C12Q 1/6806* | (2018.01) |

(52) U.S. Cl.
CPC .............. *C12Q 1/701* (2013.01); *C12N 7/00* (2013.01); *C12N 15/86* (2013.01); *C12Q 1/6851* (2013.01); *C12N 2740/15022* (2013.01); *C12N 2740/15043* (2013.01); *C12N 2740/15052* (2013.01); *C12Q 1/6806* (2013.01); *C12Q 2600/166* (2013.01)

(58) Field of Classification Search
CPC .................. C12N 15/86; C12N 15/861; C12N 2740/15043; C12N 2740/16043; C12Q 2600/158
See application file for complete search history.

(56) References Cited

FOREIGN PATENT DOCUMENTS

| | | |
|---|---|---|
| CN | 102199674 A | 9/2011 |
| CN | 103484565 A | 1/2014 |
| CN | 104845993 A | 8/2015 |
| CN | 107557374 A | 1/2018 |
| CN | 110698546 A | 1/2020 |
| CN | 110819707 A | 2/2020 |
| WO | 2006031608 A2 | 3/2006 |

OTHER PUBLICATIONS

International Search Report for PCT/CN2021/080053 dated Jun. 9, 2021 (with English translation). 8 pages.
Written Opinion for PCT/CN2021/080053 dated Jun. 9, 2021 (with English translation). 15 pages.
Beld et al., Highly sensitive assay for detection of enterovirus in clinical specimens by reverse transcription-PCR with an armored RNA internal control, J Clin Microbiol, 2004, 42(7):3059-3064.
Cheng et al., Preparation of His-tagged armored RNA phage particles as a control for real-time reverse transcription-PCR detection of severe acute respiratory syndrome coronavirus, J Clin Microbiol, 2006, 44(10):3557-3561.
Clancy et al., The development of a qualitative real-time RT-PCR assay for the detection of hepatitis C virus, Eur J Clin Microbiol Infect Dis, 2008, 27(12):1177-1182.
Cleland et al., Use of bovine viral diarrhea virus as an internal control for amplification of hepatitis C virus, Vox Sang, 1999, 76(3):170-174.
Dingle et al., Stable and noncompetitive RNA internal control for routine clinical diagnostic reverse transcription-PCR, J Clin Microbiol, 2004, 42(3):1003-1011.

(Continued)

*Primary Examiner* — Barry A Chestnut

(74) *Attorney, Agent, or Firm* — Medler Ferro Woodhouse & Mills PLLC

(57) ABSTRACT

Positive reference spiked in collected sample for use in qualitatively and quantitatively detecting viral RNA.

20 Claims, 22 Drawing Sheets
Specification includes a Sequence Listing.

(56)        References Cited

OTHER PUBLICATIONS

Dreier et al., Use of Bacteriophage MS2 as an Internal Control in Viral Reverse Transcription-PCR Assays, J Clin Microbiol., 2005, 43(9):4551-4557.

Drosten et al., TaqMan 5'-nuclease human immunodeficiency virus type 1 PCR assay with phage-packaged competitive international control for High-Throughput Blood Donor Screening, J Clin Microbiol, 2001, 39(12): 4302-4308.

Felder et al., Development of a versatile and stable internal control system for RT-qPCR assays, J Virol Methods,. 2014, 208:33-40.

Garson et al., Real-time PCR quantitation of hepatitis B virus DNA using automated sample preparation and murine cytomegalovirus internal control, J Virol Methods, 2005, 126(1-2):207-213.

Gerriets et al., Implementation of a T4 extraction control for molecular assays of cerebrospinal fluid and stool specimens, J Mol Diagn, 2008, 10(1):28-32.

Gibson et al., A Novel Method for Real Time Quantitative RT-PCR, Genome Res, 1996, 6(10):995-1001.

Hoorfar et al., Practical considerations in design of internal amplification controls for diagnostic PCR assays, J Clin Microbiol, 2004, 42(5):1863-1868.

Hymas et al., Use of lyophilized standards for the calibration of a newly developed real time PCR assay for human herpes type six (HHV6) variants A and B, J Virol Methods, 2005, 128(1-2):143-150.

Kim et al., Viral Load Kinetics of SARS-CoV-2 Infection in First Two Patients in Korea, J Korean Med Sci, 2020, 35(7): e86.

Maaroufi et al., Development of a multiple internal control for clinical diagnostic real-time amplification assays, FEMS Immunol Med Microbiol, 2006, 48(2):183-191.

Meng et al., Nuclease-resistant double-stranded DNA controls or standards for hepatitis B virus nucleic acid amplification assays, Virol J, 2009, 6:226.

Ninove et al., RNA and DNA bacteriophages as molecular diagnosis controls in clinical virologyú II a comprehensive study of more than 45,000 routine PCR tests, PLoS One, 2011, 6(2):e16142.

Pan et al., Viral load of SARS-CoV-2 in clinical samples, Lancet Infect Dis, 2020, 20(4):411-412.

Pasloske et al., Armored RNA technology for production of ribonuclease-resistant viral RNA controls and standards, J Clin Microbiol, 1998, 36(12):3590-3594.

Rolfe et al., An internally controlled, one-step, real-time RT-PCR assay for norovirus detection and genogrouping, J Clin Virol, 2007, 39(4):318-321.

Rosenstraus et al., An internal control for routine diagnostic PCR: design, properties, and effect on clinical performance, J Clin Microbiol, 1998, 36(1):191-197.

Sharma, Internal controls for the quality assessment of polymerase chain reaction methods for the diagnosis of infectious & autoimmune disease, Sch J App Med Sci, 2014, 2(1D):485-488.

Stocher et al., Internal control DNA for PCR assays introduced into lambda phage particles exhibits nuclease resistance, Clin Chem, 2004, 50(11):2163-2166.

Stocher et al., A convenient approach to the generation of multiple internal control DNA for a panel of real-time PCR assays, J Virol Methods, 2003, 108(1):1-8.

Villanova et al., Strategic approach to produce low-cost, efficient, and stable competitive internal controls for detection of RNA viruses by use of reverse transcription-PCR, J Clin Microbiol, 2007, 45(11):3555-3563.

WalkerPeach et al., Ribonuclease-resistant RNA controls (Armored RNA) for reverse transcription-PCR, branched DNA, and genotyping assays for hepatitis C virus, Clin Chem, 1999, 45(12):2079-2085.

Wei et al., RNase-resistant virus-like particles containing long chimeric RNA sequences produced by two-plasmid coexpression system, J Clin Microbiol, 2008, 46(5):1734-1740.

Zambenedetti et al., Inernal control for real-time polymerase chain reaction based on MS2 bacteriophage for RNA viruses diagnostics, Mem Inst Oswaldo Cruz, 2017, 112(5): 339-347.

Zhan et al., Armored long RNA controls or standards for branched DNA assay for detection of human immunodeficiency virus type 1, J Clin Microbiol, 2009, 47(8): 2571-2576.

Zhao et al., Armored RNA as positive control and standard for quantitative reverse transcription-polymerase chain reaction assay for rubella virus, Arch Virol, 2007, 152(1):219-224.

Zou et al., SARS-CoV-2 Viral Load in Upper Respiratory Specimens of Infected Patients, N Engl J Med,. 2020, 382(12):1177-1179.

| No. | product name | registrant | registered number |
|---|---|---|---|
| 1 | 2019-nCoV nucleic acid detection kit (fluorescent PCR method) | Shanghai ZJ Bio-Tech Co., Ltd. | National Machinery Registration(standard) No. 20203400057 |
| 2 | 2019-nCoV nucleic acid detection kit (fluorescent PCR method) | Shanghai GenoDx Biotech Co.,Ltd | National Machinery Registration(standard) No. 20203400058 |
| 3 | 2019-nCoV nucleic acid detection kit (combined with probe-anchored polymerization sequencing method) | Huada Biotech (wuhan) Co., Ltd. | National Machinery Registration(standard) No. 20203400059 |
| 4 | 2019-nCoV nucleic acid detection kit (fluorescent PCR method) | Huada Biotech (wuhan) Co., Ltd. | National Machinery Registration(standard) No. 20203400060 |
| 5 | 2019-nCoV nucleic acid detection kit (fluorescent PCR method) | Daan Gene Co., Ltd. | National Machinery Registration(standard) No. 20203400063 |
| 6 | 2019-nCoV nucleic acid detection kit (fluorescent PCR method) | Sansure Biotech Inc. | National Machinery Registration(standard) No. 20203400064 |
| 7 | 2019-nCoV nucleic acid detection kit (fluorescent PCR method) | Shanghai Biogerm Medical Technology Co., Ltd. | National Machinery Registration(standard) No. 20203400065 |
| 8 | 2019-nCoV nucleic acid detection kit (colloidal gold method) | Guangzhou Wondfo Biotech Co., Ltd. | National Machinery Registration(standard) No. 20203400176 |
| 9 | 2019-nCoV nucleic acid detection kit (colloidal gold method) | INNOVITA (Tangshan) BIOLOGICAL TECHNOLOGY CO., LTD | National Machinery Registration(standard) No. 20203400177 |
| 10 | Six-respiratory viruses nucleic acid detection kits (isothermal amplification chip method) | Chengdu capitalbio Biotech Co., Ltd. | National Machinery Registration(standard) No. 20203400178 |
| 11 | 2019-nCoV nucleic acid detection kit (fluorescent PCR method) | Beijing Applied Biological Technologies Co. Ltd. | National Machinery Registration(standard) No. 20203400179 |
| 12 | 2019-nCoV IgM antibody detection kit (magnetic particle chemiluminescence method) | Bioscience (Chongqing) Biotech Co., Ltd. | National Machinery Registration(standard) No. 20203400182 |
| 13 | 2019-nCoV IgG antibody detection kit (magnetic particle chemiluminescence method) | Bioscience (Chongqing) Biotech Co., Ltd. | National Machinery Registration(standard) No. 20203400183 |
| 14 | 2019-nCoV nucleic acid detection kit (fluorescent PCR method) | Maccura Biotechnology Co., Ltd. | National Machinery Registration(standard) No. 20203400184 |
| 15 | 2019-nCoV antibody detection kit (chemiluminescence microparticle immunoassay) | Xiamen Innodx Biotechnology Co., Ltd. | National Machinery Registration(standard) No. 20203400198 |

Fig. 1

```
G119753              CCAGTTTATCTAATACGACTCACTATAGGGAGAGAGAGAGAGAATTACCCTC 50
orf1ab-TargetSequence ------------------------------------------------CCCTC 5
                                                                     *****

G119753              ACTAAAGGGAGGAGAAGCATGTCGACGAATTCCTAATACGACTCACTATA 100
orf1ab-TargetSequence ACTAAAGGGAGGAGAAGCATGTCGACGAATTCCTAATACGACTCACTATA 55
                     **************************************************

G119753              GGATATCGTTGTCTGTACTGCCGTTGCCACATAGATCATCCAAATCCTAA 150
orf1ab-TargetSequence GGATATCGTTGTCTGTACTGCCGTTGCCACATAGATCATCCAAATCCTAA 105
                     **************************************************

G119753              AGGATTTTGTGACTTAAAAGGTAAGTATGTACAAATACCTACAACTTGTG 200
orf1ab-TargetSequence AGGATTTTGTGACTTAAAAGGTAAGTATGTACAAATACCTACAACTTGTG 155
                     **************************************************

G119753              CTAATGACCCTGTGGGTTTTACACTTAAAATGCAGTTCCGAGCTCACTCG 250
orf1ab-TargetSequence CTAATGACCCTGTGGGTTTTACACTTAAAATGCAGTTCCGAGCTCACTCG 205
                     **************************************************

G119753              ACTCTCTGATCAGACGATGGTTTTACTTATCACCAAATCCGCGTAGGCAG 300
orf1ab-TargetSequence ACTCTCTGATCAGACGATGGTTTTACTTATCACCAAATCCGCGTAGGCAG 255
                     **************************************************

G119753              ATCGTAGTCAGCTGATGCACAATCGTTTTTAAACGGGTTTGCGGTGTAAG 350
orf1ab-TargetSequence ATCGTAGTCAGCTGATGCACAATCGTTTTTAAACGGGTTTGCGGTGTAAG 305
                     **************************************************

G119753              TGCAGCCCGTCTTACACCGTGCGGCACAGGCACTCGAGCTGTGGAATGTG 400
orf1ab-TargetSequence TGCAGCCCGTCTTACACCGTGCGGCACAGGCACTCGAGCTGTGGAATGTG 355
                     **************************************************

G119753              TGTCAGTTAGGGTGTGGAAAGTCCCCAGGCTCCCCA 436
orf1ab-TargetSequence TGTCAGT----------------------------- 362
                     ******
```

Fig. 5

Methods for designing positive standards for all species of known
DNA or RNA sequences that can be spiked into the test sample
or sample collection device (tube)

a                                   b
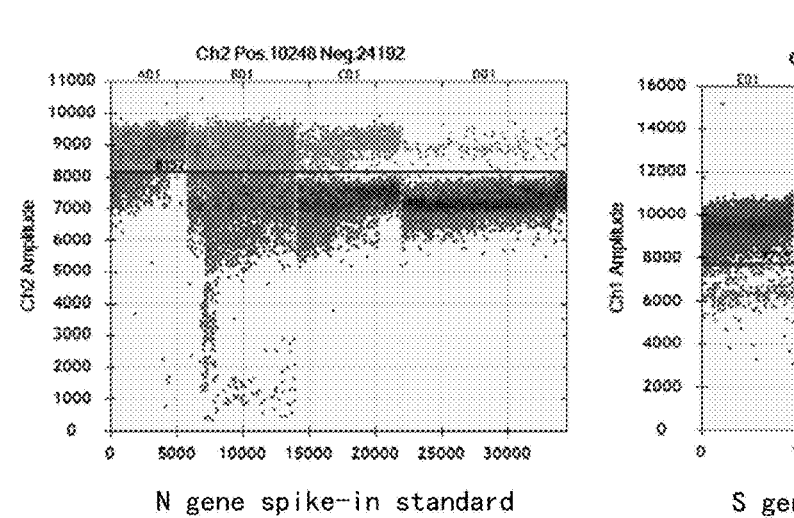
N gene spike-in standard
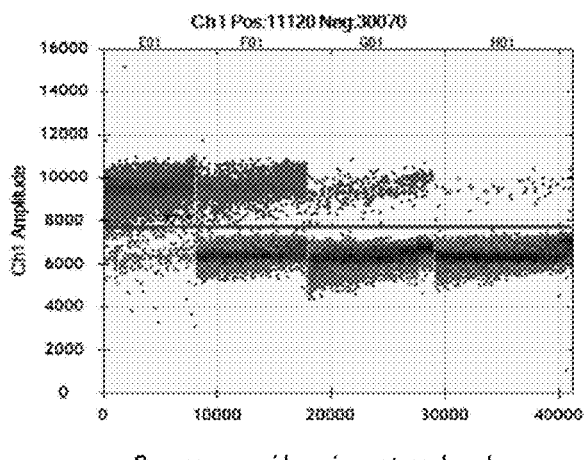
S gene spike-in standard
c
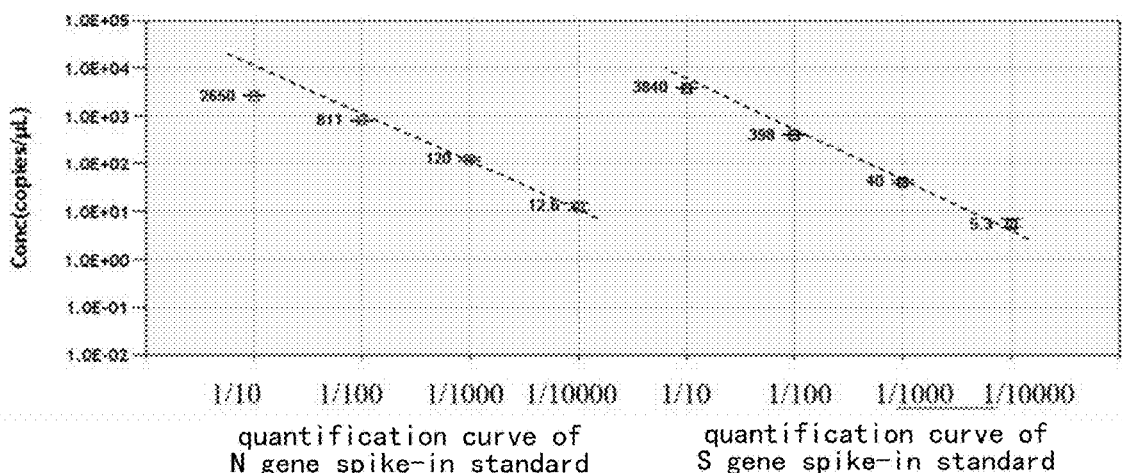
quantification curve of
N gene spike-in standard        quantification curve of
S gene spike-in standard
Fig. 26 a

A method for designing positive standards for all species of
known DNA or RNA sequences that can be spiked into the test
sample or sample collection device (tube)

b
A method for designing positive standards for all species of
known DNA or RNA sequences that can be spiked into the test
sample or sample collection device (tube)
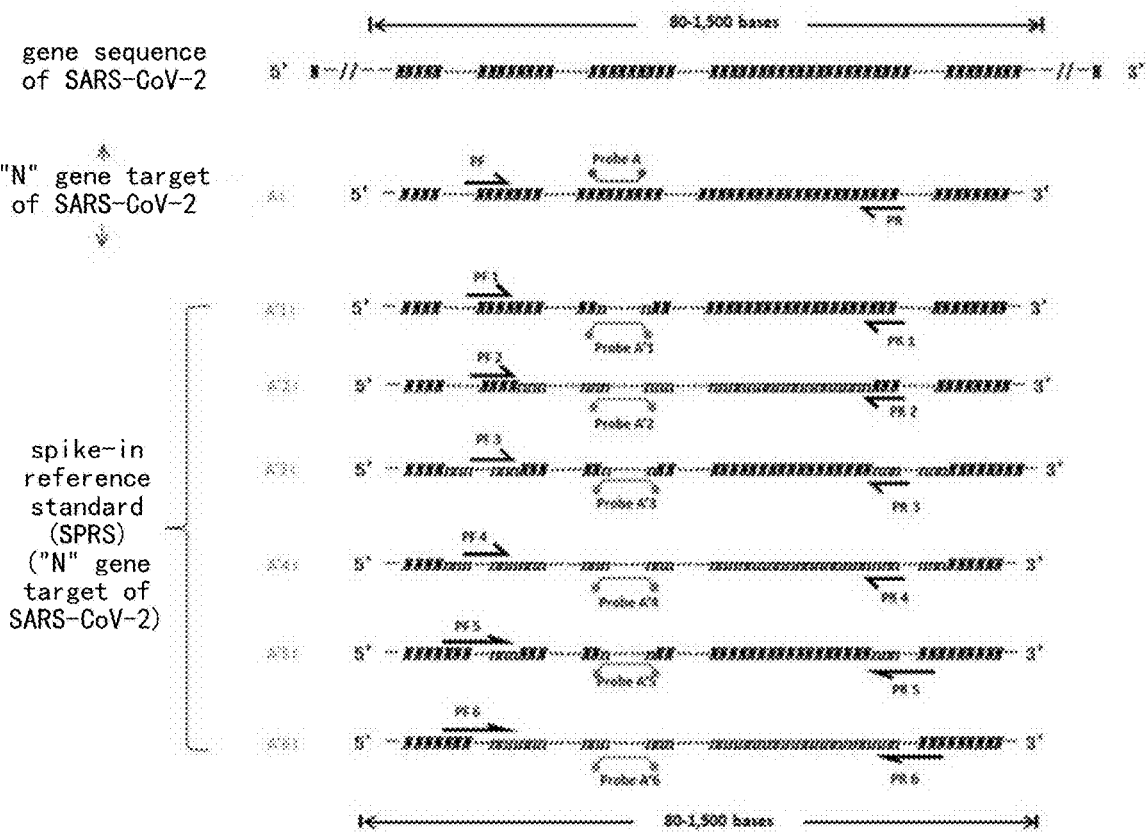
Fig. 28(continue)

c
A method for designing positive standards for all species of
known DNA or RNA sequences that can be spiked into the test
sample or sample collection device (tube)
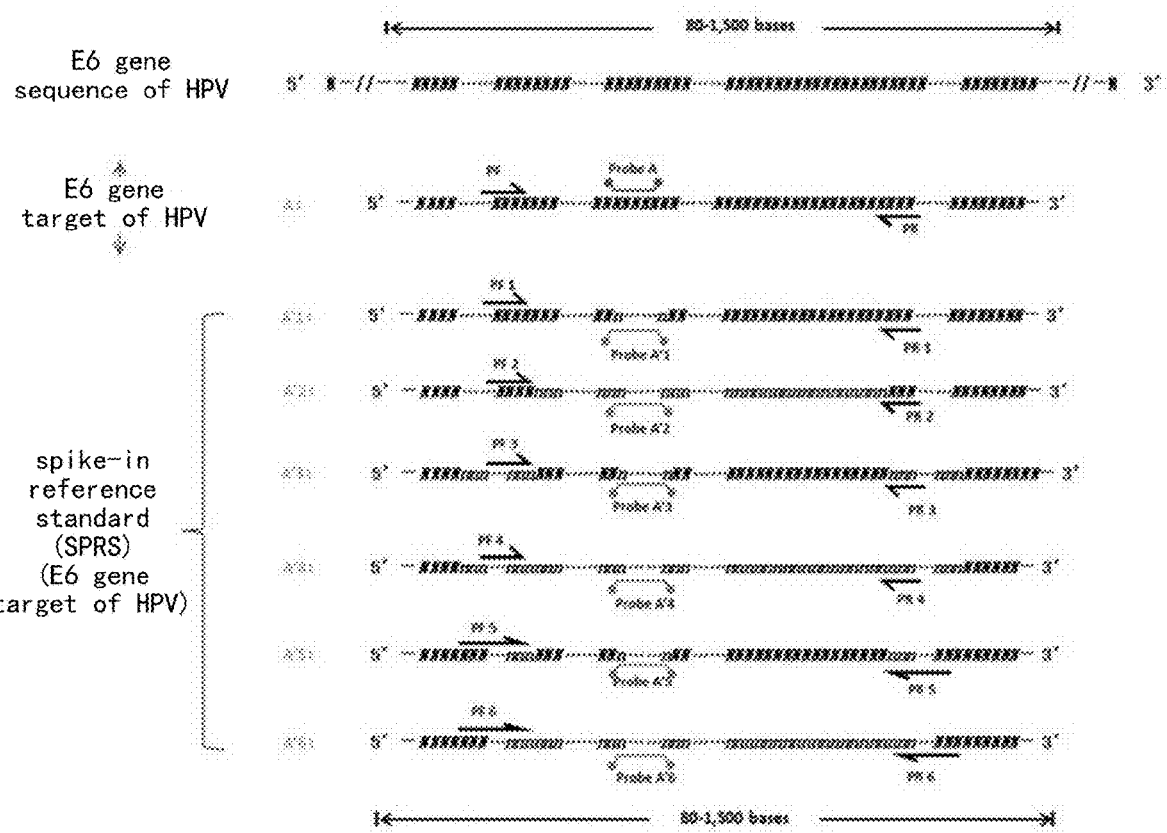
Fig. 28 (continue)

d
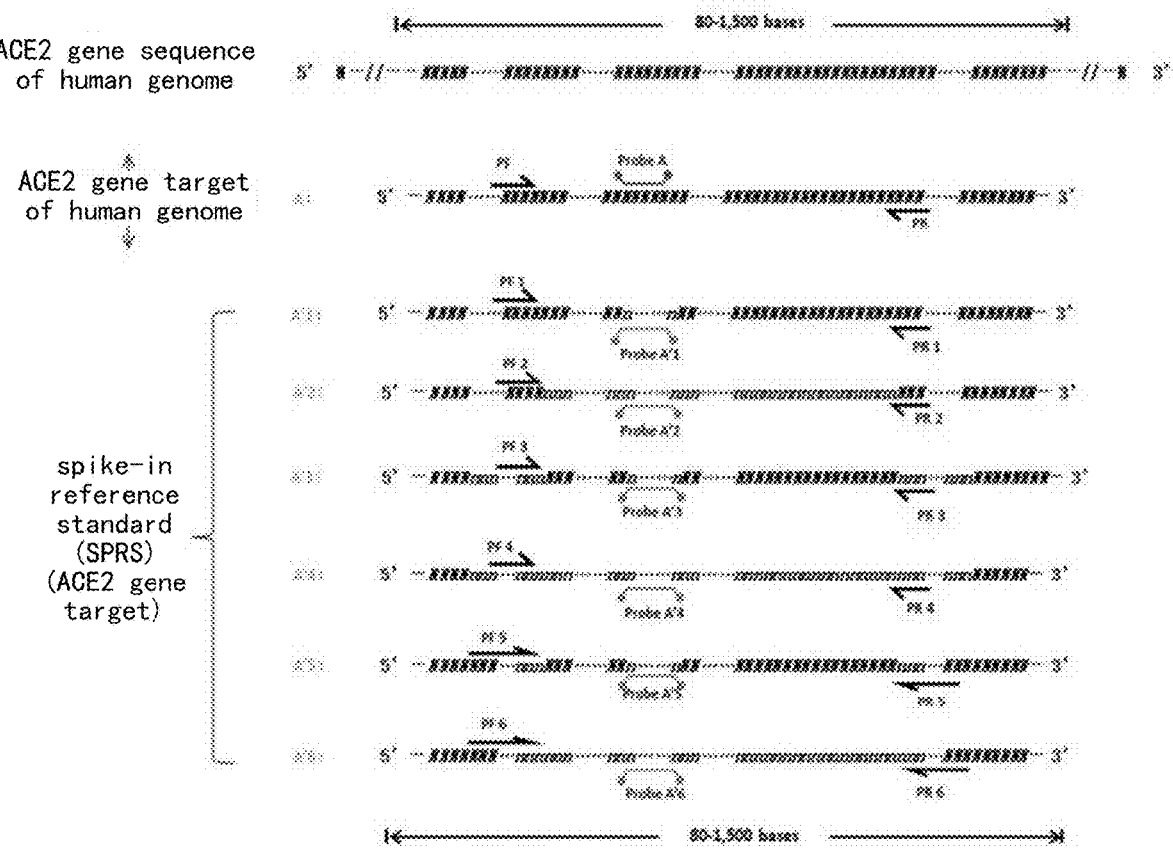
A method for designing positive standards for all species of
known DNA or RNA sequences that can be spiked into the test
sample or sample collection device (tube)
Fig. 28 (continue)

SEQUENCE LISTING

<160> NUMBER OF SEQ ID NOS: 89

<210> SEQ ID NO 1
<211> LENGTH: 275
<212> TYPE: DNA
<213> ORGANISM: Artificial Sequence
<220> FEATURE:
<223> OTHER INFORMATION: Synthesized

<400> SEQUENCE: 1
gttgtctgta ctgccgttgc cacatagatc atccaaatcc taaaggattt tgtgacttaa       60
aaggtaagta tgtacaaata cctacaactt gtgctaatga ccctgtgggt tttacactta      120
aaatgcagtt ccgagctcac tcgactctct gatcagacga tggtttttact tatcaccaaa      180 tccgcgtagg cagatcgtag tcagctgatg cacaatcgtt tttaaacggg tttgcggtgt      240
aagtgcagcc cgtcttacac cgtgcggcac aggca                                 275

<210> SEQ ID NO 2
<211> LENGTH: 300
<212> TYPE: DNA
<213> ORGANISM: Artificial Sequence
<220> FEATURE:
<223> OTHER INFORMATION: Synthesized

<400> SEQUENCE: 2
agaattatgg cctcacttgt tcttgctcgc aaacatacaa cgtgttgtag cttgtcacac       60
cgtttctata gattagctaa tgagtgtgct caagtattga gtgaaatggt catgtgtggc      120
ggttgcacat atagacaaac ggctacaggc tcaccacgta agaccataac gacttatgct      180

-continued

```
aatagtgttt ttaacatttg tcaagctgtc acggccaatg ttaatgcact tttatctact        240
gatggtaaca aaattgccga taagtatgtc cgcaatttac aacacagact ttatgagtgt        300
```

<210> SEQ ID NO 3
<211> LENGTH: 338
<212> TYPE: DNA
<213> ORGANISM: Artificial Sequence
<220> FEATURE:
<223> OTHER INFORMATION: Synthesized

<400> SEQUENCE: 3

```
acaagacaaa aacacccaag aagtttttgc acaagtcaaa caaatttaca aaacaccacc         60
aattaaagat tttggtggtt ttaattttc acaaatatta ccagatccat caaaaccaag        120
caatcacgat atgattatga ctactctcac tatcaaagcc tcaaccgctg aacagtgcct        180
agacattgaa ctattctact gtcttgctag cttatctgct agagacctca tttgtgcaca        240
aaagtttaac ggccttactg ttttgccacc tttgctcaca gatgaaatga ttgctcaata        300
cacttctgca ctgttagcgg gtacaatcac ttctggtt                                338
```

<210> SEQ ID NO 4
<211> LENGTH: 313
<212> TYPE: DNA
<213> ORGANISM: Artificial Sequence
<220> FEATURE:
<223> OTHER INFORMATION: Synthesized

<400> SEQUENCE: 4

```
aatggaacca atttatgatg aaccgacgac gactactagc gtgcctttgt aagcacaagc         60
tgatgagtac gaacttatgt actcattcgt ttcggaagag acaggtacgt taatagttaa        120
tagcgtacca tatgagatca tgaatcttga tcgttagtca cttcctcagc gaagactaat        180
ggcgagatga ttgtgtgcgt actgctgcaa tattgttaac gtgagtcttg taaaaccttc        240
tttttacgtt tactctcgtg ttaaaaatct gaattcttct agagttcctg atcttctggt        300
ctaaacgaac taa                                                           313
```

<210> SEQ ID NO 5
<211> LENGTH: 299
<212> TYPE: DNA
<213> ORGANISM: Artificial Sequence
<220> FEATURE:
<223> OTHER INFORMATION: Synthesized

<400> SEQUENCE: 5

```
ggcttctacg cagaagggag cagaggcggc agtcaagcct cttctcgttc ctcatcacgt         60
agtcgcaaca gttcaagaaa ttcaactcca ggcagcagta ggggaacttc tcctgctaga        120
atggacccgg acaccgagga tgcacagctc gctctatcta gtcctgatac acatcaccag        180
cttgagagca aaatgtctgg taaaggccaa caacaacaag gccaaactgt cactaagaaa        240
tctgctgctg aggcttctaa gaagcctcgg caaaaacgta ctgccactaa agcatacaa        299
```

<210> SEQ ID NO 6
<211> LENGTH: 272
<212> TYPE: DNA
<213> ORGANISM: Artificial Sequence
<220> FEATURE:
<223> OTHER INFORMATION: Synthesized

<400> SEQUENCE: 6

```
tgtagtgcgt tgttcgttct atgaagactt tttagagtat catgacgttc gtgttgtttt         60
```

-continued

```
agatttcatc taaacgaaca aactaaaatg tctgataatg acccccaaaa tcagcgaaat      120
gcacgccagc ttacgacatg cgaatcctca gattcaactg gcagtaacca gaatggagaa      180
cgcagtgggg cgcgatcaaa acaacgtcgg ccccaaggtt tacccaataa tactgcgtct      240
tggttcaccg ctctcactca acatggcaag ga                                    272

<210> SEQ ID NO 7
<211> LENGTH: 267
<212> TYPE: DNA
<213> ORGANISM: Artificial Sequence
<220> FEATURE:
<223> OTHER INFORMATION: Synthesized

<400> SEQUENCE: 7
ccactaaagc atacaatgta acacaagctt tcggcagacg tggtccagaa caaacccaag       60
gaaattttgg ggaccaggaa ctaatcagac aaggaactga ttacaaacat tggccgcaaa      120
ttagcacatc cgcacgccac tcgtaaccgt tcttcggaat gtcgcgcatt ggcatggaag      180
tcacaccttc gggaacgtgg ttgacctaca caggtgccat caaattggat gacaaagatc      240
caaatttcaa agatcaagtc attttgc                                          267

<210> SEQ ID NO 8
<211> LENGTH: 272
<212> TYPE: DNA
<213> ORGANISM: Artificial Sequence
<220> FEATURE:
<223> OTHER INFORMATION: Synthesized

<400> SEQUENCE: 8
atctcagtcc aagatggtat ttctactacc taggaactgg gccagaagct ggacttccct       60
atggtgctaa caaagacggc atcatatggg ttgcaactga gggagccttg aatacaccaa      120
aagatcacgc atgcacactc cagcaccaga acaatgctgc aatcgtgcta caacttcctc      180
aaggaacaac attgccaaaa ggcttctacg cagaagggag cagaggcggc agtcaagcct      240
cttctcgttc ctcatcacgt agtcgcaaca gt                                    272

<210> SEQ ID NO 9
<211> LENGTH: 8275
<212> TYPE: DNA
<213> ORGANISM: Artificial Sequence
<220> FEATURE:
<223> OTHER INFORMATION: Synthesized

<400> SEQUENCE: 9
tcgccaccat ggtgagcaag ggcgaggagc tgttcaccgg ggtggtgccc atcctggtcg       60
agctggacgg cgacgtaaac ggccacaagt tcagcgtgtc cggcgagggc gagggcgatg      120
ccacctacgg caagctgacc ctgaagttca tctgcaccac cggcaagctg cccgtgccct      180
ggcccaccct cgtgaccacc ctgacctacg gcgtgcagtg cttcagccgc taccccgacc      240
acatgaagca gcacgacttc ttcaagtccg ccatgcccga aggctacgtc caggagcgca      300
ccatcttctt caaggacgac ggcaactaca gacccgcgc cgaggtgaag ttcgagggcg       360
acaccctggt gaaccgcatc gagctgaagg gcatcgactt caaggaggac ggcaacatcc      420
tggggcacaa gctggagtac aactacaaca gccacaacgt ctatatcatg gccgacaagc      480
agaagaacgg catcaaggtg aacttcaaga tccgccacaa catcgaggac ggcagcgtgc      540
agctcgccga ccactaccag cagaacaccc ccatcggcga cggccccgtg ctgctgcccg      600
```

-continued

```
acaaccacta cctgagcacc cagtccgccc tgagcaaaga ccccaacgag aagcgcgatc    660
acatggtcct gctggagttc gtgaccgccg ccgggatcac tctcggcatg gacgagctgt    720
acaagtaaag cggccgcgat cccgcccctc tccctccccc cccctaacg ttactggccg      780 aagccgcttg gaataaggcc ggtgtgcgtt tgtctatatg ttattttcca ccatattgcc    840
gtcttttggc aatgtgaggg cccggaaacc tggccctgtc ttcttgacga gcattcctag    900
gggtctttcc cctctcgcca aaggaatgca aggtctgttg aatgtcgtga aggaagcagt    960
tcctctggaa gcttcttgaa gacaaacaac gtctgtagcg acccttttgca ggcagcggaa   1020 ccccccacct ggcgacaggt gcctctgcgg ccaaaagcca cgtgtataag atacacctgc   1080
aaaggcggca caaccccagt gccacgttgt gagttggata gttgtggaaa gagtcaaatg   1140
gctctcctca agcgtattca acaaggggct gaaggatgcc cagaaggtac cccattgtat   1200
gggatctgat ctggggcctc ggtgcacatg ctttacatgt gtttagtcga ggttaaaaaa   1260
acgtctaggc cccccgaacc acggggacgt ggttttcctt tgaaaaacac gatgataagc   1320
ttgccacaac ccacaaggag acgaccttcc atgaccgagt acaagcccac ggtgcgcctc   1380
gccacccgcg acgacgtccc cgggccgta cgcaccctcg ccgccgcgtt cgccgactac   1440
cccgccacgc gccacaccgt cgacccggac cgccacatcg agcgggtcac cgagctgcaa   1500
gaactcttcc tcacgcgcgt cgggctcgac atcggcaagg tgtgggtcgc ggacgacggc   1560
gccgcggtgg cggtctggac cacgccggag agcgtcgaag cggggcggt gttcgccgag   1620 atcggcccgc gcatggccga gttgagcggt tcccggctgg ccgcgcagca acagatggaa   1680
ggcctcctgg cgccgcaccg gcccaaggag cccgcgtggt tcctggccac cgtcggcgtc   1740
tcgcccgacc accagggcaa gggtctgggc agcgccgtcg tgctccccgg agtggaggcg   1800
gccgagcgcg ccggggtgcc cgccttcctg gagacctccg cgccccgcaa cctcccctc    1860 tacgagcggc tcggcttcac cgtcaccgcc gacgtcgagg tgcccgaagg accgcgcacc   1920
tggtgcatga cccgcaagcc cggtgcctag acgcgtctgg aacaatcaac ctctggatta   1980
caaaatttgt gaaagattga ctggtattct taactatgtt gctccttta cgctatgtgg     2040 atacgctgct ttaatgcctt tgtatcatgc tattgcttcc cgtatggctt tcattttctc   2100
ctccttgtat aaatcctggt tgctgtctct ttatgaggag ttgtggcccg ttgtcaggca   2160
acgtggcgtg gtgtgcactg tgtttgctga cgcaaccccc actggttggg gcattgccac   2220
cacctgtcag ctcctttccg ggactttcgc tttccccctc cctattgcca cggcggaact   2280
catcgccgcc tgccttgccc gctgctggac aggggctcgg ctgttgggca ctgacaattc   2340
cgtggtgttg tcggggaagc tgacgtcctt tccatggctg ctcgcctgtg ttgccacctg   2400
gattctgcgc gggacgtcct tctgctacgt cccttcggcc ctcaatccag cggaccttcc   2460
ttcccgcggc ctgctgccgg ctctgcggcc tcttccgcgt cttcgccttc gccctcagac   2520
gagtcggatc tccctttggg ccgcctcccc gcctggaatt aattctgcag tcgagaccta   2580
gaaaaacatg gagcaatcac aagtagcaat acagcagcta ccaatgctga ttgtgcctgg   2640
ctagaagcac aagaggagga ggaggtgggt ttttccagtc acacctcagg acctttaaga   2700
ccaatgactt acaaggcagc tgtagatctt agccactttt taaaagaaaa gagggggactg   2760 gaagggctaa ttcactccca acgaagacaa gatctgcttt ttgcctgtac tgggtctctc   2820
tggttagacc agatctgagc ctgggagctc tctggctaac tagggaaccc actgcttaag   2880
cctcaataaa gcttgccttg agtgcttcaa gtagtgtgtg cccgtctgtt gtgtgactct   2940
ggtaactaga gatccctcag acccttttag tcagtgtgga aaatctctag cagtagtagt   3000
```

```
tcatgtcatc ttattattca gtatttataa cttgcaaaga aatgaatatc agagagtgag   3060
aggctagcgt tttaccgtcg acctctagct agagcttggc gtaatcatgg tcatagctgt   3120
ttcctgtgtg aaattgttat ccgctcacaa ttccacacaa catacgagcc ggaagcataa   3180
agtgtaaagc ctggggtgcc taatgagtga gctaactcac attaattgcg ttgcgctcac   3240
tgcccgcttt ccagtcggga aacctgtcgt gccagctgca ttaatgaatc ggccaacgcg   3300
cggggagagg cggtttgcgt attgggcgct cttccgcttc ctcgctcact gactcgctgc   3360
gctcggtcgt tcggctgcgg cgagcggtat cagctcactc aaaggcggta atacggttat   3420
ccacagaatc aggggataac gcaggaaaga acatgtgagc aaaaggccag caaaaggcca   3480
ggaaccgtaa aaaggccgcg ttgctggcgt ttttccatag gctccgcccc cctgacgagc   3540
atcacaaaaa tcgacgctca agtcagaggt ggcgaaaccc gacaggacta taaagatacc   3600
aggcgtttcc ccctggaagc tccctcgtgc gctctcctgt tccgaccctg ccgcttaccg   3660
gatacctgtc cgcctttctc ccttcgggaa gcgtggcgct ttctcatagc tcacgctgta   3720
ggtatctcag ttcggtgtag gtcgttcgct ccaagctggg ctgtgtgcac gaaccccccg   3780
ttcagcccga ccgctgcgcc ttatccggta actatcgtct tgagtccaac ccggtaagac   3840
acgacttatc gccactggca gcagccactg gtaacaggat tagcagagcg aggtatgtag   3900
gcggtgctac agagttcttg aagtggtggc ctaactacgg ctacactaga agaacagtat   3960
ttggtatctg cgctctgctg aagccagtta ccttcggaaa aagagttggt agctcttgat   4020
ccggcaaaca aaccaccgct ggtagcggtt tttttgtttg caagcagcag attacgcgca   4080
gaaaaaaagg atctcaagaa gatcctttga tcttttctac ggggtctgac gctcagtgga   4140
acgaaaactc acgttaaggg attttggtca tgagattatc aaaaaggatc ttcacctaga   4200 tcctttttaaa ttaaaaatga agttttaaat caatctaaag tatatatgag taaacttggt   4260
ctgacagtta ccaatgctta atcagtgagg cacctatctc agcgatctgt ctatttcgtt   4320
catccatagt tgcctgactc cccgtcgtgt agataactac gatacgggag ggcttaccat   4380
ctggccccag tgctgcaatg ataccgcgag acccacgctc accggctcca gatttatcag   4440
caataaacca gccagccgga agggccgagc gcagaagtgg tcctgcaact ttatccgcct   4500
ccatccagtc tattaattgt tgccgggaag ctagagtaag tagttcgcca gttaatagtt   4560
tgcgcaacgt tgttgccatt gctacaggca tcgtggtgtc acgctcgtcg tttggtatgg   4620
cttcattcag ctccggttcc caacgatcaa ggcgagttac atgatccccc atgttgtgca   4680
aaaaagcggt tagctccttc ggtcctccga tcgttgtcag aagtaagttg gccgcagtgt   4740
tatcactcat ggttatggca gcactgcata attctcttac tgtcatgcca tccgtaagat   4800
gcttttctgt gactggtgag tactcaacca agtcattctg agaatagtgt atgcggcgac   4860
cgagttgctc ttgcccggcg tcaatacggg ataataccgc gccacatagc agaactttaa   4920
aagtgctcat cattggaaaa cgttcttcgg ggcgaaaact ctcaaggatc ttaccgctgt   4980
tgagatccag ttcgatgtaa cccactcgtg cacccaactg atcttcagca tcttttactt   5040
tcaccagcgt ttctgggtga gcaaaaacag gaaggcaaaa tgccgcaaaa aagggaataa   5100
gggcgacacg gaaatgttga atactcatac tcttcctttt tcaatattat tgaagcattt   5160
atcagggtta ttgtctcatg agcggataca tatttgaatg tatttagaaa aataaacaaa   5220 tagggggttcc gcgcacattt ccccgaaaag tgccacctga cgtcgacgga tcgggagatc   5280 aacttgtttta ttgcagctta taatggttac aaataaagca atagcatcac aaatttcaca   5340
```

```
aataaagcat ttttttcact gcattctagt tgtggtttgt ccaaactcat caatgtatct      5400
tatcatgtct ggatcaactg gataactcaa gctaaccaaa atcatcccaa acttcccacc      5460
ccatacccta ttaccactgc caattaccct gtgggcgcaa ttaaccctca ctaaagggaa      5520
caaaagctgg agctgcaagc ttaatgtagt cttatgcaat actcttgtag tcttgcaaca      5580
tggtaacgat gagttagcaa catgccttac aaggagagaa aaagcaccgt gcatgccgat      5640
tggtggaagt aaggtggtac gatcgtgcct tattaggaag gcaacagacg ggtctgacat      5700
ggattggacg aaccactgaa ttgccgcatt gcagagatat tgtatttaag tgcctagctc      5760
gatacataaa cgggtctctc tggttagacc agatctgagc ctgggagctc tctggctaac      5820
tagggaaccc actgcttaag cctcaataaa gcttgccttg agtgcttcaa gtagtgtgtg      5880
cccgtctgtt gtgtgactct ggtaactaga gatccctcag accctttttag tcagtgtgga      5940 aaatctctag cagtggcgcc cgaacaggga cttgaaagcg aaagggaaac cagaggagct      6000
ctctcgacgc aggactcggc ttgctgaagc gcgcacggca agaggcgagg ggcggcgact      6060
ggtgagtacg ccaaaaattt tgactagcgg aggctagaag gagagagatg ggtgcgagag      6120
cgtcagtatt aagcggggga gaattagatc gcgatgggaa aaaattcggt taaggccagg      6180
gggaaagaaa aaatataaat taaaacatat agtatgggca agcagggagc tagaacgatt      6240
cgcagttaat cctggcctgt tagaaacatc agaaggctgt agacaaatac tgggacagct      6300
acaaccatcc cttcagacag gatcagaaga acttagatca ttatataata cagtagcaac      6360
cctctattgt gtgcatcaaa ggatagagat aaaagacacc aaggaagctt tagacaagat      6420
agaggaagag caaaacaaaa gtaagaccac cgcacagcaa gcggccggcc gctgatcttc      6480
agacctggag gaggagatat gagggacaat taattggaga agtgaattat ataaatataa      6540
agtagtaaaa attgaaccat taggagtagc acccaccaag gcaaagagaa gagtggtgca      6600
gagagaaaaa agagcagtgg gaataggagc tttgttcctt gggttcttgg gagcagcagg      6660
aagcactatg ggcgcagcgt caatgacgct gacggtacag gccagacaat tattgtctgg      6720
tatagtgcag cagcagaaca atttgctgag ggctattgag gcgcaacagc atctgttgca      6780
actcacagtc tggggcatca agcagctcca ggcaagaatc ctggctgtgg aaagatacct      6840
aaaggatcaa cagctcctgg ggatttgggg ttgctctgga aaactcattt gcaccactgc      6900
tgtgccttgg aatgctagtt ggagtaataa atctctggaa cagatttgga atcacacgac      6960
ctggatggag tgggacagag aaattaacaa ttacacaagc ttaatacact ccttaattga      7020
agaatcgcaa aaccagcaag aaaagaatga acaagaatta ttggaattag ataaatgggc      7080
aagtttgtgg aattggttta acataacaaa ttggctgtgg tatataaaat tattcataat      7140
gatagtagga ggcttggtag gtttaagaat agttttttgct gtactttcta tagtgaatag      7200
agttaggcag ggatattcac cattatcgtt tcagacccac ctcccaaccc cgaggggacc      7260
cgacaggccc gaaggaatag aagaagaagg tggagagaga cagagacaga tccattcg       7320 attagtgaac ggatctcgac ggtatcgcct ttaaaagaaa aggggggatt ggggggtaca      7380
gtgcagggga agaatagta  gacataatag caacagacat acaaactaaa gaactacaaa      7440
aacaaattac aaaaattcaa aattttcggg tttattacag gcacagcaga tccagttt       7500 atctaatacg actcactata gggagagaga gagaattacc ctcactaaag ggaggagaag      7560
catgtcgacg aattcctaat acgactcact ataggatatc gttgtctgta ctgccgttgc      7620
cacatagatc atccaaatcc taaaggattt tgtgacttaa aaggtaagta tgtacaaata      7680
cctacaactt gtgctaatga ccctgtgggt tttacactta aaatgcagtt ccgagctcac      7740
```

```
tcgactctct gatcagacga tggtttttact tatcaccaaa tccgcgtagg cagatcgtag    7800
tcagctgatg cacaatcgtt tttaaacggg tttgcggtgt aagtgcagcc cgtcttacac    7860
cgtgcggcac aggcactcga gctgtggaat gtgtgtcagt tagggtgtgg aaagtcccca    7920
ggctccccag caggcagaag tatgcaaagc atgcatctca attagtcagc aaccaggtgt    7980
ggaaagtccc caggctcccc agcaggcaga agtatgcaaa gcatgcatct caattagtca    8040
gcaaccatag tcccgcccct aactccgccc atcccgcccc taactccgcc cagttccgcc    8100
cattctccgc cccatggctg actaattttt tttatttatg cagaggccga ggccgcctct    8160
gcctctgagc tattccagaa gtagtgagga ggcttttttg gaggcctagg cttttgcaaa    8220
aagctcccgg gagcttgtat atccattttc ggatctgatc ggcgcgccat accgg    8275
```

```
<210> SEQ ID NO 10
<211> LENGTH: 24
<212> TYPE: DNA
<213> ORGANISM: Artificial Sequence
<220> FEATURE:
<223> OTHER INFORMATION: Synthesized

<400> SEQUENCE: 10
cactcctcca cctttgacgc tggg                                              24
```

```
<210> SEQ ID NO 11
<211> LENGTH: 29
<212> TYPE: DNA
<213> ORGANISM: Artificial Sequence
<220> FEATURE:
<223> OTHER INFORMATION: Synthesized

<400> SEQUENCE: 11
cacactgaat ctcccctcct cacagttgc                                        29
```

```
<210> SEQ ID NO 12
<211> LENGTH: 29
<212> TYPE: DNA
<213> ORGANISM: Artificial Sequence
<220> FEATURE:
<223> OTHER INFORMATION: Synthesized

<400> SEQUENCE: 12
tacgttgcta tccaggctgt gctatccct                                        29
```

```
<210> SEQ ID NO 13
<211> LENGTH: 28
<212> TYPE: DNA
<213> ORGANISM: Artificial Sequence
<220> FEATURE:
<223> OTHER INFORMATION: Synthesized

<400> SEQUENCE: 13
caagggactt cctgtaacaa cgcatctc                                         28
```

```
<210> SEQ ID NO 14
<211> LENGTH: 23
<212> TYPE: DNA
<213> ORGANISM: Artificial Sequence
<220> FEATURE:
<223> OTHER INFORMATION: Synthesized

<400> SEQUENCE: 14
tctcctctga cttcaacagc gac                                              23
```

```
<210> SEQ ID NO 15
<211> LENGTH: 23
<212> TYPE: DNA
<213> ORGANISM: Artificial Sequence
<220> FEATURE:
<223> OTHER INFORMATION: Synthesized

<400> SEQUENCE: 15
gagcttgaca aagtggtcgt tga                                              23

<210> SEQ ID NO 16
<211> LENGTH: 19
<212> TYPE: DNA
<213> ORGANISM: Artificial Sequence
<220> FEATURE:
<223> OTHER INFORMATION: Synthesized

<400> SEQUENCE: 16
cctgccacac tcagtcccc                                                   19

<210> SEQ ID NO 17
<211> LENGTH: 19
<212> TYPE: DNA
<213> ORGANISM: Artificial Sequence
<220> FEATURE:
<223> OTHER INFORMATION: Synthesized

<400> SEQUENCE: 17
gacaaggtgc ggctcccta                                                   19

<210> SEQ ID NO 18
<211> LENGTH: 21
<212> TYPE: DNA
<213> ORGANISM: Artificial Sequence
<220> FEATURE:
<223> OTHER INFORMATION: Synthesized

<400> SEQUENCE: 18
tgagaccttc aacaccccag c                                                21

<210> SEQ ID NO 19
<211> LENGTH: 20
<212> TYPE: DNA
<213> ORGANISM: Artificial Sequence
<220> FEATURE:
<223> OTHER INFORMATION: Synthesized

<400> SEQUENCE: 19
caccggagtc catcacgatg                                                  20

<210> SEQ ID NO 20
<211> LENGTH: 22
<212> TYPE: DNA
<213> ORGANISM: Artificial Sequence
<220> FEATURE:
<223> OTHER INFORMATION: Synthesized

<400> SEQUENCE: 20
aatgtggccg aggactttga tt                                               22

<210> SEQ ID NO 21
<211> LENGTH: 22
<212> TYPE: DNA
<213> ORGANISM: Artificial Sequence
<220> FEATURE:
<223> OTHER INFORMATION: Synthesized
```

```
<400> SEQUENCE: 21
gagaagtggg gtggctttta gg                                                22

<210> SEQ ID NO 22
<211> LENGTH: 28
<212> TYPE: DNA
<213> ORGANISM: Artificial Sequence
<220> FEATURE:
<223> OTHER INFORMATION: Synthesized

<400> SEQUENCE: 22
ctcactcgac tctctgatca gacgatgg                                          28

<210> SEQ ID NO 23
<211> LENGTH: 25
<212> TYPE: DNA
<213> ORGANISM: Artificial Sequence
<220> FEATURE:
<223> OTHER INFORMATION: Synthesized

<400> SEQUENCE: 23
cggctacagg ctcaccacgt aagac                                             25

<210> SEQ ID NO 24
<211> LENGTH: 25
<212> TYPE: DNA
<213> ORGANISM: Artificial Sequence
<220> FEATURE:
<223> OTHER INFORMATION: Synthesized

<400> SEQUENCE: 24
caccgaggat gcacagctcg ctcta                                             25

<210> SEQ ID NO 25
<211> LENGTH: 24
<212> TYPE: DNA
<213> ORGANISM: Artificial Sequence
<220> FEATURE:
<223> OTHER INFORMATION: Synthesized

<400> SEQUENCE: 25
acgccagctt acgacatgcg aatc                                              24

<210> SEQ ID NO 26
<211> LENGTH: 23
<212> TYPE: DNA
<213> ORGANISM: Artificial Sequence
<220> FEATURE:
<223> OTHER INFORMATION: Synthesized

<400> SEQUENCE: 26
cacatccgca cgccactcgt aac                                               23

<210> SEQ ID NO 27
<211> LENGTH: 24
<212> TYPE: DNA
<213> ORGANISM: Artificial Sequence
<220> FEATURE:
<223> OTHER INFORMATION: Synthesized

<400> SEQUENCE: 27
atcacgcatg cacactccag cacc                                              24

<210> SEQ ID NO 28
```

```
<211> LENGTH: 23
<212> TYPE: DNA
<213> ORGANISM: Artificial Sequence
<220> FEATURE:
<223> OTHER INFORMATION: Synthesized

<400> SEQUENCE: 28
agcctcaacc gctgaacagt gcc                                                 23

<210> SEQ ID NO 29
<211> LENGTH: 26
<212> TYPE: DNA
<213> ORGANISM: Artificial Sequence
<220> FEATURE:
<223> OTHER INFORMATION: Synthesized

<400> SEQUENCE: 29
cctcagcgaa gactaatggc gagatg                                             26

<210> SEQ ID NO 30
<211> LENGTH: 21
<212> TYPE: DNA
<213> ORGANISM: Artificial Sequence
<220> FEATURE:
<223> OTHER INFORMATION: Synthesized

<400> SEQUENCE: 30
ccctgtgggt tttacactta a                                                  21

<210> SEQ ID NO 31
<211> LENGTH: 19
<212> TYPE: DNA
<213> ORGANISM: Artificial Sequence
<220> FEATURE:
<223> OTHER INFORMATION: Synthesized

<400> SEQUENCE: 31
acgattgtgc atcagctga                                                     19

<210> SEQ ID NO 32
<211> LENGTH: 22
<212> TYPE: DNA
<213> ORGANISM: Artificial Sequence
<220> FEATURE:
<223> OTHER INFORMATION: Synthesized

<400> SEQUENCE: 32
gtgaratggt catgtgtggc gg                                                 22

<210> SEQ ID NO 33
<211> LENGTH: 26
<212> TYPE: DNA
<213> ORGANISM: Artificial Sequence
<220> FEATURE:
<223> OTHER INFORMATION: Synthesized

<400> SEQUENCE: 33
caratgttaa asacactatt agcata                                             26

<210> SEQ ID NO 34
<211> LENGTH: 22
<212> TYPE: DNA
<213> ORGANISM: Artificial Sequence
<220> FEATURE:
<223> OTHER INFORMATION: Synthesized

<400> SEQUENCE: 34
```

-continued

```
ggggaacttc tcctgctaga at                                           22

<210> SEQ ID NO 35
<211> LENGTH: 22
<212> TYPE: DNA
<213> ORGANISM: Artificial Sequence
<220> FEATURE:
<223> OTHER INFORMATION: Synthesized

<400> SEQUENCE: 35
cagacatttt gctctcaagc tg                                           22

<210> SEQ ID NO 36
<211> LENGTH: 20
<212> TYPE: DNA
<213> ORGANISM: Artificial Sequence
<220> FEATURE:
<223> OTHER INFORMATION: Synthesized

<400> SEQUENCE: 36
gaccccaaaa tcagcgaaat                                              20

<210> SEQ ID NO 37
<211> LENGTH: 24
<212> TYPE: DNA
<213> ORGANISM: Artificial Sequence
<220> FEATURE:
<223> OTHER INFORMATION: Synthesized

<400> SEQUENCE: 37
tctggttact gccagttgaa tctg                                         24

<210> SEQ ID NO 38
<211> LENGTH: 20
<212> TYPE: DNA
<213> ORGANISM: Artificial Sequence
<220> FEATURE:
<223> OTHER INFORMATION: Synthesized

<400> SEQUENCE: 38
ttacaaacat tggccgcaaa                                              20

<210> SEQ ID NO 39
<211> LENGTH: 18
<212> TYPE: DNA
<213> ORGANISM: Artificial Sequence
<220> FEATURE:
<223> OTHER INFORMATION: Synthesized

<400> SEQUENCE: 39
gcgcgacatt ccgaagaa                                                18

<210> SEQ ID NO 40
<211> LENGTH: 22
<212> TYPE: DNA
<213> ORGANISM: Artificial Sequence
<220> FEATURE:
<223> OTHER INFORMATION: Synthesized

<400> SEQUENCE: 40
gggagccttg aatacaccaa aa                                           22

<210> SEQ ID NO 41
<211> LENGTH: 21
<212> TYPE: DNA
```

```
<213> ORGANISM: Artificial Sequence
<220> FEATURE:
<223> OTHER INFORMATION: Synthesized

<400> SEQUENCE: 41
tgtagcacga ttgcagcatt g                                              21

<210> SEQ ID NO 42
<211> LENGTH: 21
<212> TYPE: DNA
<213> ORGANISM: Artificial Sequence
<220> FEATURE:
<223> OTHER INFORMATION: Synthesized

<400> SEQUENCE: 42
ccagatccat caaaaccaag c                                              21

<210> SEQ ID NO 43
<211> LENGTH: 21
<212> TYPE: DNA
<213> ORGANISM: Artificial Sequence
<220> FEATURE:
<223> OTHER INFORMATION: Synthesized

<400> SEQUENCE: 43
tgcacaaatg aggtctctag c                                              21

<210> SEQ ID NO 44
<211> LENGTH: 26
<212> TYPE: DNA
<213> ORGANISM: Artificial Sequence
<220> FEATURE:
<223> OTHER INFORMATION: Synthesized

<400> SEQUENCE: 44
acaggtacgt taatagttaa tagcgt                                        26

<210> SEQ ID NO 45
<211> LENGTH: 22
<212> TYPE: DNA
<213> ORGANISM: Artificial Sequence
<220> FEATURE:
<223> OTHER INFORMATION: Synthesized

<400> SEQUENCE: 45
atattgcagc agtacgcaca ca                                            22

<210> SEQ ID NO 46
<211> LENGTH: 362
<212> TYPE: DNA
<213> ORGANISM: Artificial Sequence
<220> FEATURE:
<223> OTHER INFORMATION: Synthesized

<400> SEQUENCE: 46
ccctcactaa agggaggaga agcatgtcga cgaattccta atacgactca ctataggata    60
tcgttgtctg tactgccgtt gccacataga tcatccaaat cctaaaggat tttgtgactt   120
aaaaggtaag tatgtacaaa tacctacaac ttgtgctaat gaccctgtgg gttttacact   180
taaaatgcag ttccgagctc actcgactct ctgatcagac gatggtttta cttatcacca   240
aatccgcgta ggcagatcgt agtcagctga tgcacaatcg tttttaaacg ggtttgcggt   300
gtaagtgcag cccgtcttac accgtgcggc acaggcactc gagctgtgga atgtgtgtca   360
gt                                                                 362
```

-continued

```
<210> SEQ ID NO 47
<211> LENGTH: 56
<212> TYPE: DNA
<213> ORGANISM: Artificial Sequence
<220> FEATURE:
<223> OTHER INFORMATION: Synthesized

<400> SEQUENCE: 47
ccctcactaa agggaggaga agcatgtcga cgaattccta atacgactca ctatag        56

<210> SEQ ID NO 48
<211> LENGTH: 18
<212> TYPE: DNA
<213> ORGANISM: Artificial Sequence
<220> FEATURE:
<223> OTHER INFORMATION: Synthesized

<400> SEQUENCE: 48
ctggaatagc tcagaggc                                                  18

<210> SEQ ID NO 49
<211> LENGTH: 5496
<212> TYPE: DNA
<213> ORGANISM: Artificial Sequence
<220> FEATURE:
<223> OTHER INFORMATION: Synthesized

<400> SEQUENCE: 49
gggtctctct ggttagacca gatctgagcc tgggagctct ctggctaact agggaaccca      60
ctgcttaagc ctcaataaag cttgccttga gtgcttcaag tagtgtgtgc ccgtctgttg     120
tgtgactctg gtaactagag atccctcaga ccctttttagt cagtgtggaa aatctctagc    180
agtggcgccc gaacagggac ttgaaagcga aagggaaacc agaggagctc tctcgacgca     240
ggactcggct tgctgaagcg cgcacggcaa gaggcgaggg gcggcgactg gtgagtacgc     300
caaaaatttt gactagcgga ggctagaagg agagagatgg gtgcgagagc gtcagtatta    360 agcggggggag aattagatcg cgatgggaaa aaattcggtt aaggccaggg ggaaagaaaa   420
aatataaatt aaaacatata gtatgggcaa gcagggagct agaacgattc gcagttaatc    480
ctggcctgtt agaaacatca gaaggctgta gacaaatact gggacagcta caaccatccc    540
ttcagacagg atcagaagaa cttagatcat tatataatac agtagcaacc ctctattgtg    600
tgcatcaaag gatagagata aaagacacca aggaagcttt agacaagata gaggaagagc    660
aaaacaaaag taagaccacc gcacagcaag cggccggccg ctgatcttca gacctggagg    720
aggagatatg agggacaatt aattggagaa gtgaattata taaatataaa gtagtaaaaa    780
ttgaaccatt aggagtagca cccaccaagg caaagagaag agtggtgcag agagaaaaaa    840
gagcagtggg aataggagct ttgttccttg ggttcttggg agcagcagga agcactatgg    900
gcgcagcgtc aatgacgctg acggtacagg ccagacaatt attgtctggt atagtgcagc    960
agcagaacaa tttgctgagg gctattgagg cgcaacagca tctgttgcaa ctcacagtct   1020
ggggcatcaa gcagctccag gcaagaatcc tggctgtgga agataccta aaggatcaac    1080 agctcctggg gatttggggt tgctctggaa aactcatttg caccactgct gtgccttgga    1140
atgctagttg gagtaataaa tctctggaac agatttggaa tcacacgacc tggatggagt    1200
gggacagaga aattaacaat tacacaagct taatacactc cttaattgaa gaatcgcaaa    1260
accagcaaga aaagaatgaa caagaattat tggaattaga taaatgggca agtttgtgga    1320
```

-continued

```
attggtttaa cataacaaat tggctgtggt atataaaatt attcataatg atagtaggag    1380
gcttggtagg tttaagaata gttttttgctg tactttctat agtgaataga gttaggcagg   1440
gatattcacc attatcgttt cagacccacc tcccaacccc gaggggaccc gacaggcccg   1500
aaggaataga agaagaaggt ggagagagag acagagacag atccattcga ttagtgaacg   1560
gatctcgacg gtatcgcctt taaaagaaaa gggggggattg gggggtacag tgcaggggaa   1620
agaatagtag acataatagc aacagacata caaactaaag aactacaaaa acaaattaca   1680
aaaattcaaa attttcgggt ttattacagg gacagcagag atccagttta tctaatacga   1740
ctcactatag ggagagagag agaattaccc tcactaaagg gaggagaagc atgtcgacga   1800
attcctaata cgactcacta taggatatcg ttgtctgtac tgccgttgcc acatagatca   1860
tccaaatcct aaaggatttt gtgacttaaa aggtaagtat gtacaaatac ctacaacttg   1920
tgctaatgac cctgtgggtt ttacacttaa aatgcagttc cgagctcact cgactctctg   1980
atcagacgat ggttttactt atcaccaaat ccgcgtaggc agatcgtagt cagctgatgc   2040
acaatcgttt ttaaacgggt ttgcggtgta agtgcagccc gtcttacacc gtgcggcaca   2100
ggcactcgag ctgtggaatg tgtgtcagtt agggtgtgga aagtccccag gctccccagc   2160
aggcagaagt atgcaaagca tgcatctcaa ttagtcagca accaggtgtg gaaagtcccc   2220
aggctcccca gcaggcagaa gtatgcaaag catgcatctc aattagtcag caaccatagt   2280 cccgcccta actccgccca tcccgcccct aactccgccc agttccgccc attctccgcc   2340
ccatggctga ctaattttt ttatttatgc agaggccgag gccgcctctg cctctgagct   2400
attccagaag tagtgaggag gcttttttgg aggcctaggc ttttgcaaaa agctcccggg   2460
agcttgtata tccattttcg gatctgatcg gcgcgccata ccggtcgcca ccatggtgag   2520
caagggcgag gagctgttca ccggggtggt gcccatcctg gtcgagctgg acggcgacgt   2580
aaacggccac aagttcagcg tgtccggcga gggcgagggc gatgccacct acggcaagct   2640
gaccctgaag ttcatctgca ccaccggcaa gctgcccgtg ccctggccca ccctcgtgac   2700
caccctgacc tacggcgtgc agtgcttcag ccgctacccc gaccacatga agcagcacga   2760
cttcttcaag tccgccatgc ccgaaggcta cgtccaggag cgcaccatct tcttcaagga   2820
cgacggcaac tacaagaccc gcgccgaggt gaagttcgag ggcgacaccc tggtgaaccg   2880
catcgagctg aagggcatcg acttcaagga ggacggcaac atcctggggc acaagctgga   2940
gtacaactac aacagccaca cgtctatat catggccgac aagcagaaga acggcatcaa   3000
ggtgaacttc aagatccgcc acaacatcga ggacggcagc gtgcagctcg ccgaccacta   3060
ccagcagaac acccccatcg cgacggccc cgtgctgctg cccgacaacc actacctgag   3120
cacccagtcc gccctgagca aagaccccaa cgagaagcgc gatcacatgg tcctgctgga   3180
gttcgtgacc gccgccggga tcactctcgg catggacgag ctgtacaagt aaagcggccg   3240 cgatccccgcc cctctccctc ccccccccct aacgttactg gccgaagccg cttggaataa   3300
ggccggtgtg cgtttgtcta tatgttattt tccaccatat tgccgtcttt tggcaatgtg   3360
agggcccgga aacctggccc tgtcttcttg acgagcattc ctaggggtct ttcccctctc   3420
gccaaaggaa tgcaaggtct gttgaatgtc gtgaaggaag cagttcctct ggaagcttct   3480
tgaagacaaa caacgtctgt agcgaccctt tgcaggcagc ggaacccccc acctggcgac   3540
aggtgcctct gcggccaaaa gccacgtgta taagatacac ctgcaaaggc ggcacaaccc   3600
cagtgccacg ttgtgagttg gatagttgtg gaaagagtca aatggctctc ctcaagcgta   3660
ttcaacaagg ggctgaagga tgcccagaag gtaccccatt gtatgggatc tgatctgggg   3720
```

-continued

```
cctcggtgca catgctttac atgtgtttag tcgaggttaa aaaaacgtct aggcccccg     3780 aaccacgggg acgtggtttt cctttgaaaa acacgatgat aagcttgcca caacccacaa     3840
ggagacgacc ttccatgacc gagtacaagc ccacggtgcg cctcgccacc cgcgacgacg     3900
tcccccgggc cgtacgcacc ctcgccgccg cgttcgccga ctaccccgcc acgcgccaca     3960
ccgtcgaccc ggaccgccac atcgagcggg tcaccgagct gcaagaactc ttcctcacgc     4020
gcgtcgggct cgacatcggc aaggtgtggg tcgcggacga cggcgccgcg gtggcggtct     4080
ggaccacgcc ggagagcgtc gaagcggggg cggtgttcgc cgagatcggc ccgcgcatgg     4140
ccgagttgag cggttcccgg ctggccgcgc agcaacagat ggaaggcctc ctggcgccgc     4200
accggcccaa ggagcccgcg tggttcctgg ccaccgtcgg cgtctcgccc gaccaccagg     4260
gcaagggtct gggcagcgcc gtcgtgctcc cggagtgga ggcggccgag cgcgccgggg     4320
tgcccgcctt cctggagacc tccgcgcccc gcaacctccc cttctacgag cggctcggct     4380
tcaccgtcac cgccgacgtc gaggtgcccg aaggaccgcg cacctggtgc atgacccgca     4440
agcccggtgc ctagacgcgt ctggaacaat caacctctgg attacaaaat ttgtgaaaga     4500
ttgactggta ttcttaacta tgttgctcct tttacgctat gtggatacgc tgctttaatg     4560
cctttgtatc atgctattgc ttcccgtatg gctttcattt tctcctcctt gtataaatcc     4620
tggttgctgt ctctttatga ggagttgtgg cccgttgtca ggcaacgtgg cgtggtgtgc     4680
actgtgtttg ctgacgcaac ccccactggt tggggcattg ccaccacctg tcagctcctt     4740
tccgggactt tcgctttccc cctccctatt gccacggcgg aactcatcgc cgcctgcctt     4800
gcccgctgct ggacaggggc tcggctgttg ggcactgaca attccgtggt gttgtcgggg     4860
aagctgacgt cctttccatg gctgctcgcc tgtgttgcca cctggattct gcgcgggacg     4920
tccttctgct acgtcccttc ggccctcaat ccagcggacc ttccttcccg cggcctgctg     4980
ccggctctgc ggcctcttcc gcgtcttcgc cttcgccctc agacgagtcg gatctccctt     5040
tgggccgcct ccccgcctgg aattaattct gcagtcgaga cctagaaaaa catggagcaa     5100
tcacaagtag caatacagca gctaccaatg ctgattgtgc ctggctagaa gcacaagagg     5160
aggaggaggt gggttttttcc agtcacacct caggaccttt aagaccaatg acttacaagg     5220
cagctgtaga tcttagccac ttttttaaaag aaaagagggg actggaaggg ctaattcact     5280
cccaacgaag acaagatctg cttttttgcct gtactgggtc tctctggtta gaccagatct     5340
gagcctggga gctctctggc taactaggga acccactgct taagcctcaa taaagcttgc     5400
cttgagtgct tcaagtagtg tgtgcccgtc tgttgtgtga ctctggtaac tagagatccc     5460
tcagaccctt ttagtcagtg tggaaaatct ctagca                               5496
```

<210> SEQ ID NO 50
<211> LENGTH: 8370
<212> TYPE: DNA
<213> ORGANISM: Artificial Sequence
<220> FEATURE:
<223> OTHER INFORMATION: Synthesized

<400> SEQUENCE: 50

```
tcggatctga tcggcgcgcc ataccggtcg ccaccatggt gagcaagggc gaggagctgt      60
tcaccggggt ggtgcccatc ctggtcgagc tggacggcga cgtaaacggc cacaagttca     120
gcgtgtccgg cgagggcgag ggcgatgcca cctacggcaa gctgaccctg aagttcatct     180
gcaccaccgg caagctgccc gtgccctggc ccaccctcgt gaccaccctg acctacggcg     240
```

```
tgcagtgctt cagccgctac cccgaccaca tgaagcagca cgacttcttc aagtccgcca    300
tgcccgaagg ctacgtccag gagcgcacca tcttcttcaa ggacgacggc aactacaaga    360
cccgcgccga ggtgaagttc gagggcgaca ccctggtgaa ccgcatcgag ctgaagggca    420
tcgacttcaa ggaggacggc aacatcctgg ggcacaagct ggagtacaac tacaacagcc    480
acaacgtcta tatcatggcc gacaagcaga agaacggcat caaggtgaac ttcaagatcc    540
gccacaacat cgaggacggc agcgtgcagc tcgccgacca ctaccagcag aacacccca    600 tcggcgacgg ccccgtgctg ctgcccgaca accactacct gagcacccag tccgccctga    660
gcaaagaccc caacgagaag cgcgatcaca tggtcctgct ggagttcgtg accgccgccg    720
ggatcactct cggcatggac gagctgtaca agtaaagcgg ccgcgatccc gcccctctcc    780
ctcccccccc cctaacgtta ctggccgaag ccgcttggaa taaggccggt gtgcgtttgt    840
ctatatgtta ttttccacca tattgccgtc ttttggcaat gtgagggccc ggaaacctgg    900
ccctgtcttc ttgacgagca ttcctagggg tctttcccct ctcgccaaag gaatgcaagg    960
tctgttgaat gtcgtgaagg aagcagttcc tctggaagct tcttgaagac aaacaacgtc   1020
tgtagcgacc ctttgcaggc agcggaaccc cccacctggc gacaggtgcc tctgcggcca   1080
aaagccacgt gtataagata cacctgcaaa ggcggcacaa ccccagtgcc acgttgtgag   1140
ttggatagtt gtggaaagag tcaaatggct ctcctcaagc gtattcaaca aggggctgaa   1200
ggatgcccag aaggtacccc attgtatggg atctgatctg gggcctcggt gcacatgctt   1260
tacatgtgtt tagtcgaggt taaaaaaacg tctaggcccc ccgaaccacg gggacgtggt   1320
tttcctttga aaaacacgat gataagcttg ccacaaccca caaggagacg accttccatg   1380
accgagtaca agcccacggt gcgcctcgcc accgcgacg acgtccccg ggccgtacgc      1440 accctcgccg ccgcgttcgc cgactacccc gccacgcgcc acaccgtcga cccggaccgc   1500
cacatcgagc gggtcaccga gctgcaagaa ctcttcctca cgcgcgtcgg gctcgacatc   1560
ggcaaggtgt gggtcgcgga cgacggcgcc gcggtggcgg tctggaccac gccggagagc   1620
gtcgaagcgg gggcggtgtt cgccgagatc ggcccgcgca tggccgagtt gagcggttcc   1680
cggctggccg cgcagcaaca gatggaaggc ctcctggcgc cgcaccggcc caaggagccc   1740
gcgtggttcc tggccaccgt cggcgtctcg cccgaccacc agggcaaggg tctgggcagc   1800
gccgtcgtgc tccccggagt ggaggcggcc gagcgcgccg gggtgcccgc cttcctggag   1860
acctccgcgc cccgcaacct ccccttctac gagcggctcg gcttcaccgt caccgccgac   1920
gtcgaggtgc ccgaaggacc gcgcacctgg tgcatgaccc gcaagcccgg tgcctagacg   1980
cgtctggaac aatcaacctc tggattacaa aatttgtgaa agattgactg gtattcttaa   2040
ctatgttgct cctttttacgc tatgtggata cgctgcttta atgcctttgt atcatgctat   2100
tgcttcccgt atggctttca ttttctcctc cttgtataaa tcctggttgc tgtctcttta   2160
tgaggagttg tggcccgttg tcaggcaacg tggcgtggtg tgcactgtgt ttgctgacgc   2220
aacccccact ggttggggca ttgccaccac ctgtcagctc ctttccggga ctttcgcttt   2280 cccccctccct attgccacgg cggaactcat cgccgcctgc cttgcccgct gctggacagg   2340
ggctcggctg ttgggcactg acaattccgt ggtgttgtcg gggaagctga cgtcctttcc   2400
atggctgctc gcctgtgttg ccacctggat tctgcgcggg acgtccttct gctacgtccc   2460
ttcggccctc aatccagcgg accttccttc ccgcggcctg ctgccggctc tgcggcctct   2520
tccgcgtctt cgccttcgcc ctcagacgag tcggatctcc ctttgggccg cctccccgcc   2580
tggaattaat tctgcagtcg agacctagaa aaacatggag caatcacaag tagcaataca   2640
```

-continued

```
gcagctacca atgctgattg tgcctggcta gaagcacaag aggaggagga ggtgggtttt    2700
tccagtcaca cctcaggacc tttaagacca atgacttaca aggcagctgt agatcttagc    2760 cacttttaa aagaaaagag gggactggaa gggctaattc actcccaacg aagacaagat    2820 ctgcttttg cctgtactgg gtctctctgg ttagaccaga tctgagcctg ggagctctct    2880
ggctaactag ggaacccact gcttaagcct caataaagct tgccttgagt gcttcaagta    2940
gtgtgtgccc gtctgttgtg tgactctggt aactagagat ccctcagacc cttttagtca    3000
gtgtggaaaa tctctagcag tagtagttca tgtcatctta ttattcagta tttataactt    3060
gcaaagaaat gaatatcaga gagtgagagg ctagcgtttt accgtcgacc tctagctaga    3120
gcttggcgta atcatggtca tagctgtttc ctgtgtgaaa ttgttatccg ctcacaattc    3180
cacacaacat acgagccgga agcataaagt gtaaagcctg gggtgcctaa tgagtgagct    3240
aactcacatt aattgcgttg cgctcactgc ccgctttcca gtcgggaaac ctgtcgtgcc    3300
agctgcatta atgaatcggc caacgcgcgg ggagaggcgg tttgcgtatt gggcgctctt    3360
ccgcttcctc gctcactgac tcgctgcgct cggtcgttcg gctgcggcga gcggtatcag    3420
ctcactcaaa ggcggtaata cggttatcca cagaatcagg ggataacgca ggaaagaaca    3480
tgtgagcaaa aggccagcaa aaggccagga accgtaaaaa ggccgcgttg ctggcgtttt    3540
tccataggct ccgccccct gacgagcatc acaaaaatcg acgctcaagt cagaggtggc    3600
gaaacccgac aggactataa agataccagg cgtttccccc tggaagctcc ctcgtgcgct    3660
ctcctgttcc gaccctgccg cttaccggat acctgtccgc ctttctccct tcgggaagcg    3720
tggcgctttc tcatagctca cgctgtaggt atctcagttc ggtgtaggtc gttcgctcca    3780
agctgggctg tgtgcacgaa ccccccgttc agcccgaccg ctgcgcctta ccggtaact    3840 atcgtcttga gtccaacccg gtaagacacg acttatcgcc actggcagca gccactggta    3900
acaggattag cagagcgagg tatgtaggcg gtgctacaga gttcttgaag tggtggccta    3960
actacggcta cactagaaga acagtatttg gtatctgcgc tctgctgaag ccagttacct    4020
tcggaaaaag agttggtagc tcttgatccg gcaaacaaac caccgctggt agcggttttt    4080
ttgtttgcaa gcagcagatt acgcgcagaa aaaaggatc tcaagaagat cctttgatct    4140
tttctacggg gtctgacgct cagtggaacg aaaactcacg ttaagggatt ttggtcatga    4200
gattatcaaa aaggatcttc acctagatcc ttttaaatta aaaatgaagt tttaaatcaa    4260
tctaaagtat atatgagtaa acttggtctg acagttacca atgcttaatc agtgaggcac    4320
ctatctcagc gatctgtcta tttcgttcat ccatagttgc ctgactcccc gtcgtgtaga    4380
taactacgat acgggagggc ttaccatctg gccccagtgc tgcaatgata ccgcgagacc    4440
cacgctcacc ggctccagat ttatcagcaa taaaccagcc agccggaagg ccgagcgca    4500 gaagtggtcc tgcaacttta tccgcctcca tccagtctat taattgttgc cgggaagcta    4560
gagtaagtag ttcgccagtt aatagtttgc gcaacgttgt tgccattgct acaggcatcg    4620
tggtgtcacg ctcgtcgttt ggtatggctt cattcagctc cggttcccaa cgatcaaggc    4680
gagttacatg atcccccatg ttgtgcaaaa aagcggttag ctccttcggt cctccgatcg    4740
ttgtcagaag taagttggcc gcagtgttat cactcatggt tatggcagca ctgcataatt    4800
ctcttactgt catgccatcc gtaagatgct tttctgtgac tggtgagtac tcaaccaagt    4860
cattctgaga atagtgtatg cggcgaccga gttgctcttg cccggcgtca atacgggata    4920
ataccgcgcc acatagcaga actttaaaag tgctcatcat tggaaaacgt tcttcggggc    4980
```

-continued

```
gaaaactctc aaggatctta ccgctgttga gatccagttc gatgtaaccc actcgtgcac    5040
ccaactgatc ttcagcatct tttactttca ccagcgtttc tgggtgagca aaaacaggaa    5100
ggcaaaatgc cgcaaaaaag ggaataaggg cgacacggaa atgttgaata ctcatactct    5160
tcctttttca atattattga agcatttatc agggttattg tctcatgagc ggatacatat    5220
ttgaatgtat ttagaaaaat aaacaaatag gggttccgcg cacatttccc cgaaaagtgc    5280
cacctgacgt cgacggatcg ggagatcaac ttgtttattg cagcttataa tggttacaaa    5340
taaagcaata gcatcacaaa tttcacaaat aaagcatttt tttcactgca ttctagttgt    5400
ggtttgtcca aactcatcaa tgtatcttat catgtctgga tcaactggat aactcaagct    5460
aaccaaaatc atcccaaact tcccacccca taccctatta ccactgccaa ttaccctgtg    5520
ggcgcaatta accctcacta aagggaacaa aagctggagc tgcaagctta atgtagtctt    5580
atgcaatact cttgtagtct tgcaacatgg taacgatgag ttagcaacat gccttacaag    5640
gagagaaaaa gcaccgtgca tgccgattgg tggaagtaag gtggtacgat cgtgccttat    5700
taggaaggca acagacgggt ctgacatgga ttggacgaac cactgaattg ccgcattgca    5760
gagatattgt atttaagtgc ctagctcgat acataaacgg gtctctctgg ttagaccaga    5820
tctgagcctg ggagctctct ggctaactag ggaacccact gcttaagcct caataaagct    5880
tgccttgagt gcttcaagta gtgtgtgccc gtctgttgtg tgactctggt aactagagat    5940
ccctcagacc ctttttagtca gtgtggaaaa tctctagcag tggcgcccga acagggactt    6000
gaaagcgaaa gggaaaccag aggagctctc tcgacgcagg actcggcttg ctgaagcgcg    6060
cacggcaaga ggcgaggggc ggcgactggt gagtacgcca aaaattttga ctagcggagg    6120
ctagaaggag agagatgggt gcgagagcgt cagtattaag cgggggagaa ttagatcgcg    6180
atgggaaaaa attcggttaa ggccaggggg aaagaaaaaa tataaattaa aacatatagt    6240
atgggcaagc agggagctag aacgattcgc agttaatcct ggcctgttag aaacatcaga    6300
aggctgtaga caaatactgg gacagctaca accatccctt cagacaggat cagaagaact    6360
tagatcatta tataatacag tagcaaccct ctattgtgtg catcaaagga tagagataaa    6420
agacaccaag gaagctttag acaagataga ggaagagcaa aacaaaagta agaccaccgc    6480
acagcaagcg gccggccgct gatcttcaga cctggaggag gagatatgag ggacaattaa    6540
ttggagaagt gaattatata aatataaagt agtaaaaatt gaaccattag gagtagcacc    6600
caccaaggca aagagaagag tggtgcagag agaaaaaaga gcagtgggaa taggagcttt    6660
gttccttggg ttcttgggag cagcaggaag cactatgggc gcagcgtcaa tgacgctgac    6720
ggtacaggcc agacaattat tgtctggtat agtgcagcag cagaacaatt tgctgagggc    6780
tattgaggcg caacagcatc tgttgcaact cacagtctgg ggcatcaagc agctccaggc    6840
aagaatcctg gctgtggaaa gatacctaaa ggatcaacag ctcctgggga tttggggttg    6900
ctctggaaaa ctcatttgca ccactgctgt gccttggaat gctagttgga gtaataaatc    6960
tctggaacag atttggaatc acacgacctg gatggagtgg gacagagaaa ttaacaatta    7020
cacaagctta atacactcct taattgaaga atcgcaaaac cagcaagaaa agaatgaaca    7080
agaattattg gaattagata aatgggcaag tttgtggaat tggtttaaca taacaaattg    7140
gctgtggtat ataaaattat tcataatgat agtaggaggc ttggtaggtt taagaatagt    7200
ttttgctgta ctttctatag tgaatagagt taggcaggga tattcaccat tatcgtttca    7260
gacccacctc ccaaccccga ggggacccga caggcccgaa ggaatagaag aagaaggtgg    7320
agagagagac agagacagat ccattcgatt agtgaacgga tctcgacggt atcgccttta    7380
```

```
aaagaaaagg gggattggg gggtacagtg caggggaaag aatagtagac ataatagcaa    7440
cagacataca aactaaagaa ctacaaaaac aaattacaaa aattcaaaat tttcgggttt    7500
attacaggga cagcagagat ccagtttatc taatacgact cactataggg agagagagag    7560
aattaccctc actaaaggga ggagaagcat gtcgacgaat tcctaatacg actcactata    7620
ggatatcagt ctagggaaag tcattcagtg gatgtgatct tggctcacag gggacgatgt    7680
caagctcttc ctggctcctt ctcagccttg ttgctgtaac tgctgctcag tccaccattg    7740
aggaacaggc caagacattt ttggacaagt ttaaccacga agccgaagac ctgttctatc    7800
aaagttcact tgcttcttgg aattataaca ccaatattac tgaagagaat gtccaaaaca    7860
tgaataatgc tggggacaaa tggtctgcct ttttaaagga acagtccaca cttgcccaaa    7920
tgtatccact acaagaaatt cagaatctca cagtcaagct tcagctgcag gctcttcagc    7980
aaaatgggtc ttagtagctc gagctgtgga atgtgtgtca gttagggtgt ggaaagtccc    8040
caggctcccc agcaggcaga agtatgcaaa gcatgcatct caattagtca gcaaccaggt    8100
gtggaaagtc cccaggctcc ccagcaggca gaagtatgca aagcatgcat ctcaattagt    8160
cagcaaccat agtcccgccc ctaactccgc ccatcccgcc cctaactccg cccagttccg    8220
cccattctcc gccccatggc tgactaattt ttttttattta tgcagaggcc gaggccgcct    8280
ctgcctctga gctattccag aagtagtgag gaggcttttt tggaggccta ggcttttgca    8340
aaaagctccc gggagcttgt atatccattt                                    8370
```

<210> SEQ ID NO 51
<211> LENGTH: 8370
<212> TYPE: DNA
<213> ORGANISM: Artificial Sequence
<220> FEATURE:
<223> OTHER INFORMATION: Synthesized

<400> SEQUENCE: 51

```
tcggatctga tcggcgcgcc ataccggtcg ccaccatggt gagcaagggc gaggagctgt      60
tcaccggggt ggtgcccatc ctggtcgagc tggacggcga cgtaaacggc cacaagttca     120
gcgtgtccgg cgagggcgag ggcgatgcca cctacggcaa gctgaccctg aagttcatct     180
gcaccaccgg caagctgccc gtgccctggc ccaccctcgt gaccaccctg acctacggcg     240
tgcagtgctt cagccgctac cccgaccaca tgaagcagca cgacttcttc aagtccgcca     300
tgcccgaagg ctacgtccag gagcgcacca tcttcttcaa ggacgacggc aactacaaga     360
cccgcgccga ggtgaagttc gagggcgaca ccctggtgaa ccgcatcgag ctgaagggca     420
tcgacttcaa ggaggacggc aacatcctgg ggcacaagct ggagtacaac tacaacagcc     480
acaacgtcta tcatggccgac caagcagaa gaacggcgat caaggtgaac ttcaagatcc     540
gccacaacat cgaggacggc agcgtgcagc tcgccgacca ctaccagcag aacacccca     600 tcggcgacgg ccccgtgctg ctgcccgaca ccactacct gagcacccag tccgccctga     660
gcaaagaccc caacgagaag cgcgatcaca tggtcctgct ggagttcgtg accgccgccg     720
ggatcactct cggcatggac gagctgtaca agtaaagcgg ccgcgatccc gcccctctcc     780 ctccccccccc cctaacgtta ctggccgaag ccgcttggaa taaggccggt gtgcgtttgt     840
ctatatgtta ttttccacca tattgccgtc ttttggcaat gtgagggccc ggaaacctgg     900
ccctgtcttc ttgacgagca ttcctagggg tctttcccct ctcgccaaag gaatgcaagg     960
tctgttgaat gtcgtgaagg aagcagttcc tctggaagct tcttgaagac aaacaacgtc    1020
```

-continued

```
tgtagcgacc ctttgcaggc agcggaaccc cccacctggc gacaggtgcc tctgcggcca   1080
aaagccacgt gtataagata cacctgcaaa ggcggcacaa ccccagtgcc acgttgtgag   1140
ttggatagtt gtggaaagag tcaaatggct ctcctcaagc gtattcaaca aggggctgaa   1200
ggatgcccag aaggtacccc attgtatggg atctgatctg gggcctcggt gcacatgctt   1260
tacatgtgtt tagtcgaggt taaaaaaacg tctaggcccc ccgaaccacg gggacgtggt   1320
tttcctttga aaaacacgat gataagcttg ccacaaccca caaggagacg accttccatg   1380
accgagtaca agcccacggt gcgcctcgcc acccgcgacg acgtcccccg ggccgtacgc   1440
accctcgccg ccgcgttcgc cgactacccc gccacgcgcc acaccgtcga cccggaccgc   1500
cacatcgagc gggtcaccga gctgcaagaa ctcttcctca cgcgcgtcgg gctcgacatc   1560
ggcaaggtgt gggtcgcgga cgacggcgcc gcggtggcgg tctggaccac gccggagagc   1620
gtcgaagcgg gggcggtgtt cgccgagatc ggcccgcgca tggccgagtt gagcggttcc   1680
cggctggccg cgcagcaaca gatggaaggc ctcctggcgc cgcaccggcc caaggagccc   1740
gcgtggttcc tggccaccgt cggcgtctcg cccgaccacc agggcaaggg tctgggcagc   1800
gccgtcgtgc tcccggagt ggaggcggcc gagcgcgccg gggtgcccgc cttcctggag   1860
acctccgcgc cccgcaacct ccccttctac gagcggctcg gcttcaccgt caccgccgac   1920
gtcgaggtgc ccgaaggacc gcgcacctgg tgcatgaccc gcaagcccgg tgcctagacg   1980
cgtctggaac aatcaacctc tggattacaa aatttgtgaa agattgactg gtattcttaa   2040
ctatgttgct cctttacgc tatgtggata cgctgcttta atgcctttgt atcatgctat   2100
tgcttcccgt atggctttca ttttctcctc cttgtataaa tcctggttgc tgtctcttta   2160
tgaggagttg tggcccgttg tcaggcaacg tggcgtggtg tgcactgtgt ttgctgacgc   2220
aacccccact ggttggggca ttgccaccac ctgtcagctc ctttccggga ctttcgcttt   2280 cccctccct attgccacgg cggaactcat cgccgcctgc cttgcccgct gctggacagg   2340
ggctcggctg ttgggcactg acaattccgt ggtgttgtcg gggaagctga cgtcctttcc   2400
atggctgctc gcctgtgttg ccacctggat tctgcgcggg acgtccttct gctacgtccc   2460
ttcggccctc aatccagcgg accttccttc ccgcggcctg ctgccggctc tgcggcctct   2520
tccgcgtctt cgccttcgcc ctcagacgag tcggatctcc ctttgggccg cctccccgcc   2580
tggaattaat tctgcagtcg agacctagaa aaacatggag caatcacaag tagcaataca   2640
gcagctacca atgctgattg tgcctggcta gaagcacaag aggaggagga ggtgggtttt   2700
tccagtcaca cctcaggacc tttaagacca atgacttaca aggcagctgt agatcttagc   2760
cactttttaa aagaaaagag gggactggaa gggctaattc actcccaacg aagacaagat   2820 ctgcttttg cctgtactgg gtctctctgg ttagaccaga tctgagcctg ggagctctct   2880
ggctaactag ggaacccact gcttaagcct caataaagct tgccttgagt gcttcaagta   2940
gtgtgtgccc gtctgttgtg tgactctggt aactagagat ccctcagacc cttttagtca   3000
gtgtggaaaa tctctagcag tagtagttca tgtcatctta ttattcagta tttataactt   3060
gcaaagaaat gaatatcaga gagtgagagg ctagcgtttt accgtcgacc tctagctaga   3120
gcttggcgta atcatggtca tagctgtttc ctgtgtgaaa ttgttatccg ctcacaattc   3180
cacacaacat acgagccgga agcataaagt gtaaagcctg gggtgcctaa tgagtgagct   3240
aactcacatt aattgcgttg cgctcactgc ccgctttcca gtcgggaaac ctgtcgtgcc   3300
agctgcatta atgaatcggc caacgcgcgg ggagaggcgg tttgcgtatt gggcgctctt   3360
ccgcttcctc gctcactgac tcgctgcgct cggtcgttcg gctgcggcga gcggtatcag   3420
```

```
ctcactcaaa ggcggtaata cggttatcca cagaatcagg ggataacgca ggaaagaaca   3480
tgtgagcaaa aggccagcaa aaggccagga accgtaaaaa ggccgcgttg ctggcgtttt   3540
tccataggct ccgcccccct gacgagcatc acaaaaatcg acgctcaagt cagaggtggc   3600
gaaacccgac aggactataa agataccagg cgtttccccc tggaagctcc ctcgtgcgct   3660
ctcctgttcc gaccctgccg cttaccggat acctgtccgc ctttctccct tcgggaagcg   3720
tggcgctttc tcatagctca cgctgtaggt atctcagttc ggtgtaggtc gttcgctcca   3780
agctgggctg tgtgcacgaa ccccccgttc agcccgaccg ctgcgcctta tccggtaact   3840
atcgtcttga gtccaacccg gtaagacacg acttatcgcc actggcagca gccactggta   3900
acaggattag cagagcgagg tatgtaggcg gtgctacaga gttcttgaag tggtggccta   3960
actacggcta cactagaaga acagtatttg gtatctgcgc tctgctgaag ccagttacct   4020
tcggaaaaag agttggtagc tcttgatccg gcaaacaaac caccgctggt agcggttttt   4080
ttgtttgcaa gcagcagatt acgcgcagaa aaaaaggatc tcaagaagat cctttgatct   4140
tttctacggg gtctgacgct cagtggaacg aaaactcacg ttaagggatt ttggtcatga   4200
gattatcaaa aaggatcttc acctagatcc ttttaaatta aaaatgaagt tttaaatcaa   4260
tctaaagtat atatgagtaa acttggtctg acagttacca atgcttaatc agtgaggcac   4320
ctatctcagc gatctgtcta tttcgttcat ccatagttgc ctgactcccc gtcgtgtaga   4380
taactacgat acgggagggc ttaccatctg gccccagtgc tgcaatgata ccgcgagacc   4440
cacgctcacc ggctccagat ttatcagcaa taaaccagcc agccggaagg gccgagcgca   4500
gaagtggtcc tgcaacttta tccgcctcca tccagtctat taattgttgc cgggaagcta   4560
gagtaagtag ttcgccagtt aatagtttgc gcaacgttgt tgccattgct acaggcatcg   4620
tggtgtcacg ctcgtcgttt ggtatggctt cattcagctc cggttcccaa cgatcaaggc   4680
gagttacatg atcccccatg ttgtgcaaaa aagcggttag ctccttcggt cctccgatcg   4740
ttgtcagaag taagttggcc gcagtgttat cactcatggt tatggcagca ctgcataatt   4800
ctcttactgt catgccatcc gtaagatgct tttctgtgac tggtgagtac tcaaccaagt   4860
cattctgaga atagtgtatg cggcgaccga gttgctcttg cccggcgtca atacgggata   4920
ataccgcgcc acatagcaga actttaaaag tgctcatcat tggaaaacgt tcttcggggc   4980
gaaaactctc aaggatctta ccgctgttga gatccagttc gatgtaaccc actcgtgcac   5040
ccaactgatc ttcagcatct tttactttca ccagcgtttc tgggtgagca aaaacaggaa   5100
ggcaaaatgc cgcaaaaaag ggaataaggg cgacacggaa atgttgaata ctcatactct   5160
tcctttttca atattattga agcatttatc agggttattg tctcatgagc ggatacatat   5220
ttgaatgtat ttagaaaaat aaacaaatag gggttccgcg cacatttccc cgaaaagtgc   5280
cacctgacgt cgacggatcg ggagatcaac ttgtttattg cagcttataa tggttacaaa   5340
taaagcaata gcatcacaaa tttcacaaat aaagcatttt tttcactgca ttctagttgt   5400
ggtttgtcca aactcatcaa tgtatcttat catgtctgga tcaactggat aactcaagct   5460
aaccaaaatc atcccaaact tcccacccca taccctatta ccactgccaa ttacctgtg   5520 ggcgcaatta accctcacta aagggaacaa aagctggagc tgcaagctta atgtagtctt   5580
atgcaatact cttgtagtct tgcaacatgg taacgatgag ttagcaacat gccttacaag   5640
gagagaaaaa gcaccgtgca tgccgattgg tggaagtaag gtggtacgat cgtgccttat   5700
taggaaggca acagacgggt ctgacatgga ttggacgaac cactgaattg ccgcattgca   5760
```

-continued

```
gagatattgt atttaagtgc ctagctcgat acataaacgg gtctctctgg ttagaccaga    5820
tctgagcctg ggagctctct ggctaactag ggaacccact gcttaagcct caataaagct    5880
tgccttgagt gcttcaagta gtgtgtgccc gtctgttgtg tgactctggt aactagagat    5940
ccctcagacc cttttagtca gtgtggaaaa tctctagcag tggcgcccga acagggactt    6000
gaaagcgaaa gggaaaccag aggagctctc tcgacgcagg actcggcttg ctgaagcgcg    6060
cacggcaaga ggcgaggggc ggcgactggt gagtacgcca aaaattttga ctagcggagg    6120
ctagaaggag agagatgggt gcgagagcgt cagtattaag cgggggagaa ttagatcgcg    6180
atgggaaaaa attcggttaa ggccaggggg aaagaaaaaa tataaattaa aacatatagt    6240
atgggcaagc agggagctag aacgattcgc agttaatcct ggcctgttag aaacatcaga    6300
aggctgtaga caaatactgg gacagctaca accatccctt cagacaggat cagaagaact    6360
tagatcatta tataatacag tagcaaccct ctattgtgtg catcaaagga tagagataaa    6420
agacaccaag gaagctttag acaagataga ggaagagcaa aacaaaagta agaccaccgc    6480
acagcaagcg gccggccgct gatcttcaga cctggaggag gagatatgag ggacaattaa    6540
ttggagaagt gaattatata aatataaagt agtaaaaatt gaaccattag gagtagcacc    6600
caccaaggca aagagaagag tggtgcagag agaaaaaaga gcagtgggaa taggagcttt    6660
gttccttggg ttcttgggag cagcaggaag cactatgggc gcagcgtcaa tgacgctgac    6720
ggtacaggcc agacaattat tgtctggtat agtgcagcag cagaacaatt tgctgagggc    6780
tattgaggcg caacagcatc tgttgcaact cacagtctgg ggcatcaagc agctccaggc    6840
aagaatcctg gctgtggaaa gatacctaaa ggatcaacag ctcctgggga tttgggttg     6900 ctctggaaaa ctcatttgca ccactgctgt gccttggaat gctagttgga gtaataaatc    6960
tctggaacag atttggaatc acacgacctg gatggagtgg gacagagaaa ttaacaatta    7020
cacaagctta atacactcct taattgaaga atcgcaaaac cagcaagaaa agaatgaaca    7080
agaattattg gaattagata aatgggcaag tttgtggaat tggtttaaca taacaaattg    7140
gctgtggtat ataaaattat tcataatgat agtaggaggc ttggtaggtt taagaatagt    7200
ttttgctgta ctttctatag tgaatagagt taggcaggga tattcaccat tatcgtttca    7260
gacccacctc ccaaccccga ggggacccga caggcccgaa ggaatagaag aagaaggtgg    7320
agagagagac agagacagat ccattcgatt agtgaacgga tctcgacggt atcgcctta     7380 aaagaaaagg ggggattggg gggtacagtg cagggaaag aatagtagac ataatagcaa      7440
cagacataca aactaaagaa ctacaaaaac aaattacaaa aattcaaaat tttcgggttt    7500
attacaggga cagcagagat ccagtttatc taatacgact cactataggg agagagagag    7560
aattaccctc actaaaggga ggagaagcat gtcgacgaat tcctaatacg actcactata    7620
ggatatcagt ctagggaaag tcattcagtg gatgtgatct tggctcacag gggacgatgt    7680
caagctcgtc ctctcctcgt ttcaatctgt atgctgatgg tcgctctgcc tccaccattg    7740
aggaacaggc caagacattt ttggacaagt tgtcaaacca gaccgaagac ctgttctatc    7800
aaagttcact tgcttcttgg aattataaca ccaatattac tgaagagaat gtccaaaaca    7860
tgaataatgc tggggacaaa tggtctgcct ttttaaagga acagtccaca cttgcccaaa    7920
tgtatccact acaagaaatt cagaatctca cagtcaagct tcagctgcag gctcttcagc    7980
aaaatgggtc ttagtagctc gagctgtgga atgtgtgtca gttagggtgt ggaaagtccc    8040
caggctcccc agcaggcaga agtatgcaaa gcatgcatct caattagtca gcaaccaggt    8100
gtggaaagtc cccaggctcc ccagcaggca gaagtatgca aagcatgcat ctcaattagt    8160
```

-continued

```
cagcaaccat agtcccgccc ctaactccgc ccatcccgcc cctaactccg cccagttccg    8220
cccattctcc gccccatggc tgactaattt tttttattta tgcagaggcc gaggccgcct    8280
ctgcctctga gctattccag aagtagtgag gaggcttttt tggaggccta ggcttttgca    8340
aaaagctccc gggagcttgt atatccattt                                     8370

<210> SEQ ID NO 52
<211> LENGTH: 56
<212> TYPE: DNA
<213> ORGANISM: Artificial Sequence
<220> FEATURE:
<223> OTHER INFORMATION: Synthesized

<400> SEQUENCE: 52
ccctcactaa agggaggaga agcatgtcga cgaattccta atacgactca ctatag       56

<210> SEQ ID NO 53
<211> LENGTH: 55
<212> TYPE: DNA
<213> ORGANISM: Artificial Sequence
<220> FEATURE:
<223> OTHER INFORMATION: Synthesized

<400> SEQUENCE: 53
gtggcaacgg cagtacagac aacgatatcc tatagtgagt cgtattagga attcg        55

<210> SEQ ID NO 54
<211> LENGTH: 59
<212> TYPE: DNA
<213> ORGANISM: Artificial Sequence
<220> FEATURE:
<223> OTHER INFORMATION: Synthesized

<400> SEQUENCE: 54
tgtactgccg ttgccacata gatcatccaa atcctaaagg attttgtgac ttaaaaggt    59

<210> SEQ ID NO 55
<211> LENGTH: 58
<212> TYPE: DNA
<213> ORGANISM: Artificial Sequence
<220> FEATURE:
<223> OTHER INFORMATION: Synthesized

<400> SEQUENCE: 55
caagttgtag gtatttgtac atacttacct tttaagtcac aaaatccttt aggatttg     58

<210> SEQ ID NO 56
<211> LENGTH: 59
<212> TYPE: DNA
<213> ORGANISM: Artificial Sequence
<220> FEATURE:
<223> OTHER INFORMATION: Synthesized

<400> SEQUENCE: 56
aggtaagtat gtacaaatac ctacaacttg tgctaatgac cctgtgggtt ttacactta    59

<210> SEQ ID NO 57
<211> LENGTH: 59
<212> TYPE: DNA
<213> ORGANISM: Artificial Sequence
<220> FEATURE:
<223> OTHER INFORMATION: Synthesized

<400> SEQUENCE: 57
```
aatgaccctg tgggtttttac acttaaaatg cagttccgag ctcactcgac tctctgatc          59

<210> SEQ ID NO 58
<211> LENGTH: 59
<212> TYPE: DNA
<213> ORGANISM: Artificial Sequence
<220> FEATURE:
<223> OTHER INFORMATION: Synthesized

<400> SEQUENCE: 58
ccgagctcac tcgactctct gatcagacga tggtttttact tatcaccaaa tccgcgtag          59

<210> SEQ ID NO 59
<211> LENGTH: 57
<212> TYPE: DNA
<213> ORGANISM: Artificial Sequence
<220> FEATURE:
<223> OTHER INFORMATION: Synthesized

<400> SEQUENCE: 59
acgattgtgc atcagctgac tacgatctgc ctacgcggat ttggtgataa gtaaaac            57

<210> SEQ ID NO 60
<211> LENGTH: 59
<212> TYPE: DNA
<213> ORGANISM: Artificial Sequence
<220> FEATURE:
<223> OTHER INFORMATION: Synthesized

<400> SEQUENCE: 60
gtagtcagct gatgcacaat cgtttttaaa cgggtttgcg gtgtaagtgc agcccgtct          59

<210> SEQ ID NO 61
<211> LENGTH: 59
<212> TYPE: DNA
<213> ORGANISM: Artificial Sequence
<220> FEATURE:
<223> OTHER INFORMATION: Synthesized

<400> SEQUENCE: 61
cacattccac agctcgagtg cctgtgccgc acggtgtaag acgggctgca cttacaccg          59

<210> SEQ ID NO 62
<211> LENGTH: 21
<212> TYPE: DNA
<213> ORGANISM: Artificial Sequence
<220> FEATURE:
<223> OTHER INFORMATION: Synthesized

<400> SEQUENCE: 62
ccctgtgggt tttacactta a                                                    21

<210> SEQ ID NO 63
<211> LENGTH: 19
<212> TYPE: DNA
<213> ORGANISM: Artificial Sequence
<220> FEATURE:
<223> OTHER INFORMATION: Synthesized

<400> SEQUENCE: 63
acgattgtgc atcagctga                                                       19

<210> SEQ ID NO 64
<211> LENGTH: 28
<212> TYPE: DNA
<213> ORGANISM: Artificial Sequence

```
<220> FEATURE:
<223> OTHER INFORMATION: Synthesized
<220> FEATURE:
<221> NAME/KEY: misc_feature
<222> LOCATION: (1)..(1)
<223> OTHER INFORMATION: 5'-FAM
<220> FEATURE:
<221> NAME/KEY: misc_feature
<222> LOCATION: (28)..(28)
<223> OTHER INFORMATION: 3'-BHQ1

<400> SEQUENCE: 64
ccgtctgcgg tatgtggaaa ggttatgg                                       28

<210> SEQ ID NO 65
<211> LENGTH: 22
<212> TYPE: DNA
<213> ORGANISM: Artificial Sequence
<220> FEATURE:
<223> OTHER INFORMATION: Synthesized

<400> SEQUENCE: 65
ggggaacttc tcctgctaga at                                             22

<210> SEQ ID NO 66
<211> LENGTH: 22
<212> TYPE: DNA
<213> ORGANISM: Artificial Sequence
<220> FEATURE:
<223> OTHER INFORMATION: Synthesized

<400> SEQUENCE: 66
cagacatttt gctctcaagc tg                                             22

<210> SEQ ID NO 67
<211> LENGTH: 20
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: 5'-FAM
<220> FEATURE:
<221> NAME/KEY: misc_feature
<222> LOCATION: (20)..(20)
<223> OTHER INFORMATION: 3'-BHQ1

<400> SEQUENCE: 67
ttgctgctgc ttgacagatt                                                20

<210> SEQ ID NO 68
<211> LENGTH: 26
<212> TYPE: DNA
<213> ORGANISM: Artificial Sequence
<220> FEATURE:
<223> OTHER INFORMATION: Synthesized

<400> SEQUENCE: 68
acaggtacgt taatagttaa tagcgt                                         26

<210> SEQ ID NO 69
<211> LENGTH: 22
<212> TYPE: DNA
<213> ORGANISM: Artificial Sequence
<220> FEATURE:
<223> OTHER INFORMATION: Synthesized
```

<400> SEQUENCE: 69
atattgcagc agtacgcaca ca                                                  22

<210> SEQ ID NO 70
<211> LENGTH: 26
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: 5'-FAM
<220> FEATURE:
<221> NAME/KEY: misc_feature
<222> LOCATION: (27)..(27)
<223> OTHER INFORMATION: 3'-BHQ1

<400> SEQUENCE: 70
acactagcca tccttactgc gcttcg                                              26

<210> SEQ ID NO 71
<211> LENGTH: 21
<212> TYPE: DNA
<213> ORGANISM: Artificial Sequence
<220> FEATURE:
<223> OTHER INFORMATION: Synthesized

<400> SEQUENCE: 71
ccagatccat caaaaccaag c                                                   21

<210> SEQ ID NO 72
<211> LENGTH: 21
<212> TYPE: DNA
<213> ORGANISM: Artificial Sequence
<220> FEATURE:
<223> OTHER INFORMATION: Synthesized

<400> SEQUENCE: 72
tgcacaaatg aggtctctag c                                                   21

<210> SEQ ID NO 73
<211> LENGTH: 23
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: 5'-FAM
<220> FEATURE:
<221> NAME/KEY: misc_feature
<222> LOCATION: (23)..(23)
<223> OTHER INFORMATION: 3'-BHQ1

<400> SEQUENCE: 73
agtgacactt gcagatgctg gct                                                 23

<210> SEQ ID NO 74
<211> LENGTH: 22
<212> TYPE: DNA
<213> ORGANISM: Artificial Sequence
<220> FEATURE:
<223> OTHER INFORMATION: Synthesized

<400> SEQUENCE: 74
ggggaacttc tcctgctaga at                                                  22

```
<210> SEQ ID NO 75
<211> LENGTH: 22
<212> TYPE: DNA
<213> ORGANISM: Artificial Sequence
<220> FEATURE:
<223> OTHER INFORMATION: Synthesized

<400> SEQUENCE: 75
cagacatttt gctctcaagc tg                                              22

<210> SEQ ID NO 76
<211> LENGTH: 21
<212> TYPE: DNA
<213> ORGANISM: Artificial Sequence
<220> FEATURE:
<223> OTHER INFORMATION: Synthesized

<400> SEQUENCE: 76
ccagatccat caaaaccaag c                                               21

<210> SEQ ID NO 77
<211> LENGTH: 21
<212> TYPE: DNA
<213> ORGANISM: Artificial Sequence
<220> FEATURE:
<223> OTHER INFORMATION: Synthesized

<400> SEQUENCE: 77
tgcacaaatg aggtctctag c                                               21

<210> SEQ ID NO 78
<211> LENGTH: 19
<212> TYPE: DNA
<213> ORGANISM: Artificial Sequence
<220> FEATURE:
<223> OTHER INFORMATION: Synthesized

<400> SEQUENCE: 78
cctgccacac tcagtcccc                                                  19

<210> SEQ ID NO 79
<211> LENGTH: 19
<212> TYPE: DNA
<213> ORGANISM: Artificial Sequence
<220> FEATURE:
<223> OTHER INFORMATION: Synthesized

<400> SEQUENCE: 79
gacaaggtgc ggctcccta                                                  19

<210> SEQ ID NO 80
<211> LENGTH: 20
<212> TYPE: DNA
<213> ORGANISM: Artificial Sequence
<220> FEATURE:
<223> OTHER INFORMATION: Synthesized

<400> SEQUENCE: 80
ttgctgctgc ttgacagatt                                                 20

<210> SEQ ID NO 81
<211> LENGTH: 23
<212> TYPE: DNA
<213> ORGANISM: Artificial Sequence
<220> FEATURE:
```

-continued

<223> OTHER INFORMATION: Synthesized

<400> SEQUENCE: 81
agtgacactt gcagatgctg gct                                                    23

<210> SEQ ID NO 82
<211> LENGTH: 29
<212> TYPE: DNA
<213> ORGANISM: Artificial Sequence
<220> FEATURE:
<223> OTHER INFORMATION: Synthesized

<400> SEQUENCE: 82
cacactgaat ctcccctcct cacagttgc                                              29

<210> SEQ ID NO 83
<211> LENGTH: 25
<212> TYPE: DNA
<213> ORGANISM: Artificial Sequence
<220> FEATURE:
<223> OTHER INFORMATION: Synthesized

<400> SEQUENCE: 83
caccgaggat gcacagctcg ctcta                                                  25

<210> SEQ ID NO 84
<211> LENGTH: 21
<212> TYPE: DNA
<213> ORGANISM: Artificial Sequence
<220> FEATURE:
<223> OTHER INFORMATION: Synthesized

<400> SEQUENCE: 84
caagctcttc ctggctcctt c                                                      21

<210> SEQ ID NO 85
<211> LENGTH: 20
<212> TYPE: DNA
<213> ORGANISM: Artificial Sequence
<220> FEATURE:
<223> OTHER INFORMATION: Synthesized

<400> SEQUENCE: 85
ggtcttcggc ttcgtggtta                                                        20

<210> SEQ ID NO 86
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: 5'-HEX
<220> FEATURE:
<221> NAME/KEY: misc_feature
<222> LOCATION: (1)..(1)
<223> OTHER INFORMATION: 5'-HEX
<220> FEATURE:
<221> NAME/KEY: misc_feature
<222> LOCATION: (27)..(27)
<223> OTHER INFORMATION: 3'-BHQ1

<400> SEQUENCE: 86
agccttgttg ctgtaactgc tgctcag                                                27

-continued

```
<210> SEQ ID NO 87
<211> LENGTH: 21
<212> TYPE: DNA
<213> ORGANISM: Artificial Sequence
<220> FEATURE:
<223> OTHER INFORMATION: Synthesized

<400> SEQUENCE: 87
caagctcgtc ctctcctcgt t                                              21

<210> SEQ ID NO 88
<211> LENGTH: 20
<212> TYPE: DNA
<213> ORGANISM: Artificial Sequence
<220> FEATURE:
<223> OTHER INFORMATION: Synthesized

<400> SEQUENCE: 88
ggtcttcggt ctggtttgac                                               20

<210> SEQ ID NO 89
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: 5-ROX
<220> FEATURE:
<221> NAME/KEY: misc_feature
<222> LOCATION: (27)..(27)
<223> OTHER INFORMATION: 3-BHQ2

<400> SEQUENCE: 89
aatctgtatg ctgatggtcg ctctgcc                                       27
```

SPIKE-IN REFERENCE STANDARD FOR USE IN DETECTING SAMPLE TARGET FROM DNA OR RNA ORGANISM

SEQUENCE LISTING

The instant application contains a Sequence Listing which has been submitted electronically in ASCII format and is hereby incorporated by reference in its entirety. The ASCII copy, created on Jun. 8, 2023, is named 0259-FG01US1_ST25 and is 60,133 bytes in size.

FIELD OF THE INVENTION

The present invention belongs to the field of diagnosis. In particular, the present invention relates to a recombinant viral particle for quantitative detection of nucleic acid target in a sample and uses thereof.

BACKGROUND OF THE INVENTION

Infection of the human body by coronaviruses can lead to pneumonia, such as COVID-19. The rapid nucleic acid detection of a coronavirus has become one of the important technologies for controlling the spread of the virus, diagnosis, treatment and prevention of the disease caused by the virus. Since December 2019, a new coronavirus 2019-nCoV (which was named as "SARS-CoV-2" by the International Committee on Taxonomy of Viruses on Feb. 12, 2020) has infected the human body and produced a new type of coronavirus pneumonia epidemic (wherein the pneumonia caused by the new coronavirus infection was named "COVID-19" by the World Health Organization), and the discovery of 2019-nCoV carriers, susceptible populations, morbidity, treatment rates and mortality rates has become a very concerned and sensitive issue for governments and people at home and abroad. The rapid nucleic acid detection of 2019-nCoV has become one of the important technologies for controlling the spread of the virus, and the diagnosis, treatment and prevention of the disease.

At present, kits have been developed for 2019-nCoV at home and abroad. On Mar. 6, 2020, the National Medical Products Administration (NMPA) approved a total of 10 kinds of nucleic acid detection reagents and 5 kinds of antibody detection reagents for 2019-nCoV (FIG. 1). However, due to the lack of positive controls similar to 2019-nCoV that can be used for 2019-nCoV nucleic acid detection kits and related equipment, the accuracy of detection results (positive and negative) obtained by these nucleic acid detection kits and related equipment cannot be well determined. Even if there is a false negative, it is not reliable, and the number of virus particles per unit volume of the sample cannot be measured (such as 500 virus particles/ml). On Feb. 12, 2020, the US CDC said that the detection kit developed by it was confirmed to be defective and was subsequently withdrawn urgently. A defective component in the batch of detection kits has left numerous public health labs across the country unable to use them.

In view of this, there is an urgent need for reference standards that can accurately reflect the detection accuracy and quantify 2019-nCoV to confirm false positives, and then quantify the 2019-nCoV so as to better observe the dynamic analysis of coronavirus RNA and be used for judgment of patient treatment standards.

In addition, reference standards that can accurately reflect the detection accuracy and quantify 2019-nCoV can also be used for new drug development experiments, such as evaluating the effects and quality of a drug through the viral load in different periods (Zou, et al. 2020, Kim, et al. 2020, Pan, et al. 2020).

The polymerase chain reaction (PCR) has been widely used as a diagnostic tool since the early 1990s. The use of polymerase chain reaction has revolutionized the diagnostic detection of microorganisms by providing rapid, specific and sensitive detection of microbial nucleic acids in various samples. Initially, false positive results, which were the result of contamination in previously generated amplicon reactions, were a major concern for those using this new technology. Measures were taken to avoid contamination of pre-amplified nucleic acids, and substantial improvements were achieved with the introduction of real-time polymerase chain reaction. This is because the real-time PCR is a closed tube system and does not require post-PCR analysis of amplicons; it is still considered a major source of contamination and false positive results when this technique is applied. In addition, there is an increasing emphasis on minimizing the impact of false negative results; that is, ensuring that negative results truly represent the absence of PCR diagnosis targets. This is because false negative results can result from failure of one of the test steps (nucleic acid extraction, reverse transcription reaction, polymerase chain reaction set-up or amplification). The first method to control false negative results is to add exogenous nucleic acids with a different sequence to the target nucleic acid to be detected in the polymerase chain reaction. Spike-in internal control of the reaction system is usually a plasmid DNA. The presence of any PCR amplification-inhibiting substances in the sample will reduce or completely inhibit the amplification of nucleic acids. Based on this principle, published literature has disclosed the use of single and multiple internal quality controls of plasmids for the diagnosis of several pathogens (Stocher et al. 2003, Dingle et al. 2004, Hymas et al. 2005, Maaroufi et al. 2006).

However, this method of spike-in internal control can only be used to assess false negatives caused by the amplification step. In the case of detection of viral nucleic acid, it is also necessary to control the various steps before amplification, such as collecting viral particles from plasma and extracting viral nucleic acid, using throat swabs to collect SARS-COV-2 and storing the SARS-COV-2 in a storage solution, extracting viral RNAs within a certain time and then performing RT-PCR nucleic acid detection. New approaches are needed to overcome the above limitations. Initially, an exogenous nucleic acid is added before nucleic acid extraction to assess the efficiency of nucleic acid extraction, but the loss of viral particles during sample collection cannot be properly assessed. Therefore, the ideal controls (standards) should be a nucleic acid that can be protected, which needs to be similar in structure to the virus particle to be tested and exist in the whole process of RT-PCR viral nucleic acid detection. In addition, the construction of protected DNA or RNA will protect the nucleic acid from degradation by nucleases or hydrolase after long-term storage, which is especially important if a viral RNA is used as a control.

Viruses or pseudovirus particles, containing the same kind of nucleic acid (DNA or RNA) as the target nucleic acid to be tested and being structurally stable, are designed to undergo the same steps as the pathogen to be tested, and have been used in the detection and analysis of viral targets (Cleland et al. 1999, Garson et al. 2005, Clancy et al. 2008). For the safety of humans and animals, scientists preferentially choose non-pathogenic viruses as the basic backbones for modification, which can be incorporated into the internal control of the sample to be tested (Dreier et al. 2005, Gerriets et al. 2008, Ninove et al. 2011).

Before the present invention, two types of exogenous internal controls were used in real-time fluorescent PCR reaction analysis. A competitive spike-in internal control has the same primer sequences as the target of the sample to be tested, and uses the same primer pair as the target to be tested in the same PCR reaction, but the probe sequence of the spike-in internal control and that of the target to be tested are different. A non-competitive internal control has completely different base-percentage composition and sequence from the target of the sample to be tested. The competitive internal control can mimic the amplification kinetics of the target sequence; however, it will compete with the target sequence in PCR reaction systems with low-concentration of target to be tested. Non-competitive spike-in internal controls that are completely different from the target sequence can be designed and prepared for use with several target sequences to be tested; amplification of non-competitive quality controls generally cannot reflect the amplification kinetics of the target sequence to be tested (Rosenstraus et al. 1998, Hoorfar et al. 2004, Sharma et al. 2014). Therefore, it is necessary to select the competitive and non-competitive internal controls according to different detection requirements.

In the published literature, bovine diarrhea virus (Cleland et al. 1999), canine distemper virus (Clancy et al. 2008), murine cytomegalovirus (Garson et al. 2005), and T4 and MS2 phages (Dreier et al. al. 2005, Rolfe et al. 2007, Gerriets et al. 2008, Ninove et al. 2011) were used for the preparation of non-competitive internal controls to detect various DNA and RNA viruses including hepatitis C virus (HCV).

Competitive internal control mock pseudoviruses based on bacteriophage λ and Qβ as backbones have been used for the detection of various viruses (Stocher et al. 2003, Stocher & Berg 2004, Villanova et al. 2007, Meng et al. 2009); competitive pseudoviral internal controls for the target to be tested contain pathogen-specific target nucleic acid sequences and the first commercial competitive internal control called "armored RNA" prepared from bacteriophage lambda and viral coat proteins (such as MS2 coat protein) (Pasloske et al. 1998). There are also reports of the use of multiple competitive internal controls (WalkerPeach et al. 1999, Drosten et al. 2001, Beld et al. 2004, Cheng et al. 2006, Zhao et al. 2007, Wei et al. 2008, Meng et al. 2009, Zhan et al. 2009, Felder & Wölfel 2014, Sharma et al. 2014). Zambenedetti et al. reported that based on MS2 bacteriophage, a mock virus as competitive internal control was constructed using *Escherichia coli* as a host, and pseudoviruses as various competitive internal controls were tested for use in monitoring the steps of extraction, reverse transcription, amplification and detection in the process of diagnosis of hepatitis C virus. The difference between the mock virus and the target sequence of the virus to be tested is limited to the difference in the arrangement of 14 bases in the 21 bases of the fluorescent probe-binding sequence (Zambenedetti et al. 2017). This mock virus is designed as a competitive internal control and does not address the issues of competitive internal control design reported by Gibson more than two decades ago (Gibson et al. 1996). In the real-time quantitative PCR or RT-PCR reaction system, when the number of mock virus particles containing the competitive internal control and the number of target virus particles of the sample to be tested are too different, the more ones will reduce the amplification efficiency of the less ones, or even completely inhibit the amplification of less ones. The inhibitory mechanism is complex and includes kinetic changes caused by changes in dNTP, divalent $Mg2+$, enzymatic activity, and phosphorylation (PPi) of the reaction system during PCR or RT-PCR.

The aim of the present disclosure is to solve the above defects of the competitive internal control, wherein the spike-in internal control that has been accurately quantified is used to allow the qualitative detection of the target more accurate, and the copy number of the target to be tested (virus, DNA or RNA) in the sample can be calculated more accurately according to the copy number of the mock virus of spike-in internal control or the molecule number (copy number) of DNA, RNA, and cDNA spike-in internal control derived therefrom.

REFERENCES

Beld M, Minnaar R, Weel J, Sol C, Damen M, Van der Avoort H, et al. Highly sensitive assay for detection of enterovirus in clinical specimens by reverse transcription-PCR with an armored RNA internal control. J Clin Microbiol. 2004; 42(7): 3059-64.

Cheng Y, Niu J, Zhang Y, Huang J, Li Q. Preparation of His-tagged armored RNA phage particles as a control for real-time reverse transcription-PCR detection of severe acute respiratory syndrome coronavirus. J Clin Microbiol. 2006; 44(10): 3557-61.

Clancy A, Crowley B, Niesters H, Herra C. The development of a qualitative real-time RT-PCR assay for the detection of hepatitis C virus. Eur J Clin Microbiol Infect Dis. 2008; 27(12): 1177-82.

Cleland A, Nettleton P, Jarvis L, Simmonds P. Use of bovine viral diarrhea virus as an internal control for amplification of hepatitis C virus. Vox Sang. 1999; 76(3): 170-4.

Dingle K E, Crook D, Jeffery K. Stable and noncompetitive RNA internal control for routine clinical diagnostic reverse transcription-PCR. J Clin Microbiol. 2004; 42(3): 1003-11.

Dreier J, Störmer M, Kleesiek K. Use of bacteriophage MS2 as an internal control in viral reverse transcription-PCR assays. J Clin Microbiol. 2005; 43(9): 4551-7.

Drosten C, Seifried E, Roth W K. TaqMan 5'-nuclease human immunodeficiency virus type 1 PCR assay with phage-packaged competitive internal control for high-throughput blood donor screening. J Clin Microbiol. 2001; 39(12): 4302-8.

Felder E, Wölfel R. Development of a versatile and stable internal control system for RT-qPCR assays. J Virol Methods. 2014; 208: 33-40.

Garson J A, Grant P R, Ayliffe U, Ferns R B, Tedder R S. Real-time PCR quantitation of hepatitis B virus DNA using automated sample preparation and murine cytomegalovirus internal control. J Virol Methods. 2005; 126(1-2): 207-13.

Gerriets J E, Greiner T C, Gebhart C L. Implementation of a T4 extraction control for molecular assays of cerebrospinal fluid and stool specimens. J Mol Diagn. 2008; 10(1): 28-32.

Hoorfar J, Malorny B, Abdulmawjood A, Cook N, Wagner M, Fach P. Practical considerations in design of internal amplification controls for diagnostic PCR assays. J Clin Microbiol. 2004; 42(5): 1863-8.

Hymas W, Stevenson J, Taggart E W, Hillyard D. Use of lyophilized standards for the calibration of a newly developed real time PCR assay for human herpes type six (HHV6) variants A and B. J Virol Methods. 2005; 128 (1-2): 43-50.

Jin Yong Kim, Jae-Hoon Ko, Yeonjae Kim et al, (2020) Viral Load Kinetics of SARS-CoV-2 Infection in First Two Patients in Korea. J Korean Med Sci, 35(7):e86.

Lirong Zou, Feng Ruan, Mingxing Huang et al, (2020) SARS-CoV-2 Viral Load in Upper Respiratory Specimens of Infected Patients. N ENGL JMED, 1-3.

Maaroufi Y, de Bruyne J M, Duchateau V, Scheen R, Crokaert F. Development of a multiple internal control for clinical diagnostic real-time amplification assays. FEMS Immunol Med Microbiol. 2006; 48(2): 183-91.

Meng S, Zhan S, Li J. Nuclease-resistant double-stranded DNA controls or standards for hepatitis B virus nucleic acid amplification assays. Virol J. 2009; 6(226): 1-7.

Miriam Ribas Zambenedetti, Daniela Parada Pavoni, Andreia Cristine Dallabona, Alejandro Correa Dominguez, Celina de Oliweira poersch, Stenio Perdigao Fragoso, Marco Aurelio Krieger, ea al. Internal control for real-time polymerase chain reaction based on MS2 bacteriophage for RNA viruses diagnostics. Mem inst Oswaldo Cruz. 2017; 112(5):339-347.

Ninove L, Nougairede A, Gazin C, Thirion L, Delogu I, Zandotti C, et al. RNA and DNA bacteriophages as molecular diagnosis controls in clinical virology: a comprehensive study of more than 45,000 routine PCR tests. PLoS ONE. 2011; 6(2): 1-7.

Pasloske B L, Walkerpeach C R, Obermoeller R D, Winkler M, DuBois D B. Armored RNA technology for production of ribonuclease-resistant viral RNA controls and standards. J Clin Microbiol. 1998; 36(12): 3590-4.

Rolfe K J, Parmar S, Mururi D, Wreghitt T G, Jalal H, Zhang H, et al. An internally controlled, one-step, real-time RT-PCR assay for norovirus detection and genogrouping. J Clin Virol. 2007; 39(4): 318-21.

Rosenstraus M, Wang Z, Chang S Y, DeBonville D, Spadoro J P. An internal control for routine diagnostic PCR: design, properties, and effect on clinical performance. J Clin Microbiol. 1998; 36(1): 191-7.

Sharma N, Chand D, Shukla A, Singh M, Govil R K, Bihari B, et al. Internal controls for the quality assessment of polymerase chain reaction methods for the diagnosis of infectious & autoimmune disease. Sch J App Med Sci. 2014; 2(1D): 485-8.

Stöcher M, Berg J. Internal control DNA for PCR assays introduced into lambda phage particles exhibits nuclease resistance. Clin Chem. 2004; 50(11): 2163-6.

Stöcher M, Leb V, Berg J. A convenient approach to the generation of multiple internal control DNA for a panel of real-time PCR assays. J Virol Methods. 2003; 108(1): 1-8.

Ursula E. M, Gibson, Christian A. Heid, and P. Mickey Williams, et al. A Novel Method for Real Time Quantitative RT-PCR. Genome Res. 1996; 6: 995-1001.

Villanova G V, Gardiol D, Taborda M A, Reggiardo V, Tanno H, Rivadeneira E D, et al. Strategic approach to produce low-cost, efficient, and stable competitive internal controls for detection of RNA viruses by use of reverse transcription-PCR. J Clin Microbiol. 2007; 45(11): 3555-63.

WalkerPeach C R, Winkler M, DuBois D B, Pasloske B L. Ribonuclease-resistant RNA controls (Armored RNA) for reverse transcription-PCR, branched DNA, and genotyping assays for hepatitis C virus. Clin Chem. 1999; 45(12): 2079-85.

Wei Y, Yang C, Wei B, Huang J, Wang L, Meng S, et al. RNaseresistant virus-like particles containing long chimeric RNA sequences produced by two-plasmid coexpression system. J Clin Microbiol. 2008; 46(5): 1734-40.

Yang Pan, Daitao Zhang, Peng Yang. (2020) Viral load of SARS-COV-2 in clinical samples. Lancet Infect Dis 20 (4): 411-412 (2020).

Zhan S, Li J, Xu R, Wang L, Zhang K, Zhang R. Armored long RNA controls or standards for branched DNA assay for detection of human immunodeficiency virus type 1. J Clin Microbiol. 2009; 47(8): 2571-6.

Zhao L, Ma Y, Zhao S, Yang N. Armored RNA as positive control and standard for quantitative reverse transcription-polymerase chain reaction assay for rubella virus. Arch Virol. 2007; 152(1): 219-24.

SUMMARY OF THE INVENTION

The present invention relates to for example a recombinant viral particle for quantitative detection of nucleic acid target in a sample. Specifically, the present invention relates to a positive reference for spiking in collected sample for use in qualitatively and quantitatively detecting SARS-CoV-2 RNA and uses thereof.

Specifically, the present disclosure relates to the following aspects:

1. A mock virus vector, wherein a viral (lentiviral or adenoviral is preferable) backbone is used as the vector; the lentiviral backbone contains one or more quantitative detection nucleic acid fragments and the coding gene of a fluorescent protein for tracking, the quantitative detection nucleic acid fragments has the same length as the nucleic acid target sequence of a test sample, and has the same percentage of base composition as the nucleic acid target sequence of the test sample; wherein the 5' end sequence A and 3' end sequence B of the quantitative detection nucleic acid fragment are the same as or different from the corresponding 5' end sequence A' and 3' end sequence B' of the nucleic acid target sequence of the test sample; the sequence A consists of a 5' end primer sequence for amplifying the nucleic acid target sequence of the test sample and two bases of the nucleic acid target sequence of the test sample directly downstream of the 5' end primer sequence; and the sequence B consists of a 3' end primer sequence for amplifying the nucleic acid target sequence of the test sample and two bases of the nucleic acid target sequence of the test sample directly upstream of the 3' end primer sequence; the base sequence between the 5' end sequence A and 3' end sequence B of the quantitative detection nucleic acid fragment and the base sequence between the 5'end sequence A' and 3' end sequence B' of the nucleic acid target sequence of the test sample are completely different (preferably, there is no subsequences having more than 3 contiguous bases, for example, 4, 5, 6, or 7 contiguous bases, preferably, 8-30 contiguous bases between the two base sequences after their alignment, are identical);

preferably, the one or more quantitative detection nucleic acid fragments and the fluorescent proteins are connected by means of linkers; more preferably, the length of the linkers is 6-800 bp, preferably, 20-800 bp or 6-200 bp, preferably, the linkers contain transcriptional control elements, including but not limited to a CMV (promoter), an IRES (ribosome binding site).

2. The mock virus vector of item 1, wherein the nucleic acid target sequence of test sample is derived from an organism, and the organism is selected from a virus, a bacterium, a fungus, a plant, an animal (including a lower animal and a higher animal, preferably, the lower animal includes but not limited to nematodes and drosophila, and the higher animal including but not limited to a salmon, a zebra fish, and a mammal, and more preferably, the mammal includes but not limited to a human, a gorilla, a monkey, and a mouse).

3. The mock virus vector of item 2, wherein the virus is selected from the group consisting of DNA viruses (such as herpes simplex virus, hepatitis A virus, hepatitis B virus, human papilloma virus (HPV), and adenovirus) or RNA viruses (such as hepatitis C virus, human immunodeficiency virus, coronavirus, influenza virus such as avian influenza virus or swine influenza virus); the bacterium includes but not limited to one from tuberculosis, gonorrhea, anthracnose, syphilis, plague, trachoma, etc., and the fungus is selected from but not limited to the group consisting of mould, yeast, truffles and other mushrooms well-known to humans;

preferably, the coronavirus is selected from the group consisting of SARS virus, MERS virus, and SARS-CoV-2 virus.

4. The mock virus vector of item 3, wherein the length of the quantitative detection nucleic acid fragment is 80 bp-60 kb, preferably, 80 bp-19.5 kb, 80 bp-17.5 kb, 80 bp-1.5 kb, 80 bp-1 kb, 80 bp-500 bp, more preferably, 80 bp-200 bp, and the total length of the linker sequence between the quantitative detection nucleic acid fragments is not more than 8.5 kb, 8 kb or 7 kb.

5. The mock virus vector of any one of items 1-4, wherein the lentiviral vector is a lentivirus vector (preferably, pEZ-Lv201) or an FIV virus vector.

6. The mock virus vector of any one of items 1-5, wherein the lentiviral vector includes but not limited to second-generation or third-generation lentiviral vectors.

7. The mock virus vector of item 5 or 6, wherein, when the nucleic acid of test sample derives from SARS-COV-2, the nucleic acid target sequence of test sample is at least two coding genes selected from the following coding genes group consisting of: full length Orf1ab coding gene or fragment thereof, full length S protein coding gene or fragment thereof, full length E protein coding gene or fragment thereof, and full length N protein coding gene or fragment thereof.

8. The mock virus vector of item 7, wherein the quantitative detection nucleic acid fragment is one or more selected from the group consisting of:

a detection target sequence 1 (corresponding to the fragment of Orf1ab coding gene of test sample) comprises or at least consists of sequences selected from SEQ ID NO: 1 to SEQ ID NO: 2 or a combination thereof;

a detection target sequence 2 (corresponding to the fragment of S protein coding gene of test sample) comprises or at least consists of SEQ ID NO: 3;

a detection target sequence 3 (corresponding to the fragment of E protein coding gene of test sample) comprises or at least consists of SEQ ID NO: 4;

a detection target sequence 4 (corresponding to the fragment of N protein coding gene of test sample) comprises or at least consists of sequences selected from SEQ ID NO: 5 to SEQ ID NO: 8 or any combination thereof;

9. The mock virus vector of item 8, wherein the sequence of the mock virus is shown in SEQ ID NO: 9.

10. A mock virus particle prepared by the mock virus vector of any one of items 1-9, preferably, the mock virus particle is prepared by transfecting the mock virus vector into a human 293T cell line.

11. Use of the mock virus vector of any one of items 1-9 or the mock virus particle of item 10 in the following:

(1) qualitative and quantitative detection of nucleic acid targets in samples; for example, an application for being used as a reference standard (qualitative determination, such as positive and negative determinations) for the presence of a nucleic acid target in a test sample (for example, from a patient with COVID-19, a carrier of SARS-CoV-2, a patient suspected of having COVID-19, or SARS-CoV-2 in a sample), for example, an application for quality analysis and quality control during processes of sample collection, sample storage, and sample RNA extraction; or for example, an application for quantitative detection of SARS-CoV-2 in a sample;

(2) an application for preparing reagents or kits in detecting the nucleic acid target in the sample;

(3) an application for evaluating, for example, a therapeutic effect on a patient carrying the nucleic acid target;

(4) an application for evaluating or screening a drug for the treatment of a disease caused by the organism (for example, a cell, a virus or fungus).

12. A qualitative and quantitative reference standard RNA prepared by extracting the mock virus particle of item 10, wherein the organism is an RNA virus.

13. The qualitative and quantitative reference standard RNA of item 12, which is used as a reference standard in the process of reverse transcription from RNA to cDNA involved in the detection of RNA viruses such as SARS-CoV-2, for example, being used for quality analysis and quality control in a reverse transcription reaction system using RNA as a sample.

14. A qualitative and quantitative reference standard cDNA or DNA, wherein the qualitative or quantitative reference standard cDNA is prepared by reverse transcription of the qualitative or quantitative reference standard RNA of item 12, and the quantitative reference standard DNA is prepared by extracting the DNA of the mock virus particle of item 10, wherein the genetic material of the organism is DNA.

15. The qualitative and quantitative reference standard cDNA or DNA of item 14, which is used for quality analysis and quality control of amplification efficiency and fluorescence signal in an DNA amplification process involved in a process of detecting an RNA virus (such as SARS-CoV-2) or a process of detecting an organism of which the genetic material is DNA.

16. A kit for qualitatively and quantitatively detecting a nucleic acid target sequence of a sample, comprising (1) the mock virus particle of item 10, the qualitative or quantitative reference standard RNA of item 12 or 13, or the qualitative or quantitative reference standard cDNA or DNA of item 14 or 15, (2) primers for amplifying housekeeping genes and probes, (3) primers for amplifying the qualitative or quantitative reference standard RNA of item 12 or 13 or the qualitative and quantitative reference standard cDNA or DNA of item 14 or 15 and probes, (4) primers for amplifying the nucleic acid target of the sample to be detected and probes, Wherein the primers in (3) and (4) are the same, and labels of the probes in (2), (3) and (4) are different from each other.

17. The kit of item 16, wherein the length of the primers is 12-30 bp, the length of the probes is 20-30 bp, and the annealing temperature difference between the primers and the probes is about 10° C.

18. The kit of item 16 or 17, wherein the labels of the probes in (2), (3) and (4) are selected from Cy5, Fam or Hex or AP593.

19. The kit of item 18, wherein the primers and probes in the kit are composed of primers and probes for the house-keeping genes and primers and probes for detection target sequences, specially:

(1) the primer and probe sequences of the housekeeping genes are shown in SEQ ID NO:10 to SEQ ID NO:21;

(2) the probe sequences for the detection target sequence 1 (corresponding to the fragment of Orf1ab coding gene of test sample) are shown in SEQ ID NO:22, SEQ ID NO:23;

(3) the probe sequences for the detection target sequence 2 (corresponding to the fragment of N protein coding gene of test sample) are shown in SEQ ID NO:24 to SEQ ID NO:27;

(4) the probe sequence for the detection target sequence 3 (corresponding to the fragment of S protein coding gene of test sample) is shown in SEQ ID NO:28;

(5) the probe sequence for the detection target sequence 4 (corresponding to the fragment of E protein coding gene of test sample) is shown in SEQ ID NO:29;

(6) primers for amplifying the detection target sequence 1 are shown in SEQ ID NO:30 to SEQ ID NO:33;

(7) primers for amplifying the detection target sequence 2 are shown in SEQ ID NO:34 to SEQ ID NO:41;

(8) primers for amplifying the detection target sequence 3 are shown in SEQ ID NO:42, and SEQ ID NO:43;

(9) primers for amplifying the detection target sequence 4 are shown in SEQ ID NO:44, and SEQ ID NO:45;

20. A method for qualitatively and quantitatively detect-ing a nucleic acid target sequence of a sample, comprising using the kit of any one of items 16-19.

21. The method of item 20, comprising:

amplification step 1: amplifying at least two of the Orf1ab, S protein gene, E protein gene, N protein gene of sample SARS-CoV-2 by using at least 2 pairs of primers for amplifying the detection target sequence 1-4 in the kit of item 19, amplifying step 2: amplifying the detection target sequences 1-4;

amplification step 3: amplifying the housekeeping genes.

22. The method of any one of items 2-21, wherein the amplification steps 1-3 are performed in the same or differ-ent reaction systems.

23. Any of the preceding items, for use in any DNA or RNA virus, including but not limited to HBV, HCV, HPV, HIV. The schematic diagram of design of the quantitative detection nucleic acid fragment of the present invention is shown in FIG. 20 (and several examples in FIG. 28). Taking the orf1ab gene of SARS-CoV-2 recommended by the Chinese CDC and the spike protein-encoding gene selected in the present invention as examples, the schematic diagram of design of quantitative detection nucleic acid fragment is shown in FIG. 21 and FIG. 22. FIG. 24 shows raw materials of the SARS-CoV-2 nucleic acid detection kit and "quality controls" used for quality analysis and quality control in the production process of the kit. FIG. 25 shows a SARS-CoV-2 nucleic acid detection kit (quantitative), and shows that the spike-in positive reference of the present invention is added to the sampling tube in FIG. 24.

In order to better solve the problem of competitive and non-competitive quantitative detection nucleic acid frag-ments (spike-in internal controls), it is necessary to better determine the minimum limit of the target to be tested and accurately calculate the molecule number of the target to be tested in the sample.

For the design of competitive and non-competitive quan-titative detection nucleic acid fragments (spike-in internal control) for the nucleic acid sequence of the target to be detected in a specific organism, based on the differences between the sequences of primer regions, probe regions, and spacers in amplicon region of the spike-in internal control and the sequences of corresponding primer regions, probe regions, and spacers in amplicon region of the target sequence, there are many types of spike-in internal controls, and the basic principle of design is shown in Table A.

TABLE A

Exemplary design principles of spike-in internal control (DNA or RNA) sequence that are spiked into the test sample or sample collection device (tube)

| design method of spike-in internal control | Primer region (including upstream/downstream) | amplicon region (excluding primer and probe regions) | Probe region |
|---|---|---|---|
| 1 | completely identical | completely identical | 6~14 bases different |
| 2 | completely identical | 30~80 bases identical | 6~14 bases different |
| 3 | 6~18 bases identical | completely identical | 6~14 bases different |
| 4 | 6~18 bases identical | 30~80 bases identical | 6~14 bases different |
| 5 | completely different | completely identical | 6~14 bases different |
| 6 | completely different | 30~80 bases identical | 6~14 bases different |
| 7 | completely identical | completely identical | completely different |
| 8 | completely identical | 30~80 bases identical | completely different |
| 9 | 6~18 bases identical | completely identical | completely different |
| 10 | 6~18 bases identical | 30~80 bases identical | completely different |
| 11 | completely different | completely identical | completely different |
| 12 | completely different | 30~80 bases identical | completely different |

Definitions

In order to facilitate understanding of the invention, explanations for the terms are given below:

Mock virus: also known as pseudovirus.

Target to be detected: refers to a partial sequence fragment selected from the genome of an organism derived from a known DNA or RNA sequence, such as the nucleic acid target sequence of the sample to be detected, the SARS-CoV-2 gene N target sequence of the SARS-CoV-2 virus-infected sample.

Quality Control (Also Known as Reference Standard, Reference Material)

refers to a mock virus and derived DNA, RNA or cDNA therefrom that contain the same base percentage composition and the same sequence arrangement as the target (DNA or RNA) sequence from a certain organism.

Reference standard (qualitative and quantitative reference standard) (Reference standard, Reference material) refers to a mock virus and derived DNA, RNA or cDNA therefrom that contain the same base number (bp) and the same base percentage composition as the target (DNA or RNA) to be detected from the organism, but that the base sequence may be 8-25%, 4-10%, 2-5% identical to the target (DNA or RNA) to be detected.

Quantitative detection nucleic acid fragment: refers to spike-in internal controls (Internal controls, ICs for short), which has the same nucleic acid sequence fragments as the standard, and also refer to the standard that can be spiked into the sample to be detected or a sample collection device (tube).

For example, the design principles for spike-in internal control include:

(1) monitoring all steps of the diagnostic procedure (sampling, nucleic acid extraction, RT, PCR, or RT-PCR);

(2) being used for DNA or RNA targets to be detected;

(3) there should be a minimum limit on the copy number of DNA residual in the production of mock virus (pseudovirus) vectors;

(4) It can be single or multiplexed for one-step or two-step RT-PCR reaction.

The term "reference" as used herein, also referred to as "reference standard," refers to one or more uniform enough substances with their biometric property (quantity) values (such as content, sequence, activity, structure, or typing) well determined, for calibrating instruments, evaluating biometric methods, or assigning a value to a material.

In the present invention, "the base sequence between the 5' end sequence A and 3' end sequence B of the quantitative detection nucleic acid fragment and the base sequence between the 5' end sequence A' and 3' end sequence B' of the nucleic acid target sequence of test sample are completely different" means there is no subsequences having more than 3 contiguous bases, for example, 4, 5, 6, or 7 contiguous bases, preferably, 8-30 contiguous bases between the two base sequences after their alignment, are identical.

In the present invention, lentivirus vectors and adenovirus vectors that can be used are those conventionally used in the field without any biological safety issues, including lentivirus vectors (Gene delivery by lentivirus vector, Cockrell, Adam S., et al., Molecular Biotechnology 36(3), 184-204; Lentiviral Vector System for Gene Transfer, Gilbert, James R., et al., 2003, or FIV virus vector (Feline Immunodeficiency Virus (FIV) as a Model for Study of Lentvirus Infections: Parallels with HIV, John, H. Elder et al., Curr HIV Res 2010 January, 8(1): 73-80; Efficient transduction of nondividing human cells by feline immunodeficiency virus lentiviral vectors, Eric M. Poeschla et al., Nature Medicine, volume 4, No. 3, March 1998; FIV: from lentvirus to lentivector, Dyana T. Saenz et al., J. Gene Med 2004, 6, S95-S104). In a specific embodiment, the lentivirus vector is pEZ-Lv201.

BRIEF DESCRIPTION OF THE DRAWINGS

FIG. 1 shows the list of SARS-CoV-2 detection reagents approved by the National Medical Products Administration since Mar. 6, 2020.

FIG. 5 is a graph showing the blast results of orf1ab and G119753.

FIG. 26 shows the distribution of one-step RT-ddPCR one-dimensional droplet (panels a-b) and copy number concentration quantification curve (Figure c) of the N gene and S gene (Figure b) in the "mock virus" spike-in standard RNA.

DETAILED DESCRIPTION OF THE INVENTION

Although the present invention has described the specific embodiments, certain modifications and equivalents will be apparent to those skilled in the art and are intended to be included within the scope of the present invention.

The present invention is illustrated by the following Examples, which would not limit the present invention in any way.

Example 1: Construction Method of Recombinant Plasmid

1. Experimental Materials

Reagents: DNA Polymerase (Gencopoeia, C0103A); primer Oligo (Invitrogen); cloning vector pEZ-Lv201 (Genecopoeia); Fast-Fusion™ Cloning Kit (Gencopoeia, FFPC-C020); gel recovery kit (Omega); 2T1 competent (Genecopoeia, U0104A); STBL3 competent (Genecopoeia, U0103A); Restriction enzymes (Fermentas); DNA Ladder (Genecopoeia); E.Z.N.A.® Gel Extraction Kit (OMEGA); UltraPF™ DNA Polymerase Kit (Genecopoeia, C0103A); E.Z.N.A.® Plasmid Mini Kit I (OMEGA); Endotoxin-Free Plasmid Mini/Middle Kit (Omega).

2. Experimental Steps

In this Example, a coronavirus nucleic acid detection target sequence and a fluorescent protein gene sequence are inserted into a lentivirus vector, and the specific steps are as follows:

A. Design of the Vector

Figure 2:
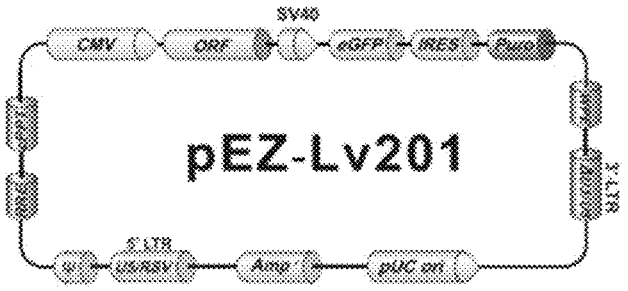
FIG. 2 shows the construction of a "mock virus" vector backbone for the detection of 2019-nCov spike-in reference standards by NGS and RT-PCR methods.

1. The backbone of the vector is shown in FIG. 2

2. Expression of clone information

The SARS-CoV-2-specific target orf1ab sequence fragment was cloned into a lentivirus clone vector.

The SARS-CoV-2-specific target orf1ab sequence was shown in SEQ ID NO: 1

3. Construction steps (1) Synthesis of SARS-CoV-2 Specific Target orf1ab Sequence Fragment Primers for fragment synthesis in Table 1 were designed and synthesized according to the insert sequences

TABLE 1

| Primers for synthesis of insertion fragments | |
| --- | --- |
| Primer ID | Sequences |
| cCDC-orf1ab-PF1 | CCCTCACTAAAGGGAGGAGAAGCATGTCGACGAATTCCTAATAC GACTCACTATAG (SEQ ID NO: 52) |
| cCDC-orf1ab-PF2 | GTGGCAACGGCAGTACAGACAACGATATCCTATAGTGAGTCGTA TTAGGAATTCG (SEQ ID NO: 53) |
| cCDC-orf1ab-PF3 | TGTACTGCCGTTGCCACATAGATCATCCAAATCCTAAAGGATTT TGTGACTTAAAAGGT (SEQ ID NO: 54) |
| cCDC-orf1ab-PF4 | CAAGTTGTAGGTATTTGTACATACTTACCTTTTAAGTCACAAAA TCCTTTAGGATTTG (SEQ ID NO: 55) |
| cCDC-orf1ab-PF5 | AGGTAAGTATGTACAAATACCTACAACTTGTGCTAATGACCCTG TGGGTTTTACACTTA (SEQ ID NO: 56) |
| cCDC-orf1ab-PF6 | AATGACCCTGTGGGTTTTACACTTAAAATGCAGTTCCGAGCTCA CTCGACTCTCTGATC (SEQ ID NO: 57) |
| cCDC-orf1ab-PF7 | CCGAGCTCACTCGACTCTCTGATCAGACGATGGTTTTACTTATC ACCAAATCCGCGTAG (SEQ ID NO: 58) |
| cCDC-orf1ab-PF8 | ACGATTGTGCATCAGCTGACTACGATCTGCCTACGCGGATTTGG TGATAAGTAAAAC (SEQ ID NO: 59) |
| cCDC-orf1ab-PF9 | GTAGTCAGCTGATGCACAATCGTTTTTAAACGGGTTTGCGGTGT AAGTGCAGCCCGTCT (SEQ ID NO: 60) |
| cCDC-orf1ab-PF10 | CACATTCCACAGCTCGAGTGCCTGTGCCGCACGGTGTAAGACGG GCTGCACTTACACCG (SEQ ID NO: 61) |

Figure 3:
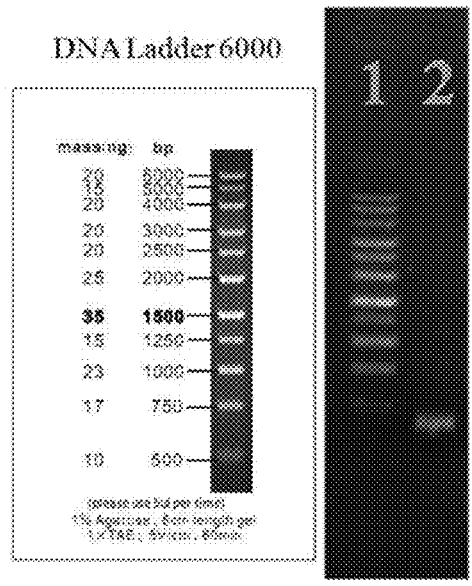
FIG. 3 is an electropherogram of synthesized fragments. Lane 1: Marker 6000; Lane 2: PCR synthesis product L (362 bp).

The primers in Table 1 were diluted to 50 pmol/µl, and then 1 µl of each was taken and mixed evenly for later use;

PCR amplification of the insertion sequences: the insertion fragment M was amplified by using the primer mixture in Table 1 as a template, the cCDC-orf1ab-PF1+cCDC-orf1ab-PF10 as primers, and by using the reaction system in Table 2 and the reaction program in Table 3; electrophoresis detection results were shown in FIG. 3, and a product L fragment of about 362 bp was obtained; and then the PCR product and synthesized fragment were purified by E.Z.N.A.® Cycle Pure Kit (OMEGA).

Target sequence insertion fragment M of "mock virus" that can be spiked in for the detection of 2019-nCoV reference standards by such as NGS, RT-PCR methods were synthesized, the sequence of which was shown in SEQ ID NO: 46;

TABLE 2

| PCR reaction system | |
| --- | --- |
| Reagent name | 1 × volume |
| 5 × UltraPF ™ Buffer | 5 µl |
| dNTP (25 mM) | 0.2 µl |
| Mg²⁺ (50 mM) | 0.75 µl |
| UltraPF ™ DNA Polymerase (5 U/µl) | 0.2 µl |
| Primer mix in Table 1 | 1 µl |
| Primer (5 pmol/L) | 2 µl |
| ddH₂O | Added to 25 µl |

TABLE 3

| PCR reaction procedure | | |
| --- | --- | --- |
| reaction temperature | time | Cycle numbers |
| 98° C. | 3 min | 1 |
| 98° C. | 20 sec | 35 |

TABLE 3-continued

| PCR reaction procedure | | |
| --- | --- | --- |
| reaction temperature | time | Cycle numbers |
| 58° C. | 30 sec | |
| 72° C. | 1 min | |
| 72° C. | 10 min | 1 |

B. The Synthesized Insertion Fragment M was Cloned into a Vector of Interest

1. Enzyme Cleavage of the Vector

The enzyme cleavage system was established according to Table 4. The cleavage product of the vector was recovered by E.Z.N.A.® Gel Extraction Kit from OMEGA.

TABLE 4

| Enzyme cleavage system | |
| --- | --- |
| reagent | Amount |
| pEZ-Lv201 | 3 µg |
| 10 × NEB buffer | 4 µl |
| EcoRI (NEB) | 0.4 µl (10 µ/µl) |
| XhoI (NEB) | 0.4 µl (10 µ/µl) |
| ddH₂O | Added to 40 µl |

2. Ligation of Synthesized Insertion Fragment M and Plasmid Vector

In-fusion reaction was performed with Fast-Fusion Cloning Kit. After the reaction, 5 µl was taken to transform *E. coli* competent cells 2T1.

3. Screening of Recombinant Gene Clones by PCR

Each PCR reaction system was added 16 µl ddH2O and 1 µl vector primers SEQ ID NO: 47 and SEQ ID NO: 48 (5 pmol/µl), and the PCR reaction procedure was shown in

17

Figure 4:
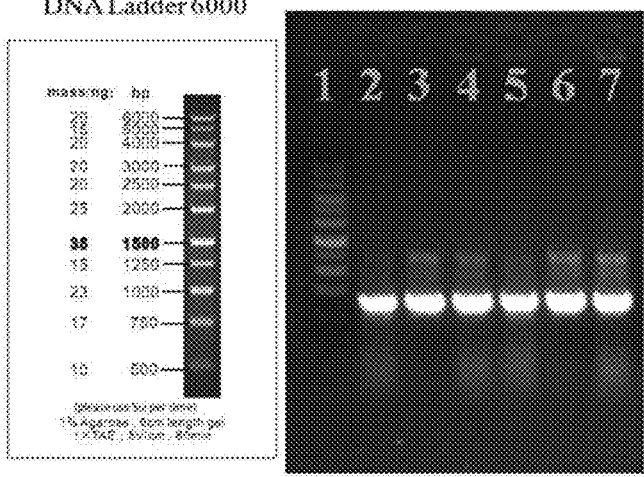
FIG. 4 is the electropherogram of colony PCR detection results. Lane 1: Marker 6000; Lane 2: Colony PCR product (640 bp); Lane 3: Colony PCR product (640 bp); Lane 4: Colony PCR product (640 bp); Lane 5: Colony PCR product (640 bp); Lane 6: Colony PCR product (640 bp); Lane 7: Colony PCR product (640 bp).

Table 5; the PCR products were detected by electrophoresis, and the detection results were shown in FIG. 4. The sizes of DNA fragments were estimated based on Marker, and positive clones containing the target DNA fragments were selected. Plasmid DNA was extracted with E.Z.N.A.® Plasmid Mini Kit I(OMEGA), and the plasmid was sequenced. According to the alignment results in FIG. 5, it was known that the sequencing plasmid G119753 was the expected correct clone, which expressed that a RNA sequence from 5' LTR to 3' LTR sequence (insert 2019-nCoV "mock virus" RNA sequence) was fragment N (see SEQ ID NO: 49), and the full sequence of plasmid (full sequence of "mock virus" vector) was fragment W (see SEQ ID NO: 9);

TABLE 5

| PCR Reaction Procedure | | |
| --- | --- | --- |
| reaction temperature | time | Cycle numbers |
| 94° C. | 3 min | |
| 94° C. | 30 sec | 25 Cycles |
| 58° C. | 30 sec | |
| 72° C. | 2 min | |
| 72° C. | 10 min | |

Example 2: Preparation of Lentivirus

Figure 6:
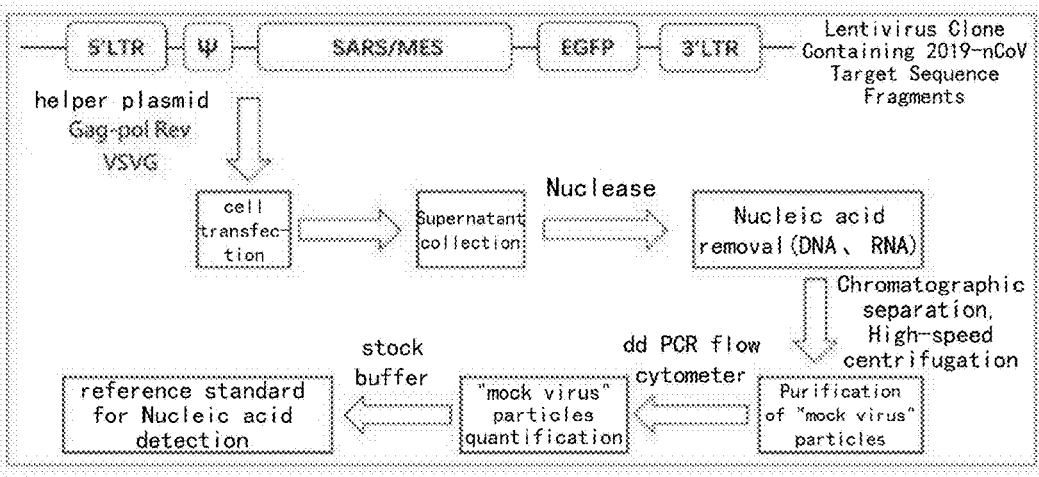
FIG. 6 is a flow chart of preparation of recombinant lentivirus particles.

After obtaining the recombinant lentivirus vector, recombinant lentiviral particles can be prepared. FIG. 6 shows the preparation process.
1. Experimental materials and reagents: culture medium (CORNING, 10-013-CV), fetal bovine serum (Excell Bio, FSP500), Lenti-Pac™ HIV lentivirus packaging kit (GeneCopoeia, LT003)
2. Experimental Steps
The preparation steps of lentivirus were as follows:
1. 293T (ATCC® CRL-3216™) cells were cultured in DMEM medium with 10% fetal bovine serum, under 5% $CO_2$ at 37° C.; the recombinant plasmid prepared in Example 1 and a helper plasmid containing Gag-pol and Rev were co-transfected into cells according to the recommended procedure of Lenti-Pac™ HIV lentivirus packaging kit;
2. After 12 h of transfection, the medium was replaced with fresh medium and cells were cultured for 24 h continuously;
3. Supernatant of cultured cells was collected, which contained lentivirus particles (named as LPP-WH-Fragment3-Lv201).

Example 3: Concentration of Lentivirus

1. Experimental Materials
Reagents: Lentivirus Concentration Solution (6×) (GeneCopoeia, LT007), PBS (GeneCopoeia, PE002).
2. Experimental Steps
1). The supernatant containing lentivirus particles was collected from the tool cell culture plate or flask. The supernatant was centrifuged at 2000 g for 10 min at 4° C. to remove cell debris.
2). The concentration reagent was purchased from GeneCopoeia (Lenti-Pac™ Lentivirus Concentration Reagent, LT007). The lentivirus supernatant and concentration reagent were mixed at a ratio of lentivirus solution volume:concentration reagent volume=5:1 (directly adding the 6× stock solution of lentivirus concentration reagent), and then incubated at 0-4° C. for 2 h or more (or incubated overnight). During the stable storage period of lentivirus, appropriately prolonging the incubation period can improve the recovery rate of lentivirus. Note: the lentivirus can be stably stored for about 3 days at 0-4° C.
3). After incubation, the mixture was centrifuged at 3500 g for 25 min at 4° C.
4). After centrifugation, the supernatant was carefully aspirated and discarded, and the left pellet was lentivirus particles.
Note: the centrifuged pellet which is lentivirus particle should be avoided to be aspirated (in some cases, the pellet may not be visible).
5). DMEM or PBS was taken in a volume of 1/10-1/100 the volume of the lentivirus supernatant collected in step 1 and used for concentration, and then the lentivirus pellet was resuspended by pipetting (for example, if the supernatant collected in step 1 was 10 mL, the amount of DMEM or PBS taken in this step was 0.1 mL-1 m).
NOTE: the pipetting should be performed gently when resuspending the lentivirus pellet.
6). When the concentration operation of resuspended lentivirus solution was finished, it was stored at −80° C. after aliquoting, and meanwhile a small amount of the concentrated lentivirus solution was taken to determine the titer.

Example 4: Quantification of Lentivirus

1. Experimental Materials
Reagents: Medium (CORNING, 10-013-CV), Fetal Bovine Serum (Excell Bio, FSP500), PBS (GeneCopoeia, PE002), Trypsin (CORNING, 25-053-CI), Lenti-Pac™ Lentivirus Titer Detection kit (GeneCopoeia, LT006), penicillin-streptomycin solution (HyClone), RNaseLock™ RNase inhibitor.
2. Experimental Steps
The lentivirus titer can be measured by four methods:
Method i: Detection of the physical titer of lentivirus by using a real-time fluorescence quantitative PCR instrument.
Method ii: Determination of the biological copy number (titer) of lentivirus by using a fluorescence microscopy cytometry.
Method iii: Determination of lentivirus biotiter by using flow cytofluorimetry.
Method iv: Detection of the copy number of lentivirus RNA by ddPCR method.

TABLE 6

| Result comparison of the four methods: | | | | |
| --- | --- | --- | --- | --- |
| experimental method | Method i | Method ii | Method iii | Method iv |
| final titer results of lentivirus (copies/ml) | $1.96 \times 10^{10}$ | $1.99 \times 10^{10}$ | $6.35 \times 10^{10}$ | $4.17 \times 10^{10}$ |

Method i: Detection of the Physical Titer of Lentivirus by a Real-Time Fluorescence Quantitative PCR Instrument.
1. RNA Extraction
RNA was extracted according to the molecular cloning experiment manual. Finally, 50 μL of TE buffer was used to dissolve RNA precipitates (herein, the TE buffer was a 100

µM TE buffer prepared from DEPC-treated water, which was used in the present invention to dissolve the RNA precipitate).

2. Treatment with DNase I (Removal of Genome of a Free Cell and Plasmids)

DNase I reaction. The following reaction (total volume 25 µL) was performed according to Table 7 by using a 1.5 mL tube:

TABLE 7

| DNase I reaction system | |
| --- | --- |
| Reagent | Amount |
| DEPC treated water | 1.5 µL |
| Lentiviral RNA | 20.0 µL |
| DNase I buffer (10×) | 2.5 µL |
| DNase I | 1.0 µL |
| Total | 25.0 µL |

Incubation: 1) 37° C., 30-60 min; 2) 75° C., 10 min (to inactivate DNase I)

Note:

If the DNase I digestion step was omitted, a qPCR reaction using the unreverse-transcribed RNA sample as a template must be added as a control in the qPCR reaction step to determine the copy number of plasmid DNA carried in a sample (without subjected to DNase I digestion), wherein the copy number of RNA in the sample was obtained by subtracting the copy number of plasmid DNA determined by the control from the copy number determined by the qPCR reaction using the reverse transcribed product as a template.

3. Reverse Transcription

RNA-Primer Mix was prepared according to Table 8, mixed evenly, incubated at 70° C. for 5 min, and then the centrifuge tube was placed on ice immediately to cool down.

TABLE 8

| RNA and cDNA Synthesis Primer binding reaction system | |
| --- | --- |
| Reagent | Amount |
| RNA (digested by DNase I) | 10.0 µL |
| cDNA Synthesis Primer (4.0 µM) | 5.0 µL (final concentration 1.0 µM) |

Note:

The random primers in the kit (final concentration of 10 µM in reverse transcription reaction solution) can be used in place of HIV cDNA Synthesis Primer. It was not necessary to use cDNA Synthesis Primers and random primers at the same time.

1) The reverse transcription reaction system was prepared according to Table 9, and other components were added (total volume 20 µL), and then incubated at 37° C. for 60 min.

TABLE 9

| Reverse transcription reaction system | |
| --- | --- |
| Reagent | Amount |
| Reverse Transcription Buffer (10×) | 2.0 µL |
| 25 mM dNTP | 1.0 µL |
| RNaseLock ™ RNase inhibitor | 1.0 µL |
| Reverse Transcription Enzyme | 1.0 µL |
| Total | 20.0 µL |

2) 90° C., 10 minutes. The product can be directly used in qPCR detection experiments as a test sample, or stored at −20° C.

4. qPCR Reaction

1) Preparation of Standard Curve Samples

Positive reference standard (obtained from the Lenti-Pac™ Lentivirus Titer Assay Kit (GeneCopoeia, LT006) with a copy number of $1\times10^9$ copies/µL) was diluted.

A standard curve was generated (2 µL of each subsequent dilution gradient was used as a template for qPCR reaction).

(1) Initial copy number: $1\times10^8$ copies/µL (operation method: 5 µL qPCR standard (DNA)+45 µL ddH$_2$O)

(2) Initial copy number: $1\times10^7$ copies/µL (operation method: 5 µL ①+45 µL ddH$_2$O)

(3) Initial copy number: $1\times10^6$ copies/µL (operation method: 5 µL ②+45 µL ddH$_2$O)

(4) Initial copy number: $1\times10^5$ copies/µL (operation method: 5 µL ③+45 µL ddH$_2$O)

(5) Initial copy number: $1\times10^4$ copies/µL (operation method: 5 µL ④+45 µL ddH$_2$O)

(6) Initial copy number: $1\times10^3$ copies/µL (operation method: 5 µL ⑤+45 µL ddH$_2$O)

2) qPCR Reaction System was Prepared According to Table 10 (Total Volume of 20 µL):

TABLE 10

| qPCR reaction system | |
| --- | --- |
| Reagent | Amount |
| qPCR Standard or cDNA Sample or ddH$_2$O | 2.0 µL |
| 2 × All-in-One ™ qPCR Mix | 10.0 µL |
| qPCR Primer Mix (2.5 µM) | 2.0 µL |
| ddH$_2$O | 6.0 µL |
| Total | 20 µL |

Note:

(1) The components in the reaction system (except for the positive reference standard and sample) were premixed before divided into tubes.

(2) Non-template control (NTC) group in the qPCR reaction was set.

(3) For reference samples, 2 µL was taken from each dilution tube:

3) qPCR reaction procedure

The reaction procedure of Table 11 was suitable for the Bio-Rad iQ5 real time PCR detection system. The melting curve procedure was shown in Table 12. Those skilled in the art can make routine fine-tuning depending on the detection system used.

TABLE 11

| qPCR reaction procedure | | | | |
| --- | --- | --- | --- | --- |
| Cycle numbers | Steps | Temperature | Duration |
| 1 | denaturation | 95° C. | 10 min |
| 40 | denaturation | 95° C. | 10 sec |
| | Annealing | 60° C. | 20 sec |
| | Extension | 72° C. | 15 sec |

TABLE 12

| Melting curve procedure | | |
| --- | --- | --- |
| Temperature | Temperature interval | Duration |
| 72-95° C. | 0.5° C. | 6 sec/each |
| 30° C. | | 30 sec |

Figure 7:
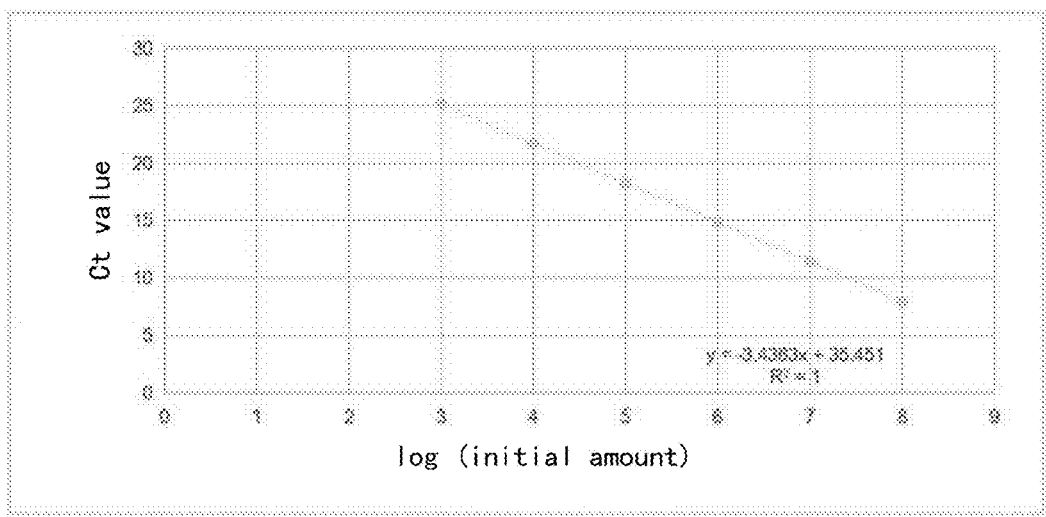
FIG. 7 is a standard curve graph of the Ct value as a function of log (initial copy number) of the gradient diluted references. Legend: qPCR reaction is performed on all the reference standards gradient diluted to obtain the Ct value (amplification threshold cycle number) of each sample, with log (initial copy number) as abscissa X, Ct value as ordinate Y, and then a standard curve as well as a curve formula and correlation coefficient $R^2$ are obtained.

4) Data Analysis (1) After the qPCR reaction, the Ct value (amplification threshold cycle number) of each reference was read, and a standard curve with log (initial copy number) as the abscissa and Ct value as the ordinate was drawn, as shown in FIG. 7 (standard curve of log (initial copy number) versus Ct value of the diluted in gradient reference), and then the curve formula was obtained. The correlation coefficient of the standard curve should be higher than 0.99.

Remarks for FIG. 7: qPCR reaction is performed on all the references diluted in gradient to obtain the Ct value (amplification threshold cycle number) of each sample, with log (initial copy number) as abscissa X, Ct value as ordinate Y, and then a standard curve as well as a curve formula and correlation coefficient $R^2$ are obtained.

(2) The Ct value of test sample was read and introduced into the standard curve formula (y=−3.4363x+35.451) in ① (shown in FIG. 7), and the corresponding log (initial copy number) and the initial copy number thereof were calculated.

(3) Copy number (copies/ml) of original sample was obtained by multiplying the above initial copy number by the dilution factor (wherein, the dilution factor was calculated by the following formula).

$$\frac{\text{Dilution}}{\text{Factor}} = $$

$$\frac{RNA \text{ volume } (\mu L)}{\text{original sample volume } (\mu L)} \times \frac{DNase \text{ reaction volume}(\mu L)}{RNA \text{ volume in } DNase \text{ reaction } (\mu L)} \times$$

$$\frac{RT \text{ reaction volume}(\mu L)}{RNA \text{ volume in } RT \text{ reaction } (\mu L)} \times \frac{1000 \ \mu L/mL}{cDNA \text{ volume in } PCR \text{ reaction } (\mu L)}$$

Note:

(A) RNA volume: 50 μL (according to this experimental procedure)

(B) Original sample volume: lentivirus particle solution volume for RNA extraction, 10 μl (C) DNase reaction volume: 25 μL (according to this experimental procedure)

(D) RNA volume in DNase reaction: 20 μL (according to this experimental procedure)

(E) RT reaction volume: 20 μL (according to this experimental procedure)

(F) RNA volume in RT reaction: 10 μL (according to this experimental procedure)

(G) cDNA volume in PCR reaction: 2 μL (according to this experimental procedure)

(4) Each lentivirus particle contains two single-stranded positive-stranded RNA genomes, therefore, the number of lentivirus particles obtained should be ½ of the copy number. Therefore, the physical titer of lentivirus particle number (copies/ml) is obtained by dividing the original sample copy number by 2. Table 13 shows a data sheet of the calculation process of the physical titer of lentivirus particles.

TABLE 13

| | Data sheet of the calculation process of the physical titer of lentivirus particles | | |
| --- | --- | --- | --- |
| Sample | Ct value (amplification threshold cycle number) | Log (initial copy number) | initial copy number (SQ) | physical titer (copies/ml) |
| 1 | 13.13 | 6.49 | 6.21E+06 | 1.96E+10 |

Method ii: Determination of the Biological Copy Number (Titer) of Lentivirus by Using a Fluorescence Microscopy Cytometry Day 1: Culture of H1299 Cells (ATCC® CRL-5803™)

1. A 24-well culture plate was used; $5 \times 10^4$ cells and 0.5 mL of DMEM complete medium (supplemented with 10% heat-inactivated fetal bovine serum, penicillin-streptomycin) were respectively added to each well, and incubated overnight (about 24 h) in 5% $CO_2$, at 37° C.

Day 2: Infection of H1299 Cells

2. After 24 hours of cell culture, the culture medium was removed; 250 μl of DMEM medium (supplemented with 10% heat-inactivated fetal bovine serum, penicillin-streptomycin solution), and the diluted lentivirus as shown in step 3 were sequentially added. Each lentivirus was added to 3 wells of culture plate.

3. The lentivirus was fluorescently labeled and the detection titer could be determined by fluorescence microscopy cytometry. The lentivirus was inoculated in gradient firstly, and 0.03 μL, 0.3 μL, and 0.3 μL of lentivirus stock solution were added to each well (triplicate wells for each lentivirus). Appropriate DMEM medium (supplemented with 10% heat-inactivated fetal bovine serum, penicillin-streptomycin solution) was added to each well to a final volume of 0.5 mL per well. Blank control well was used as a reference.

Day 3: Replacement of Medium

4. The original medium was removed and cells were incubated in fresh DMEM medium (supplemented with 5% heat-inactivated fetal bovine serum, penicillin-streptomycin solution) for 24 hours.

5. Lentivirus titer was determined by cytometry with an Inverted Fluorescence Microscope.

The wells where the number of fluorescent cells could be counted under the microscope were selected; 5 fields of view were randomly selected and photographed, and the number of fluorescent cells in the well was calculated.

In a well added with 0.03 μl of virus, the number of fluorescent cells was moderate and the number of cells could be calculated. The average number of fluorescent cells in 5 fields of view in the well was X, and the lentivirus titer was calculated according to the following formula:

Lentivirus titer (TU/mL)=X (average number of fluorescent cells)×63.3 (area of 24-well plate/area of microscope observation view field)/0.03 μl (volume of lentivirus solution actually added).

The biological titer of Lentivirus determined by fluorescence microscopy cytometry in Table 14 was obtained.

TABLE 14

| Biological titer of Lentivirus determined by fluorescence microscopy cytometry | | | | | | | | | |
|---|---|---|---|---|---|---|---|---|---|
| | triplicate well 1 | | triplicate well 2 | | triplicate well 3 | | | | |
| Lentiviral particles | Number of fluorescent cells | Mean value | Number of fluorescent cells | Mean value | Number of fluorescent cells | Mean value | Mean value | titer (TU/ml) | titer (copies/ml) |
| LPP-WH- purified | 61 | 48 | 40 | 45 | 50 | 49 | 47 | $1.99 \times 10^8$ | $1.99 \times 10^{10}$ |
| Fragment (0.03 µl) | 56 | | 49 | | 59 | | | | |
| 3-Lv201 | 36 | | 44 | | 37 | | | | |
| | 45 | | 41 | | 42 | | | | |
| | 40 | | 51 | | 59 | | | | |

Note:
1 TU/ml was approximately equal to 100 copies/ml

Figure 8:
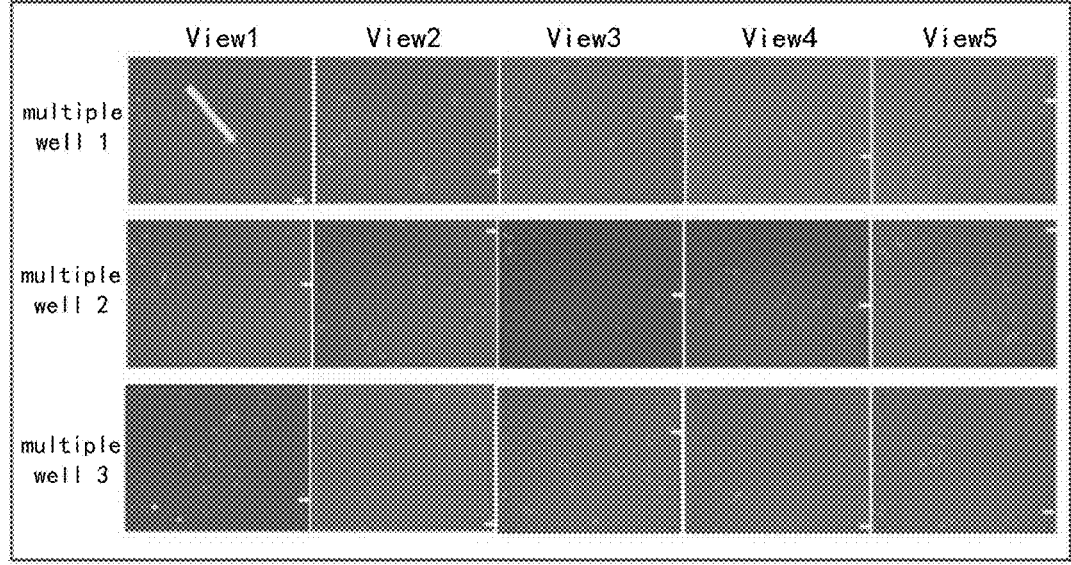
FIG. 8 is a fluorescence image of H1299 cells infected with lentivirus. Legend: all the green fluorescent spots in the figure are counted, and the arrow in the figure represents one of the fluorescent spots.

After infection of H1299 cells by the lentivirus, the fluorescence picture as shown in FIG. 8 was obtained by an inverted fluorescence microscope. (an inverted fluorescence microscope with a 100-fold field of view, with GFP fluorescence for photographing and counting, all the fluorescent spots in the figure were counted, and the arrow in the figure indicated one of the fluorescent spots). Remarks for FIG. 8: all the fluorescent spots in the figure were counted, and the arrow in the figure represented one of the fluorescent spots. Method iii: Determination of Lentivirus Biotiter by Flow Cytofluorimetry.

Steps 1-4 were the same as steps 1-4 in method ii.
Day 4: Determination of Lentivirus Titer by Flow Cytofluorimetry 5. The lentivirus titer was determined by flow cytofluorimetry (Flow cytometer: BD FACSMelody)

Figures 9, 10, 11:
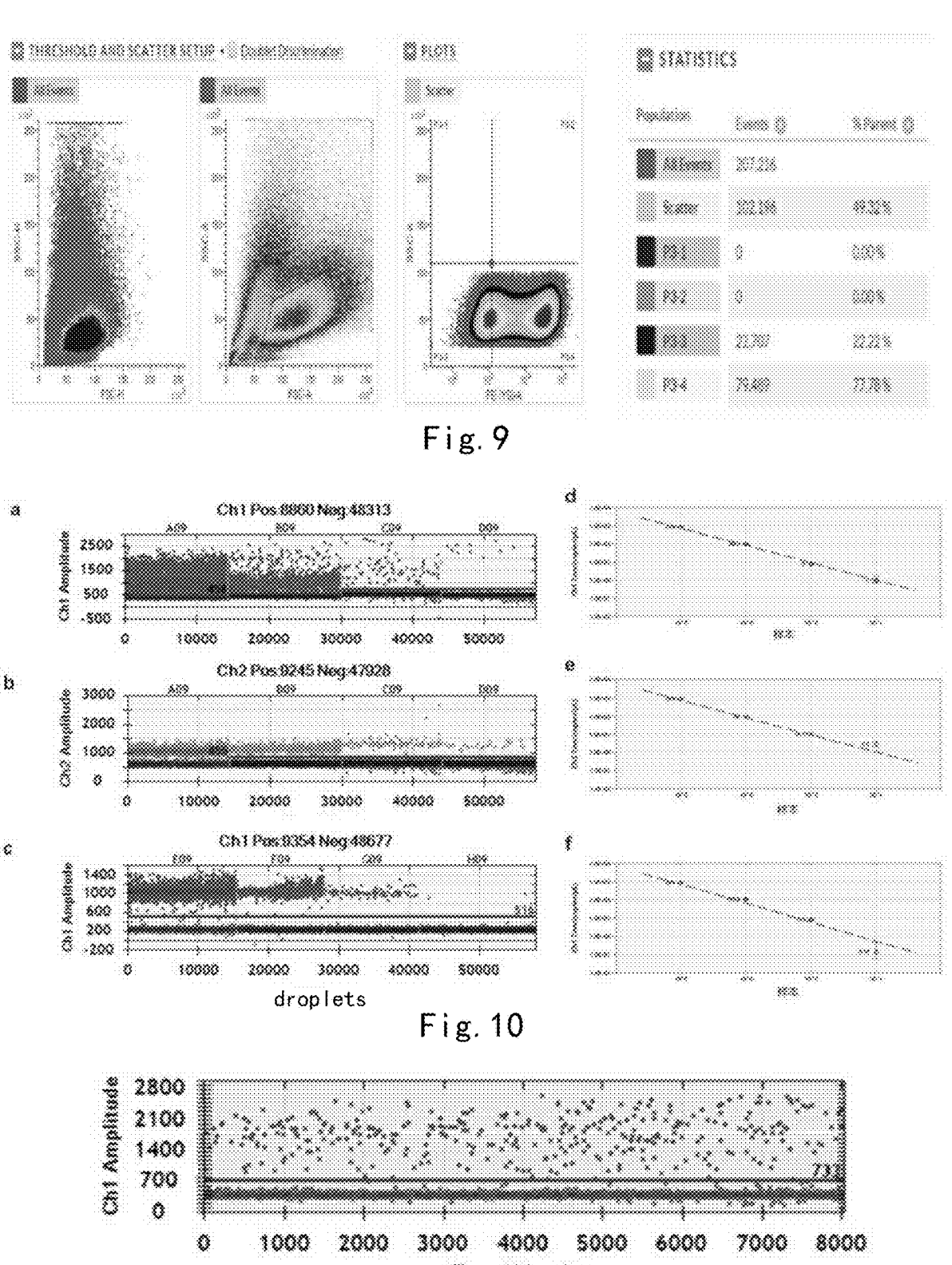
FIG. 9 is the data chart of flow cytometry analysis of cells with eGFP fluorescence. Legend: cells with eGFP fluorescence are measured by flow cytometry, and the percentage of cells with labeled fluorescence is obtained. ordinate: SSC-A refers to relative particle size or internal complexity; abscissa: FITC-A refers to relative particle size; P1-1, P1-2, P1-3: refer to cells without fluorescence; P1-4 refers to sorted target cells with fluorescence, with a positive rate of 2.23%.
FIG. 10 shows the ddPCR one-dimensional droplet distribution of ORF1ab target (panel a), N gene target (panel b) and S gene target (panel c) in the gradient diluted cDNA samples and the copy number concentration quantification curve (panel d-f).
FIG. 11 is the ddPCR droplet one-dimensional map. Blue droplets are positive droplets, gray droplets are negative droplets, and red is the baseline. The abscissa represents the number of droplets, and the ordinate represents the fluorescence intensity.

Cells with eGFP fluorescence could be counted by FACS (flow cytometry). Fluorescence observation of eGFP could be performed using a fluorescence microscope. After observation of the fluorescence state, the cells were digested with trypsin, and the digestion was terminated with DMEM complete medium, and then the cells were centrifuged at 500 g for 10 min. The cells were resuspended in 1 ml of PBS, and the total number of cells in each well was determined with a hemocytometer. Cell were then analyzed by a flow cytometer to obtain the percentage of fluorescent cells, as shown in FIG. 9 (the data map of the flow cytometry analysis of cells with eGFP fluorescence), and the lentivirus titer was calculated according to the following formula:

Lentivirus titer (TU/mL)=percentage of fluorescent cellsxtotal number of cells in well+volume of lentivirus solution actually added (mL). The lentivirus biotiter was shown in Table 15.

TABLE 15

| Biotiter of lentivirus | | | | |
|---|---|---|---|---|
| lentiviral particles | number of cells(cells) | Fluorescence rate (%) | Titer (TU/ml) | Titer (copies/ml) |
| LPP-WH- | 0.03 µl | 8.54E+05 | 2.23 | 6.35E+08 | 6.35E+10 |
| Fragment3- | lentivirus | | | | |
| Lv201 | added | | | | |

Note:
1 TU/ml was approximately equal to 100 copies/ml

Remarks for FIG. 9: cells with eGFP fluorescence were measured by flow cytometry, and the percentage of cells with labeled fluorescence was obtained. ordinate: SSC-A refers to relative particle size or internal complexity; abscissa: FITC-A refers to relative particle size; P1-1, P1-2, P1-3: refer to cells without fluorescence; P1-4 refers to sorted target cells with fluorescence, with a positive rate of 2.23%.

Method iv: Detection of the Copy Number of Lentivirus RNA by ddPCR Method

1. Experimental Materials
   Reagent: Bio-Rad ddPCR™ Supermix for Probes (No dUTP)
   Equipment: Bio-Rad QX200 droplet digital PCR System
2. Experimental Steps
   1. The cDNA obtained by reverse transcription of lentivirus particle RNA was 10-fold gradient diluted with ddH2O (DNase free) to obtain 4 ddPCR samples to be tested;
   2. The ddPCR™ Supermix for Probes (No dUTP) was thawed at room temperature, mixed well by turning upside down and centrifuged briefly;
   3. ddPCR Reaction Mix (FAM/HEX dual channel) was prepared according to Table 16.

TABLE 16

| ddPCR reaction system | | |
|---|---|---|
| Component | Amount | Final concentration |
| 2 × Supermix for Probes (No dUTP) | 10 µL | 1× |
| Primer Mix 1 (10 µM) | 1.8 µL | 0.9 µM |
| Taqman Probe 1 (5 µM) | 1 µL | 0.25 µM |
| Primer Mix 2 (10 µM) | 1.8 µL | 0.9 µM |
| Taqman Probe 2 (5 µM) | 1 µL | 0.25 µM |
| cDNA | 1 µL | |
| ddH₂O | to 20 µL | |
| Total volume | 20 µL | |

4. After the prepared system was mixed well by shaking and centrifuged, it was carefully transferred to sample wells in the middle row of the droplet generation card, and 70 µL of droplet generation oil was added to the well in the lower row, and then droplets were generated in a droplet generator.
5. The generated droplet sample (40 µL) was transferred from the upper row of the droplet generation card to a ddPCR-dedicated 96-well plate, the 96-well plate was sealed with a PX1 heat sealer after covered with aluminum film.
6. After sealing the plate, the PCR reaction should be carried out within 30 minutes, or the PCR should be carried out within 4 hours stored in a 4° C. refrigerator. The PCR reaction should be carried out according to Table 17, and the rate of temperature increase or decrease should be 2° C./sec.

TABLE 17

| | PCR reactions | | |
|---|---|---|---|
| step | temperature | duration | number of cycles |
| predenaturation | 95° C. | 10 min | 1 |
| denaturation | 94° C. | 10 s | 40 |
| annealing | 60° C. | 15 s | |
| extension | 68° C. | 20 s | |
| Enzyme inactivation | 98° C. | 4 min | 1 |
| maintain temperature | 4° C. | ∞ | |

7. After PCR, the 96-well plate was taken out and the droplets on a droplet reader were read.

8. After reading of the droplets, the data results were analyzed by a Bio-rad QuantaSoft software, and the copy number concentrations of ORF1ab and N genes in the "mock virus" cDNA were calculated according to FIG. 10. FIG. 10 showed the ddPCR one-dimensional droplet distribution of ORF1ab target (panel a), N gene (panel b) and S gene (panel c) in the serially diluted cDNA samples and the copy number concentration quantification curve (panel d-f).

Example 5: RNA Extraction

1. Experimental Materials

Reagents: GeneCopoeia RNAzol™ RT RNA Isolation Reagent, isopropanol, 75% ethanol, ddH₂O (RNase and DNase free).

Equipment: Vortex Shaker.

2. Experimental Steps

1. Sample Treatment

400 μl of virus suspension was taken and added to a 1.5-2 ml centrifuge tube containing 1 ml of RNAzol RT, and then mixed well by shaking, and left standing at room temperature for about 5 minutes;

2. Phase Separation

Each 1 ml RNAzol RT was added with 400 μl ddH₂O (RNase and DNase free), or supplemented with ddH₂O (RNase and DNase free) to 1.4 ml; the lid was closed, and then the solution was mixed well by shaking for about 15 sec, and left standing at room temperature for 5 to 15 min. Centrifuge was performed at 10,000 rpm for 15 min;

3. Precipitation

The supernatant was transferred to a new 1.5-2 ml centrifuge tube, added with an equal volume of isopropanol, and left standing at room temperature for 10 min. Centrifuge was performed at 10,000 g for 10 min.

4. Washing

The supernatant was discarded, the remained precipitate was added with 400 μl of 75% ethanol, mixed well and centrifuged at 7500 g for 1-3 min. This washing step was repeated once.

5. Dissolution

The supernatant was discarded; the precipitate was air dried, and added with 50 μl TE (RNase and DNase free) for dissolving, thereby obtaining the total RNA.

Example 6: cDNA Preparation

1. Experimental Materials

Reagents: GeneCopoeia SureScript™ First-Strand cDNA Synthesis Kit, Lentivirus RNA, DEPC treated water.

Equipment: ordinary PCR machine.

2. Experimental Steps

1). Preparation of Reverse Transcription System

The reverse transcription system was prepared according to Table 18 of GeneCopoeia™ SureScript™ First-Strand cDNA Synthesis Kit Instruction:

TABLE 18

| Reverse transcription system for cDNA preparation | |
|---|---|
| reagent | amount |
| 5 × RT buffer | 4 μl |
| 20 × RTase Mix | 1 μl |
| Lentiviral RNA (100 ng/μl) | 5 μl |
| DEPC treated water | To 20 μl |

2). Reverse Transcription Reaction

The reverse transcription procedure was performed according to Table 19 on a ordinary PCR machine.

TABLE 19

| Reverse transcription procedure for cDNA preparation | |
|---|---|
| Reaction temperature | Duration |
| 25° C. | 5 min |
| 50° C. | 60 min |
| 85° C. | 5 min |

The reverse transcribed cDNA was stored at −20° C.

Example 7

RNA Preparation Method and Quality Control Analysis

1. Experimental Materials

Reagents: RNAzol RNA Isolation reagent (GeneCopoeia), MgCl₂·6H₂O (sigma), DEPC (MBCHEM), isopropanol (Guangzhou Chemical Reagent Factory), Trizma Base (Sigma), EDTA (Sigma), RNaseLock (GeneCopoeia), DNase I (NEB), 1-step Taqman qPCR Mix (GeneCopoeia), 2-step Taqman qPCR Mix (GeneCopoeia), BlazeTaq RTase Mix (GeneCopoeia), ddPCR Supermix for Probes (No dUTP) (Bio-rad), FAM-labeled probes (Invitrogen), pipette tips (Axygen), 50 ml centrifuge tubes (BIOFIL), 1.5 ml centrifuge tubes (Axygen).

2. Experimental Steps 1) 80 ml of mock virus culture solution was prepared. After PEG concentration and precipitation, the virus was stored in PBS buffer with a volume of 10 ml and treated with Benzonase twice to remove the residual plasmid DNA;

2) Operation on ice: 300 μl mock virus+1 ml RNAzol, mixed well, left standing for 5 min, then added with 100 μl DEPC treated water to a volume of 1.4 ml;

3) After centrifugation at 10,000 rpm and 4° C. for 10 min, all the supernatants were collected into a 50 ml centrifuge tube, and added with an equal volume of isopropanol;

4) After mixing, the solution was dispensed into 1.4 ml/tube and left standing for 5 min at room temperature;

5) After centrifugation at 10,000 rpm, 4° C. for 15 min, the supernatant was discarded; 400 μl of 75% ethanol (prepared with DEPC treated water) was added to the pellet, mixed well, centrifuged at 7,500 rpm for 2 min at 4° C.; the washing step was repeated again;

6) The supernatant was discarded; the precipitate was left at room temperature for about 5 minutes to be air dried, 50 μl TE (containing RNaseLock: 0.02 U/μl) was added to dissolve the precipitate; all the RNA solutions were mixed well, aliquoted, and stored in a −80° C. refrigerator;

7) Residual plasmid DNA in RNA was treated with DNase I, and the unit of DNase I activity was 7 U/1.5 μg RNA. The amount of each component was: RNA 58 μl, Dnase I 14 μl, 10×Dnase I buffer 8 μl, 37° C. for 15 min or 75° C. for 10 min;

8) DNA residues were detected by qPCR with primers as shown in Table 20. The amount of each component added was: 5×2-step Taqman mix 4 μl, primers and Probe Mix (10 uM) 0.25 μl, RNA 2 μl, DEPC H₂O to 20 μl, and the reaction system was shown in Table 21.

TABLE 20

Relevant primers for detection of DNA residues by qPCR

| No. | primer name | Primer sequence |
|---|---|---|
| 1 | cCDC-F1 | CCCTGTGGGTTTTACACTTAA (SEQ ID NO: 62) |
| | cCDC-R1 | ACGATTGTGCATCAGCTGA (SEQ ID NO: 63) |
| | cCDC-FAM-P1 | 5'-FAM-CCGTCTGCGGTATGTGGAAA GGTTATGG-BHQ1-3' (SEQ ID NO: 64) |
| 2 | cCDC-F2 | GGGGAACTTCTCCTGCTAGAAT (SEQ ID NO: 65) |
| | cCDC-R2 | CAGACATTTTGCTCTCAAGCTG (SEQ ID NO: 66) |
| | cCDC-FAM-P2 | 5'-FAM-TTGCTGCTGCTTGACAGATT-BHQ1-3' (SEQ ID NO: 67) |
| 3 | Ro-E-F | ACAGGTACGTTAATAGTTAATAGCGT (SEQ ID NO: 68) |
| | Ro-E-R | ATATTGCAGCAGTACGCACACA (SEQ ID NO: 69) |
| | E_Sarbeco_P1 | 5'-FAM-ACACTAGCCATCCTTACTGCGC TTCG-BHQ1-3' (SEQ ID NO: 70) |
| 4 | WH-F | CCAGATCCATCAAAACCAAGC (SEQ ID NO: 71) |
| | WH-R | TGCACAAATGAGGTCTCTAGC (SEQ ID NO: 72) |
| | WH-FAM-P | 5'-FAM-AGTGACACTTGCAGATGCTGGC T-BHQ1-3' (SEQ ID NO: 73) |

TABLE 21

Reaction procedure for detection of DNA residues by qPCR

| Steps | Temperature | Duration | Cycle numbers |
|---|---|---|---|
| predenaturation | 95° C. | 2 min | 1 |
| denaturation | 95° C. | 10 s | 40 |
| Annealing | 60° C. | 30 s | |

9) RNA copy number and DNA residues were detected by ddPCR, and the amount of each component added was 2×ddPCR Supermix 10 μL, Primer mix 900 nM, Probe 250 nM, RNA 2 μL, DEPC H₂O to 20 μl, and the reaction procedure was shown in Table 22.

TABLE 22

Reaction procedure for detecting RNA copy number and DNA residues by ddPCR

| Steps | Temperature | Duration | Cycle numbers | Reaction rate |
|---|---|---|---|---|
| Predenaturation | 95° C. | 10 min | 1 | 2° C./sec |
| Denaturation | 94° C. | 30 s | 40 | |
| Annealing/Extension | 60° C. | 1 min | | |
| Heat inactivation | 98° C. | 10 min | 1 | |
| holding | 4° C. | Infinite | 1 | |

10) RNA amplification efficiency was detected by RT-qPCR, and the amount of each component was 5×1-step Tagman mix 4 μl, primers and Probe Mix (10 μM) 0.25 μl, RNA 2 μl, DEPC H₂O to 20 μl, and the reaction procedure was shown in Table 23.

TABLE 23

Reaction procedure for detection of RNA amplification efficiency by RT-qPCR

| Steps | Temperature | Duration | Cycle numbers |
|---|---|---|---|
| reverse transcription | 50° C. | 10 min | 1 |
| Predenaturation | 95° C. | 2 min | 1 |
| Denaturation | 95° C. | 10 s | 40 |
| Annealing/Extension | 60° C. | 30 s | |

3. Experimental Results

1) DNA Residues of RNA Standards were Detected According to Table 24

TABLE 24

Detection Results of DNA Residues for RNA Standards

| Detection gene | ORF1ab-FAM | S-FAM |
|---|---|---|
| qPCR (Ct) | 35.6 | 35.6 |
| ddPCR(Copies) | 0 | 8 |

Compared with RNA, the residual rate of plasmid after DNase I digestion was less than 1/10,000, which had no effect on the quantitative analysis of RNA reference standard.

2) RNA Copy Number Quantification

ORF1ab-FAM was selected for RNA copy number quantification, as shown in FIG. 11. The total copy number of each aliquoted RNA target gene (lab) after mixing was 1.75×10⁷ Copies.

FIG. 11. One-dimensional map of ddPCR droplets. Blue droplets are positive droplets, gray droplets are negative droplets, and red is the baseline. The abscissa represents the number of droplets, and the ordinate represents the fluorescence intensity.

Figure 12:
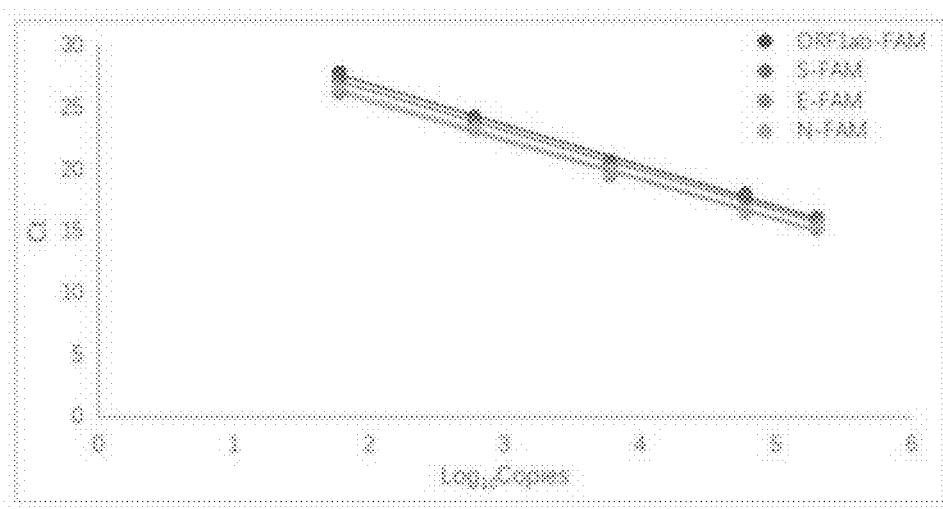
FIG. 12 is a graph of RNA amplification efficiency. The abscissa represents $Log_{10}Copies$, wherein Copies are 200000, 100000, 10000, 1000, or 100, and the ordinate represents Ct.

3) RNA Amplification Efficiency was Shown in Table 25 and FIG. 12.

TABLE 25

| RNA Copies | Log$_{10}$Copies | ORF1ab-FAM | S-FAM | E-FAM | N-FAM |
|---|---|---|---|---|---|
| | | RNA amplification efficiency | | | |
| 200000 | 5.30 | 16.05 | 15.80 | 15.19 | 15.41 |
| 100000 | 5.00 | 16.94 | 16.73 | 15.77 | 16.25 |
| 10000 | 4.00 | 20.19 | 19.61 | 18.93 | 19.24 |
| 1000 | 3.00 | 23.08 | 22.66 | 21.85 | 22.45 |
| 100 | 2.00 | 27.03 | 26.59 | 25.89 | 26.06 |
| | E | 1.02 | 1.05 | 1.04 | 1.05 |

FIG. 12 was a graph of RNA amplification efficiency. The abscissa represents Log$_{10}$Copies, wherein Copies are 200000, 100000, 10000, 1000, 100, and the ordinate represents Ct.

Example 8 cDNA Preparation and Quality Analysis

1. Experimental Materials

Reagents: DNase I (NEB 2 U/μl), 5×BlazeTaq™ Probe qPCR Master Mix (with ROX) (Genecopoeia, Cat. QP036), 5×FL SureScript™ RT buffer (Genecopoeia), 10×RTase Mix (S+M) (Genecopoeia), ddPCR™ Supermix for Probes (No dUTP) (Bio-rad), DEPC treated water, PD-10 Desalting Columns (GE Healthcare Life Sciences), FAM-labeled probes (Invitrogen), pipette tips (Axygen), 50 ml centrifuge tube (BIOFIL), 1.5 ml centrifuge tube (AXYGEY), 200 μl PCR tube (SARSTEDT), MicroAmp Optical 96-Well Reaction Plate (ABI).

2. Experimental Steps (1) The mock virus RNA (100 ng/μl, 50 μl/tube) stored at −80° C. was melted on ice, mixed by vortexing, and centrifuged briefly for the DNA in Dnase I-digested RNA; the digestion system was prepared according to Table 26 in a fume hood, and the prepared system was centrifuged briefly and then digested in a water bath. The DNase I digestion procedure was shown in Table 27. The digested system was mixed by vortexing, and centrifuged briefly for use.

TABLE 26

DNA Digestion System

| Components | 1 × Volume |
|---|---|
| 10 × Dnase I buffer | 8 μl |
| DNase I(2 U/μl) | 14 μl |
| Mock virus RNA(100 ng/μl) | 50 μl |
| DEPC treated water | 8 μl |

TABLE 27

DNA Digestion Procedure

| Reaction temperature | Duration |
|---|---|
| 37° C. | 15 min |
| 75° C. | 15 min |

(2) the reverse transcription system was prepared in 38 200 μl PCR tubes (RNase and DNase-free), according to Table 28 in a fume hood; the prepared system was centrifuged and then subjected to normal PCR machine, and reverse transcription according to the procedure in Table 29. The system after reverse transcription was mixed by vortexing, and centrifuged briefly for use.

TABLE 28

RNA reverse transcription system

| Components | 1 × Volume |
|---|---|
| 5 × FL SureScript ™ RT buffer | 4 μl |
| 10 × RTase Mix(S + M) | 2 μl |
| DNase I digested RNA | 2 μl |
| DEPC treated water | 12 μl |
| Total volume | 20 μl |

TABLE 29

RNA reverse transcription procedure

| Reaction temperature | Duration |
|---|---|
| 25° C. | 5 min |
| 45° C. | 60 min |
| 85° C. | 5 min |

(3) All reverse transcription products in 38 tubes were collected in a 1.5 ml centrifuge tube (RNase and DNase-free) in a fume hood, mixed by vortexing, and centrifuged briefly.

(4) 500 μl of reverse transcribed cDNA samples were taken and purified by P10 column gel filtration chromatography in a fume hood. The specific purification steps were as follows:

1) The P10 column was fixed on a test tube rack, and the bottom of the column was cut with alcohol-sterilized scissors;

2) 1 mL of 1×TE Buffer was added to the center of column to balance the column, and the effluent was discarded in a waste tank (repeated for 5 times);

3) 1 mL of 1× Dilution Buffer was added to the center of column, and the effluent was discarded in a waste tank;

4) 1 mL of 1×TE Buffer was added to the center of column, and the effluent was discarded in a waste tank (repeated for 6 times);

5) After there were no effluent from the column, 500 μl cDNA sample was added to the center of column;

6) 500 μl 1×TE Buffer was slowly added around the column, and the eluate was collected with a 1.5 mL centrifuge tube at the same time, which was marked as Tube No. 1;

7) 500 μl 1×TE Buffer was slowly added around the column, and the eluate was collected with a 1.5 mL centrifuge tube at the same time, which was marked as Tube No. 2;

8) The above step of collecting the eluate was repeated until Tube No. 20, and the eluates were marked as Tube No. 1, 2, 3, . . . , 18, 19, 20, respectively;

9) Tubes No. 5, 6 and 7 were mixed into one tube (marked as cDNA Mix), mixed well by vortexing, and centrifuged briefly.

(5) 50 μl of cDNA Mix was subjected to ddPCR to detect the copy number, wherein the specific steps of ddPCR were as follows:

1) cDNA Mix was diluted by 100-fold: 20 μl cDNA Mix+180 μl 1×TE buffer, mixed well by vortexing, and centrifuged briefly.

2) The ddPCR™ Supermix for Probes (No dUTP) was thawed at room temperature, mixed well by turning upside down and centrifuged briefly;

3) ddPCR Reaction Mix (FAM/HEX dual channel) was prepared according to Table 30.

TABLE 30

| ddPCR reaction system | | |
|---|---|---|
| Components | 1 × Volume | Final concentration |
| 2 × Supermix for Probes (No dUTP) | 10 μL | 1× |
| ORF1ab Primer Mix (10 μM) | 1.8 μL | 0.9 μM |
| ORF1ab Taqman Probe (5 μM) | 1 μL | 0.25 μM |
| Diluted cDNA | 2 μL | |
| ddH₂O | Added to 20 μL | |
| Total volume | 20 μL | |

4) After the prepared system was mixed well by shaking and centrifuged, it was carefully transferred to sample wells in the middle row of the droplet generation card, and 70 μL of droplet generator oil was added to the well in the lower row, and then droplets were generated in a droplet generator.

5. The generated droplet sample (40 μL) was transferred from the upper row of the droplet generation card to a ddPCR-dedicated 96-well plate, and then the 96-well plate was sealed with a PX1 heat sealer after covered with aluminum film.

6) After sealing the plate, the PCR reaction should be carried out within 30 minutes, or the PCR should be carried out within 4 hours in a 4° C. refrigerator. The PCR procedure was shown in Table 31, wherein the rate of increase or decrease of the temperature was 2° C./s.

TABLE 31

| PCR Reaction Procedure | | | |
|---|---|---|---|
| Steps | Temperature | Duration | Cycle numbers |
| Predenaturation | 95° C. | 10 min | 1 |
| Denaturation | 94° C. | 10 s | 40 |
| Annealing | 60° C. | 20 s | |
| Extension | 72° C. | 15 s | |
| Enzyme inactivation | 98° C. | 4 min | 1 |
| maintain temperature | 4° C. | ∞ | |

7) After PCR, the 96-well plate was taken out and the droplets on a droplet reader were read.

8) After reading of the droplets, the data were analyzed by a Bio-rad QuantaSoft software.

9) Based on the ddPCR results, the cDNA Mix (1.18×10⁵ copies/μl) was thawed on ice, mixed well and centrifuged, and was diluted to cDNA Standard #1 (wherein cDNA concentration was 1×10⁵ copies/μl) by using 1×TE buffer: 1000 μl cDNA Mix+180 μl 1×TE buffer, mixed well by turning upside down and centrifuged briefly. Then cDNA Standard #1 was serially diluted by 1×TE buffer.

The specific steps of dilution were as follows:

1) cDNA Standard #2-1 (5×10⁴ copies/μl): 50 μl cDNA Standard #1+50 μl 1×TE buffer;

2) cDNA Standard #2-2 (5×10³ copies/μl): 20 μl cDNA Standard #2-1+180 μl 1×TE buffer;

3) cDNA Standard #2-3 (5×10² copies/μl): 20 μl cDNA Standard #2-2+180 μl 1×TE buffer;

4) cDNA Standard #2-4 (5×10 copies/μl): 20 μl cDNA Standard #2-3+180 μl 1×TE buffer;

5) The sample of cDNA Standard #2 was subjected to qPCR to detect the amplification efficiency according to the system and procedure as shown in Table 32 and Table 33.

TABLE 32

| qPCR reaction system | |
|---|---|
| Components | 1 × Volume |
| 5 × BlazeTaq ™ Probe qPCR Master Mix | 4 μl |
| ORF1ab/N/S/E primers and Probe (10 μM) | 0.25 μl |
| cDNA sample diluted in gradient | 2 μl |
| ROX (30 μM) | 0.1 μl |
| DEPC treated water | 12 μl |

TABLE 33

| qPCR reaction procedure | | |
|---|---|---|
| Reaction temperature | Duration | Cycle numbers |
| 95° C. | 2 min | 1 |
| 95° C. | 10 s | 40 |
| 60° C. | 30 s | |

3. Experimental Results (1) ddPCR Results of cDNA Mix 1) ddPCR Original Droplet Data were Shown in FIG. 13.

Figure 13:
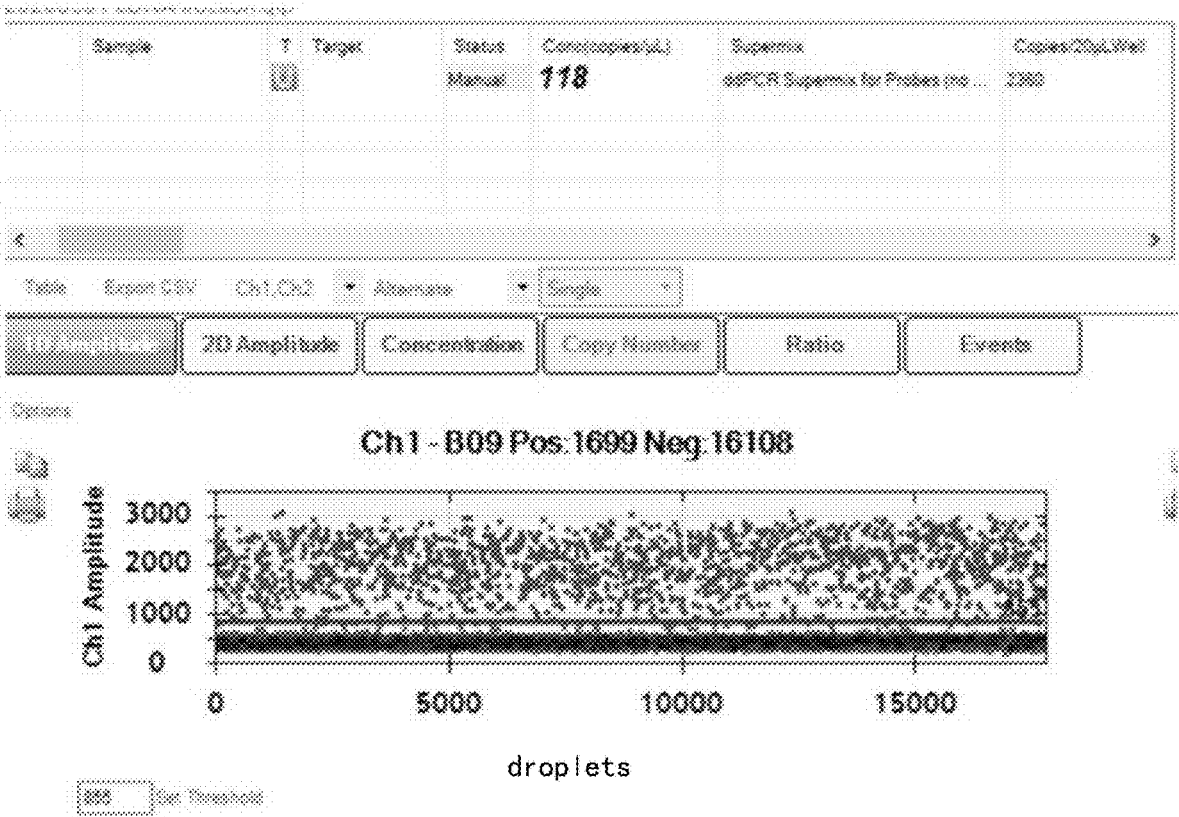
FIG. 13 is a graph of ddPCR original droplet data, the abscissa represents the number of droplets, and the ordinate represents the fluorescence intensity. Taking ORF1ab as a detection target, 2 ul template was added for reaction, and the number of positive droplets is 2360 copies.

FIG. 13 is a graph of ddPCR original droplet data, wherein the abscissa represents the number of droplets, and the ordinate represents the fluorescence intensity. Taking ORF1ab as a detection target, 2 ul template was added for reaction, and the number of positive droplets is 2360 copies.

2) Calculation Result:

TABLE 34

| Calculation of cDNA Mix concentration based on ddPCR data | |
|---|---|
| Samples | Calculation process and final concentration |
| cDNA Mix concentration after dilution by 100-fold | 2360 ÷ 2 = 1180 copies/μl |
| cDNA Mix stock solution concentration | 1180 × 100 = 1.18 × 10⁵ copies/μl |

Note:
cDNA Mix was a mixture of cDNA in Tubes No. 5, 6 and 7.

(2) Amplification Efficiency Results of qPCR for Each Gradient of cDNA Standard #2:

1) Ct value, wherein the calculation process was shown in Table 10

TABLE 35

| Ct Values of cDNA Standard #2 Gradient qPCR | | | | | |
|---|---|---|---|---|---|
| Copies | Log₁₀ (Copies) | ORF1ab-FAM | S-FAM | E-FAM | N-FAM |
| 2 × 10⁵ | 5.30 | 19.7 | 19.5 | 17.9 | 19.5 |
| 1 × 10⁵ | 5.00 | 20.8 | 20.1 | 18.8 | 20.4 |
| 1 × 10⁴ | 4.00 | 24.0 | 23.5 | 22.2 | 23.6 |
| 1 × 10³ | 3.00 | 27.6 | 27.2 | 25.9 | 27.0 |
| 1 × 10² | 2.00 | 31.2 | 30.7 | 29.2 | 30.5 |
| R² | | 0.9995 | 0.9983 | 0.9993 | 0.9995 |
| E | | 94.2% | 94.8% | 94.5% | 99.5% |

Note:
E = 10^[(−1/slope)−1]

The standard curve of cDNA Standard #2 gradient qPCR was shown in FIGS. 14-17.

Figure 14:
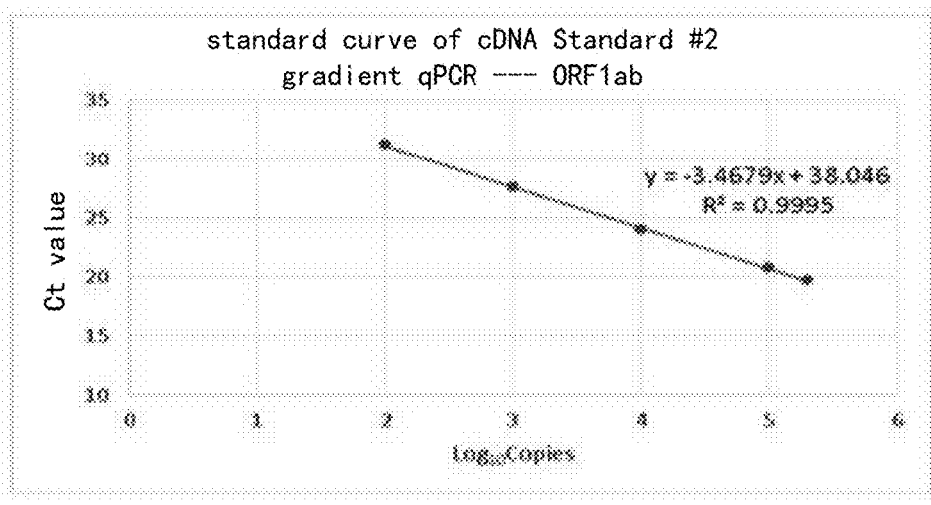
FIG. 14 is the standard curve of cDNA Standard #2 gradient qPCR-ORF1ab, wherein the abscissa is $Log_{10}Copies$, and the ordinate is Ct value.

FIG. 14, standard curve of cDNA Standard #2 gradient qPCR-ORF1ab, wherein the abscissa is $Log_{10}Copies$, and the ordinate is Ct value.

Figure 15:
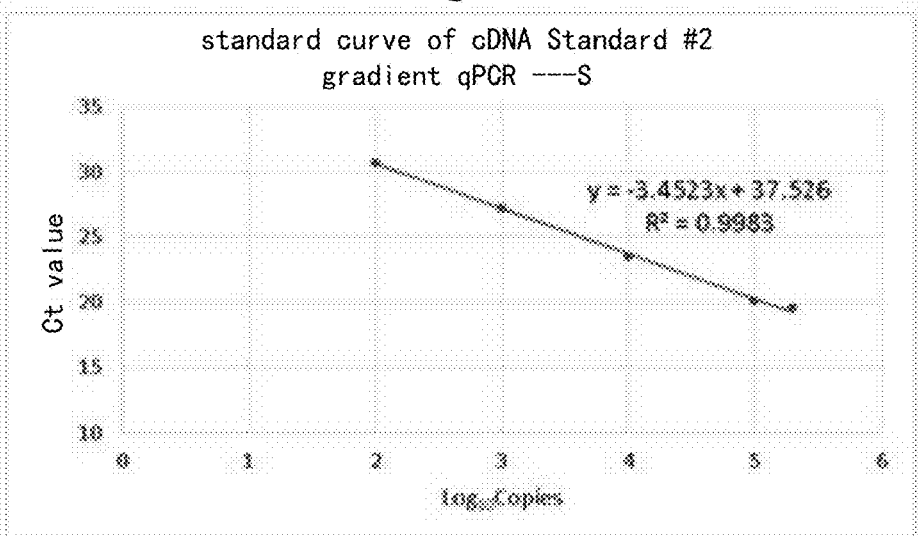
FIG. 15 is the standard curve of cDNA Standard #2 gradient qPCR-S, wherein the abscissa is $Log_{10}Copies$, and the ordinate is Ct value.

FIG. 15, standard curve of cDNA Standard #2 gradient qPCR-5, wherein the abscissa is $Log_{10}Copies$, and the ordinate is Ct value.

Figure 16:
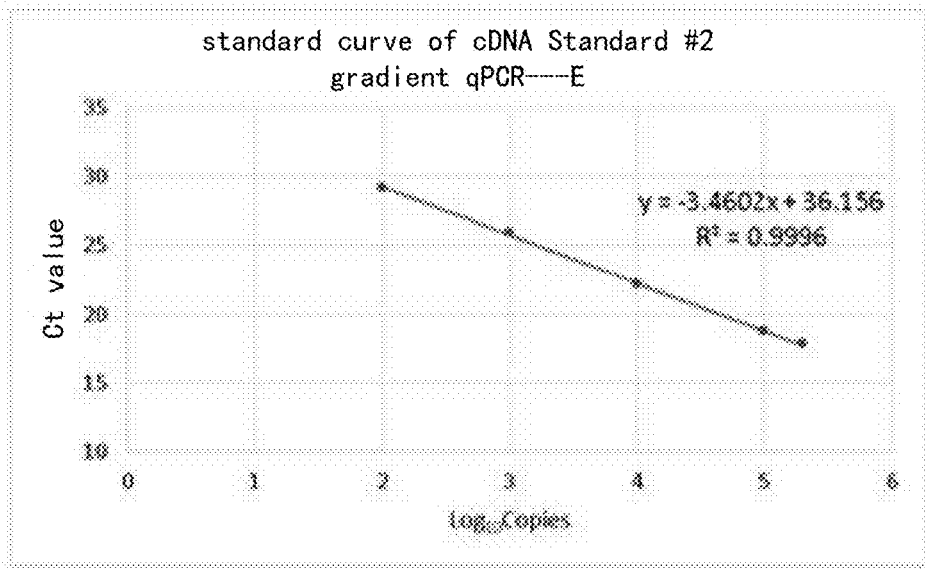
FIG. 16 is the standard curve of cDNA Standard #2 gradient qPCR-E, wherein the abscissa is $Log_{10}Copies$, and the ordinate is Ct value.

FIG. 16, standard curve of cDNA Standard #2 gradient qPCR-E, wherein the abscissa is $Log_{10}Copies$, and the ordinate is Ct value.

Figures 17, 18:
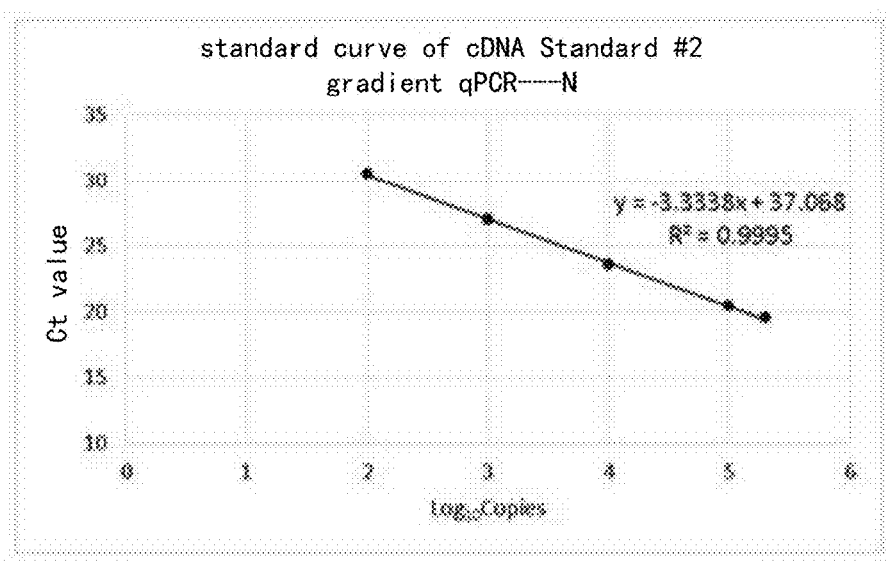
FIG. 17 is the standard curve of cDNA Standard #2 gradient qPCR-N, wherein the abscissa is $Log_{10}Copies$, and the ordinate is Ct value.
FIG. 18 is an amplification curve of each gene. a, amplification curve of ORF1ab-FAM gene, wherein the abscissa is cycle number, and the ordinate is ΔRn (ΔRn is the normalized result after subtracting the baseline from Rn); b, the amplification curve of N-FAM gene, wherein the abscissa is cycle number, and the ordinate is ΔRn; c, amplification curve of S-FAM gene, wherein the abscissa is cycle number, and the ordinate is ΔRn; d, amplification curve of E-FAM gene, wherein the abscissa is cycle number, and the ordinate is ΔRn.

FIG. 17. Standard curve of cDNA Standard #2 gradient qPCR-N, wherein the abscissa is $Log_{10}Copies$, and the ordinate is Ct value.

2) The amplification curve of each gene was shown in FIG. 18.

FIG. 18 is an amplification curve of each gene. a, amplification curve of ORF1ab-FAM gene, wherein the abscissa is cycle number, and the ordinate is ΔRn (ΔRn is the normalized result after subtracting the baseline from Rn); b, the amplification curve of N-FAM gene, wherein the abscissa is cycle number, and the ordinate is ΔRn; c, amplification curve of S-FAM gene, wherein the abscissa is cycle number, and the ordinate is ΔRn; d, amplification curve of E-FAM gene, wherein the abscissa is cycle number, and the ordinate is ΔRn.

Example 9: Amplification Efficiency of Spike-in Standards

1. Experimental Materials
   Reagent: GeneCopoeia BlazeTaq SYBR Green qPCR mix
   Equipment: ABI ViiA 7 qPCR instrument
2. Experimental Steps
   1) According to the pre-experimental results of "mock virus" cDNA and "spike-in mock virus" cDNA and referring to the quantitation data of ddPCR, the two cDNAs were diluted by 10-fold gradient in a biological safety cabinet to obtain test samples of $10^5$ copies/uL to $10^2$ copies/uL
   2) The system for dye-based qPCR reaction was prepared in a biological safety cabinet, and the targets to be tested were ORF1ab, S, E, and N; the system was shown in Table 36

TABLE 36

| qPCR reaction system | |
| --- | --- |
| Components | Volume |
| 5 × BlazeTaq SYBR Green qPCR mix | 4 μL |
| Primer Mix 2 μM) | 2 μL |
| cDNA ($10^5$~$10^2$ copies/μL) | 5 μL |
| ddH$_2$O | 9 μL |
| Total | 20 μL |

3) After the system was completely prepared, qPCR quantitative detection and melting curve analysis were performed on a qPCR instrument (ABI ViiA7). The qPCR reaction procedure and melting curve procedure were shown in Table 37 and Table 38 respectively:

TABLE 37

| qPCR reaction procedure | | |
| --- | --- | --- |
| Temperature | Duration | Cycle numbers |
| 95° C. | 30 s | 1 |
| 95° C. | 10 s | 40 |
| 58° C. | 10 s | |
| 68° C. | 20 s | |

TABLE 38

| Melting curve procedure | | |
| --- | --- | --- |
| Temperature | temperature Interval | Duration |
| 95° C.→60° C. | 1.6° C. | 1 sec/each |

4) The amplification efficiencies of different targets of various cDNAs were calculated according to the Ct value of serially diluted samples. The results were shown in Table 39.

TABLE 39

Calculation of amplification efficiencies of four SARS-Cov-2 targets in "mock virus cDNA" and "spike-in mock virus cDNA"

| CDNA | "mock virus" cDNA | | | | "spike-in mock virus" cDNA | | | |
| --- | --- | --- | --- | --- | --- | --- | --- | --- |
| Target | ORF1ab | S | E | N | ORF1ab | S | E | N |
| 500,000 | 21.8 | 22.50 | 21.1 | 21.0 | 21.43 | 22.83 | 21.28 | 20.77 |
| 50,000 | 25.8 | 26.01 | 25.3 | 23.9 | 25.77 | 26.00 | 25.05 | 23.88 |
| 5,000 | 28.8 | 31.00 | 28.6 | 27.0 | 28.56 | 30.43 | 28.67 | 27.41 |
| 500 | 32.6 | 34.50 | 32.5 | 30.5 | 32.91 | 34.75 | 32.78 | 30.89 |
| NTC | NA | NA | NA | NA | NA | NA | NA | NA |
| Amplification efficiency | 91.6% | 75.3% | 84.7% | 107% | 85.7% | 77.8% | 83.0% | 97.6% |
| $R^2$ | 0.997 | 0.995 | 0.998 | 0.998 | 0.998 | 0.994 | 0.999 | 0.999 |
| specificity | high | low | high | high | high | low | high | high |

Figure 19:
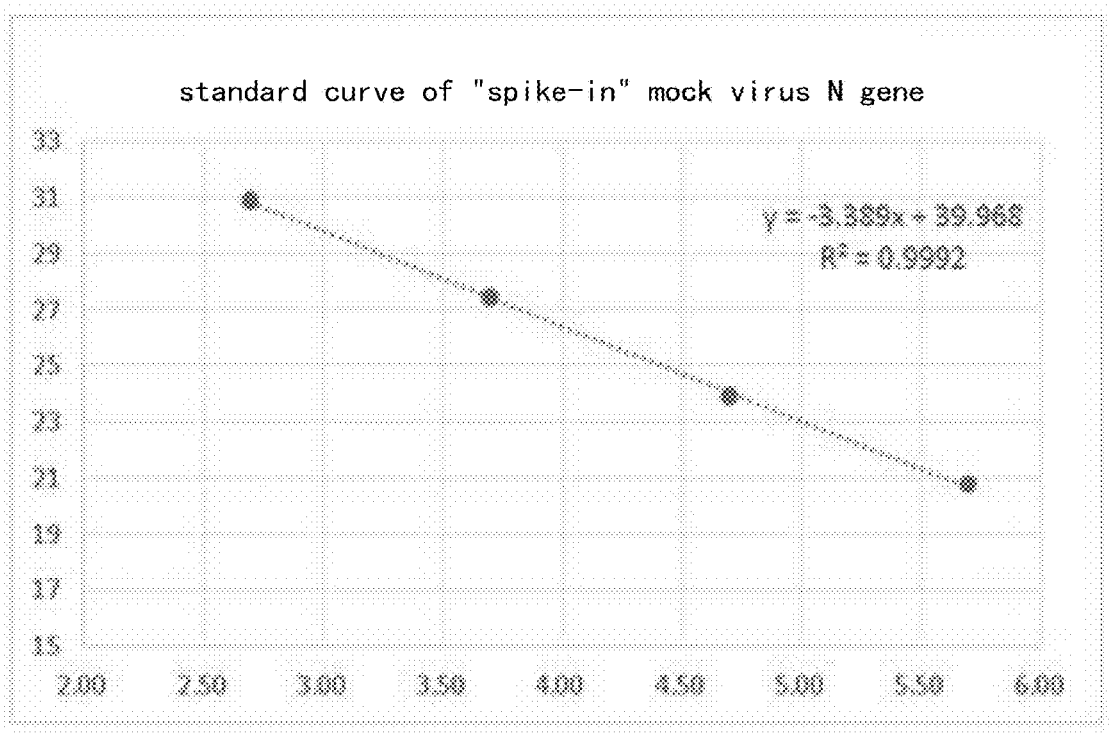
FIG. 19 shows calculation of copy number concentration of the "spike-in" mock virus N gene from a standard curve of Ct value versus copy number.
Figure 20:
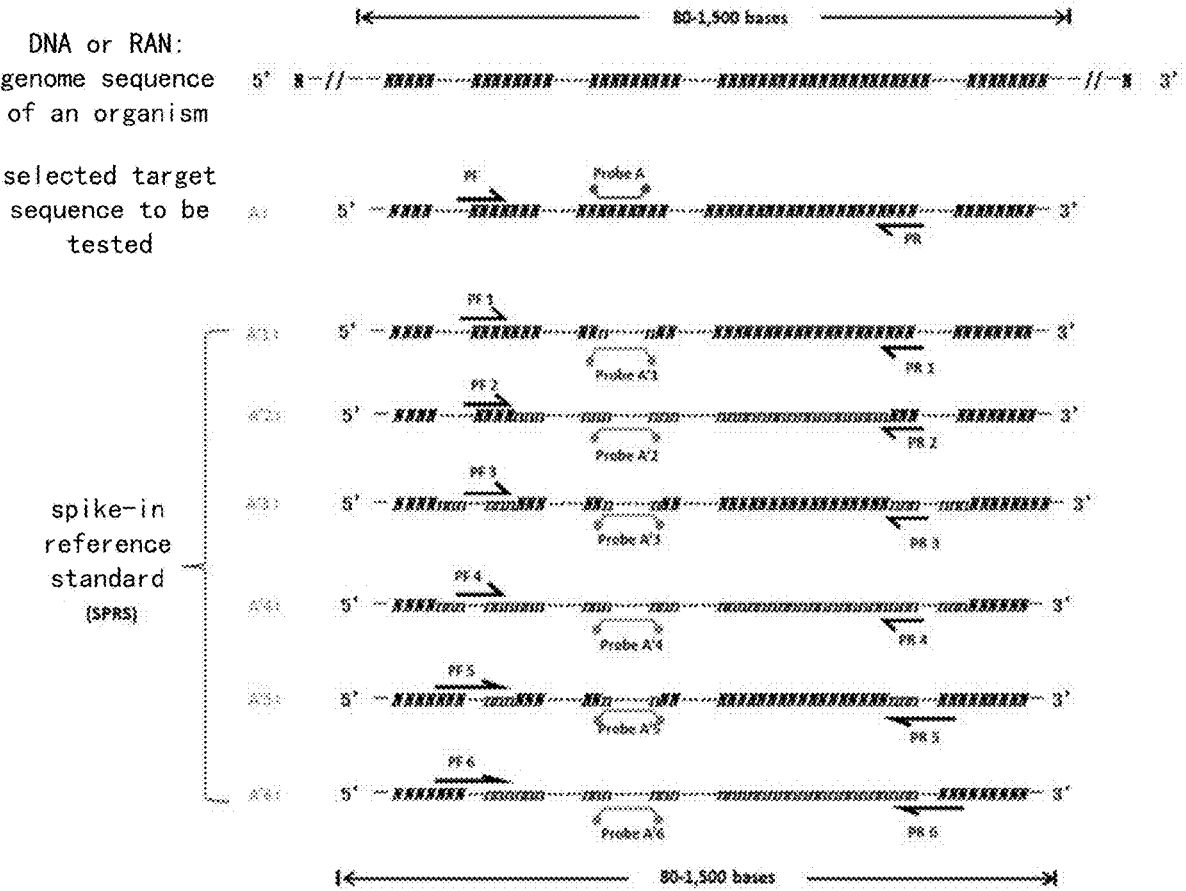
FIG. 20 shows a schematic diagram of the design of the quantitative detection nucleic acid fragments of the present invention. Methods for designing positive standards for all species of known DNA or RNA sequence that can be spiked into the test sample or sample collection device (tube).
Figures 21, 22:
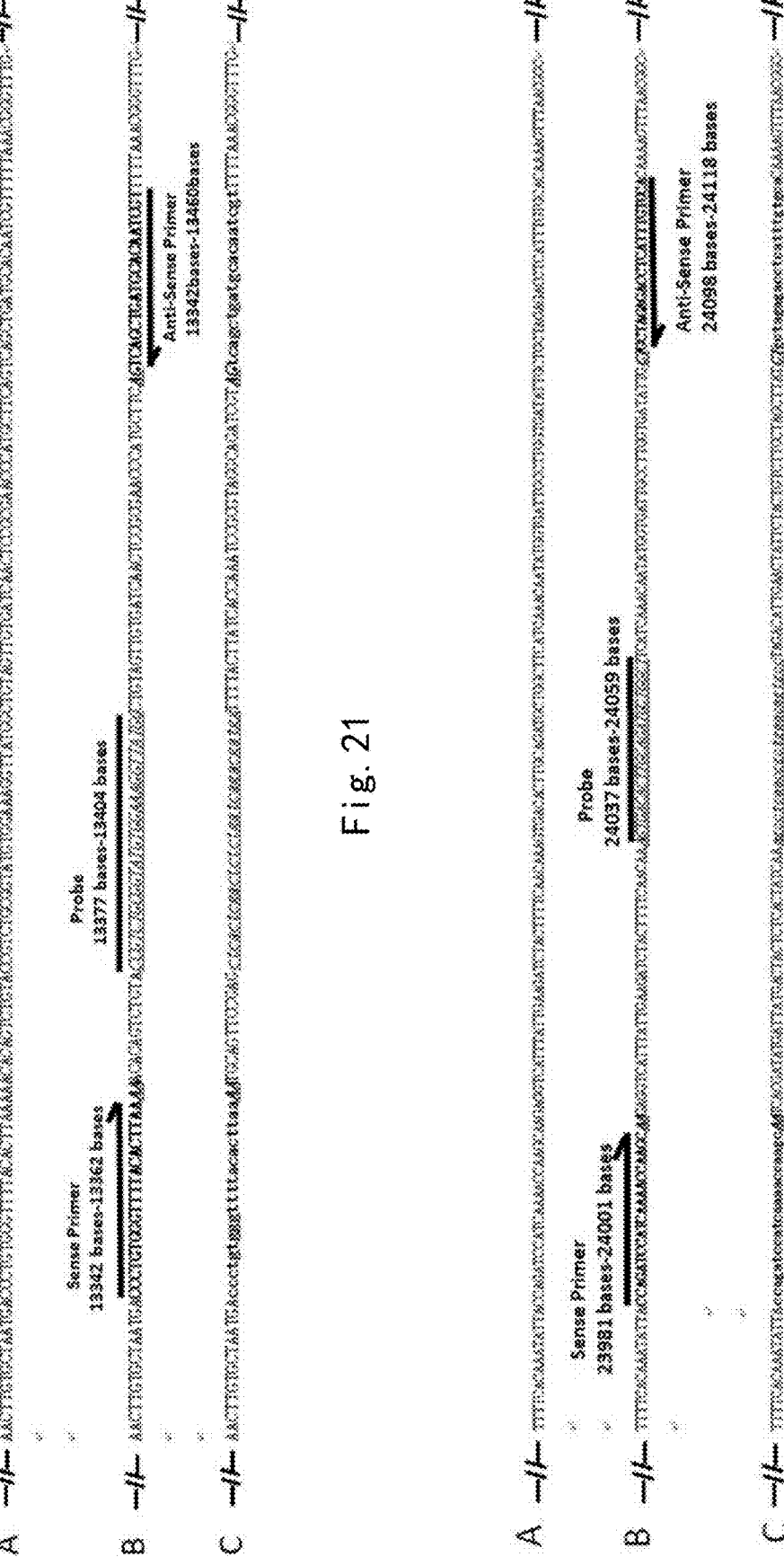
FIG. 21 exemplarily shows a schematic diagram of the design of the quantitative detection nucleic acid fragment of the present invention by taking the orf1ab gene of SARS-CoV-2 recommended by the Chinese CDC as an example; wherein, A represents the RNA sequence of wild-type SARS-CoV-2 (2019-nCoV RNA Sequence); B represents the SARS-CoV-2 RNA sequence (Amplicon for Virus target detection) selected as the nucleic acid target sequence of test sample, wherein the underlined sequence represents sequence complementary to the probe, and the two arrows respectively represent upstream and downstream primers used to amplify the nucleic acid target sequence of test sample; C represents the RNA sequence containing the quantitative detection nucleic acid fragment of the present invention (Selected amplicon for positive reference), wherein the underline represents sequences complementary to the probe, as can be seen from the sequence shown in C, the 5' and 3' ends of the quantitative detection nucleic acid fragments are the same as the corresponding 5' and 3' ends of the nucleic acid target sequence of test sample, and the length of identical sequences is the sum of the lengths of the 5'-end primer and the 3'-end primer used for amplifying the nucleic acid target sequence of the test sample and the lengths of the 2 bases downstream of the 5'-end primer and the 2 bases upstream of the 3'-end primer, respectively.
FIG. 22 exemplarily shows a schematic diagram of the design of the quantitative detection nucleic acid fragment of the present invention by taking the spike protein-encoding gene of SARS-CoV-2 elected by the present invention as an example.

FIG. 19, copy number concentration of the "spike-in" mock virus N gene is calculated from a standard curve of Ct value versus copy number.

Remarks for FIG. 19: An X-Y scatter point plot was drawn by using the logarithm of copy number as an abscissa and the Ct value as an ordinate. Linear fitting was performed on a series of points, and the amplification efficiency E was calculated according to the slope k of the trend line: E=(10^(−1/k)−1)×100%.

Example 10: Effect of the Amount of Added "Spike-In Mock Virus" cDNA on the Quantitative Results of SARS-CoV-2 Target in the "Mock Virus" cDNA 1. Experimental Materials
   Reagent: GeneCopoeia BlazeTaq qPCR mix for Probes
2. Experimental Steps
   1) The copy number concentrations of the two targets, ORF1ab and S, were estimated according to target quantification results of "spike-in mock virus" cDNA by dye-based qPCR.
   2) In a biological safety cabinet, "spike-in mock virus" cDNAs having various concentration gradients ($5\times10^5$ copies to 50 copies) were added to the "mock virus" cDNA used as detection kit raw materials and quality control.
   3) the system of probe-based qPCR reaction was prepared in a biological safety cabinet, and the targets were ORF1ab and S; the qPCR system was the same as that in the probe-based qPCR kit instruction.
3. The Experimental Results were Shown in FIG. 23.

Figure 23:
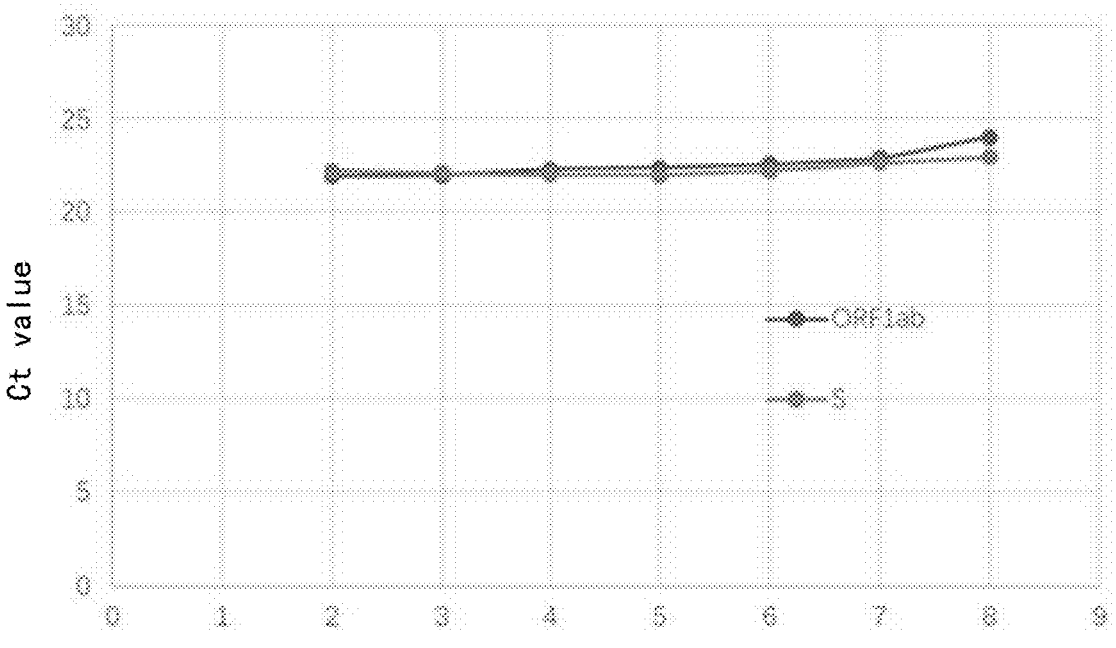
FIG. 23 shows the effect of the amount of added "spike-in mock virus" cDNA on the quantitative results of SARS-CoV-2 target in the "mock virus" cDNA. The abscissa is the logarithm of the amount of "spike-in mock virus" cDNA added, and the ordinate is the Ct value of ORF1ab and S targets in the "mock virus" cDNA.
Figure 24:
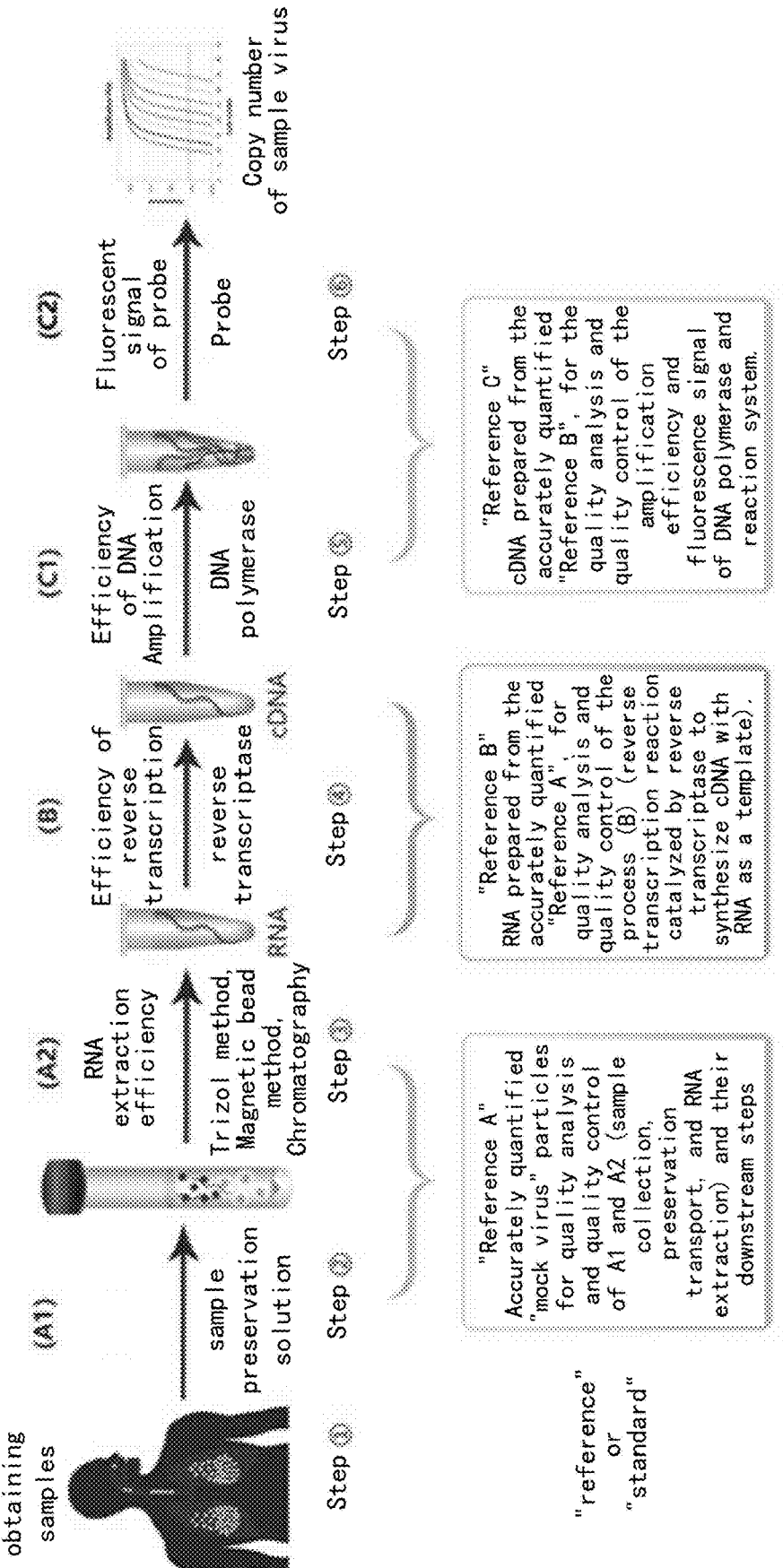
FIG. 24 shows raw materials of the SARS-CoV-2 nucleic acid detection kit and "quality controls" used for quality analysis and quality control in the production process of the kit.
Figure 25:
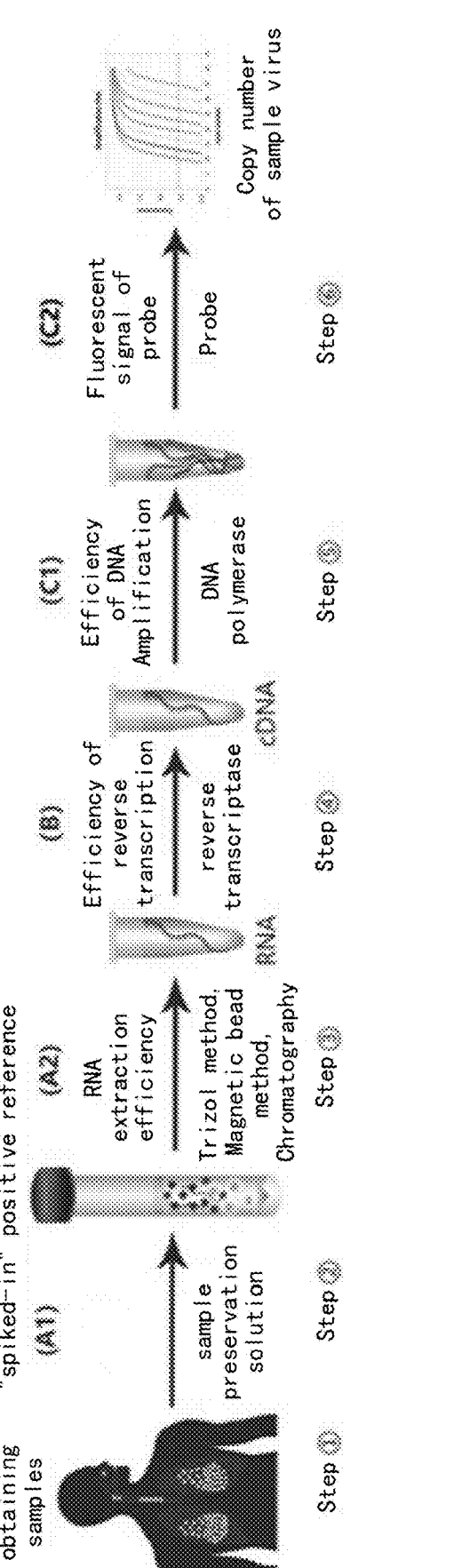
FIG. 25 shows a SARS-CoV-2 nucleic acid detection kit (quantitative).

FIG. 23, effect of the amount of added "spike-in mock virus" cDNA on the quantitative results of SARS-CoV-2 target in the "mock virus" cDNA. The abscissa was the logarithm of the amount of "spike-in mock virus" cDNA added, and the ordinate was the Ct value of ORF1ab and S targets in the "mock virus" cDNA.

Example 11: Specific Method v for Lentivirus Quantification: The Copy Number Concentration of N and S Genes in the RNA of "Mock Virus" Spike-In Standard was Detected by One-Step RT-ddPCR Method 1. Experimental Materials
   Reagent: BIO-Rad One-STEP RT-ddPCR Advanced Kit for Probes
   Equipment: Bio-Rad QX200 droplet digital PCR System
2. Experimental Steps
   1. The "mock virus" spike-in standard RNA was diluted with ddH₂O (DNase-free) by 100-fold, and then diluted by 10-fold to obtain two gradients, thereby obtaining 3 test samples for RT-ddPCR;
   2. All components of BIO-Rad One-STEP RT-ddPCR Advanced Kit for Probes were dissolved at room temperature, mixed well by turning upside down and centrifuged briefly;
   3. RT-ddPCR Reaction Mix was prepared according to Table 40

TABLE 40

| RT-ddPCR reaction system | | |
| --- | --- | --- |
| component | amount/μL | Final concentration |
| Supermix | 5 | 1× |
| Reverse Transcriptase | 2 | 20 U/μL |

TABLE 40-continued

| RT-ddPCR reaction system | | |
| --- | --- | --- |
| component | amount/μL | Final concentration |
| 300 mM DTT | 1 | 15 mM |
| Primer Mix (10 μM) | 1.8 | 0.9 μM |
| Taqman Probe (5 μM) | 1 | 0.25 μM |
| RNA | 1 | |
| ddH₂O | Added to 20 | |
| Total volume | 21 | |

4. After the prepared system was mixed well by shaking and centrifuged, it was carefully transferred to the sample wells in the middle row of the droplet generation card, and 70 μL of droplet generation oil was added to the well in the lower row, and then droplets were generated in a droplet generator.
5. The generated droplet sample (40 μL) was transferred from the upper row of the droplet generation card to a ddPCR-dedicated 96-well plate, the 96-well plate was sealed with a PX1 heat sealer after covered with an aluminum film.
6. After sealing the plate, the PCR reaction was performed within 30 minutes, or within 4 hours in a 4° C. refrigerator. The PCR reaction should be carried out according to Table 17, and the rate of temperature increase or decrease was set to be 2° C./sec.

TABLE 41

| PCR reaction | | | |
| --- | --- | --- | --- |
| Steps | Temperature | Duration | Cycle numbers |
| reverse transcription | 42° C. | 60 min | 1 |
| Enzyme activation | 95° C. | 10 min | 1 |
| denaturation | 95° C. | 30 s | 40 |
| Annealing/Extension | 60° C. | 1 min | |
| Enzyme inactivation | 98° C. | 10 min | 1 |
| maintain temperature | 4° C. | ∞ | |

7. After PCR was finished, the 96-well plate was taken out and the droplets reading was carried out by the droplet reader.
8. After reading of the droplets, the data results were analyzed by a Bio-rad QuantaSoft software, and the copy number concentrations of N and S genes in the RNA of "mock virus" spike-in standard were calculated, as shown in FIG. 26.

Example 12: SARS-Cov-2 2019-nCOV Nucleic Acid Qualitative and Quantitative Detection Kit (Fluorescent PCR Method) and Model Detection of Spike-In Positive Standard and Quality Control RNA Based on one-step RT-PCR technology (RNA reversal transcription reaction and polymerase chain reaction (PCR) in combination with TAQMAN technology), 2019-nCOV N gene and S gene-specific conservative sequences were selected as amplification target area; specific primers and fluorescent probes (HEX markers for N gene probes, FAM markers for S gene probes) were designed for the detection of 2019-nCOV RNA in a sample; at the same time, endogenous internal control detection system (CY5 marker for internal control gene H probe, and AP593 marker for unique positive standard S gene and the N gene probe), that is, 3 pairs of primers and 4 probes, were included for qualitative and quantitative analysis of the target gene.

Standard: having the same nucleic acid sequence length, base percentage, Tm value and primers as the quality control (or targets to be tested), but having different arrangement of sequence fragments.

1. Experimental Materials
1.1. Instrument
 PCR Instrument: ABI viia7
 Centrifuge: labnet, C1301
 Biological Safety Cabinet: Suzhou Jinghua Company
1.2. Consumptions
 96-well plate: ABI, N8010560
1.3. Reagent
 RNAzol® RT RNA Isolation Reagent: Guangzhou iGene
  Biotechnology Co., Ltd, QP020
 Dnase I: NEB, M0303L
 Primers: see Table 42
 TAQMAN probe: see Table 43

TABLE 42

Primer sequences and related information

| Target gene | Primer name | Sequence |
|---|---|---|
| quality control | N (matchwith cCDC) | cCDC-N-PF2 | GGGGAACTTCTCCTG CTAGAAT (SEQ ID NO: 74) |
| | | CCDC-N-PR2 | CAGACATTTTGCTCT CAAGCTG (SEQ ID NO: 75) |
| quality control | S (matchwith FL) | FL-S-F | CCAGATCCATCAAAA CCAAGC (SEQ ID NO: 76) |
| | | FL-S-R | TGCACAAATGAGGTC TCTAGC (SEQ ID NO: 77) |
| Internal reference | House-Keeping GAPDH | GAPDH2-PF | CCTGCCACACTCAGT CCCC (SEQ ID NO: 78) |
| | | GAPDH2-PR | GACAAGGTGCGGCTC CCTA (SEQ ID NO: 79) |

TABLE 43

Probe sequence and fluorescent label information

| Target gene | Primer name | Sequence | fluorescent label |
|---|---|---|---|
| quality control | N (matchwith cCDC) | cCDC-N-Probe 1 | TTGCTGCTGCTTGACAGATT (SEQ ID NO: 80) | HEX |
| quality control | S (matchwith FL) | FL-S-Probe 1 | AGTGACACTTGCAGATGCT GGCT(SEQ ID NO: 81) | FAM |
| Internal reference | HouseKeeping GAPDH | GAPDH-Probe 2 | CACACTGAATCTCCCCTCCT CACAGTTGC(SEQ ID NO: 82) | Cy5 |
| Spike in | N (matchwith cCDC) | cCDC-N-Probe 2 | CACCGAGGATGCACAGCTC GCTCTA(SEQ ID NO: 83) | AP593 |

Note:
FL: Guangzhou Fulen Gene Co., Ltd.,
cCDC: Chinese Center for Disease Control and Prevention 2. Experimental Steps
2.1. RNA Extraction The standard RNA and quality control RNA were extracted according to the instructions of RNAzol® RT RNA Isolation Reagent kit, and finally the RNA precipitate was dissolved by 50 μL of TE buffer (herein, the TE buffer is 100 μm TE buffer prepared by DEPC-treated water, and all the RNA precipitates in the present invention were dissolved by said TE buffer).

2.2. Digestion of RNA by DNase I

The two RNAs were treated with DNase I after extraction to remove genome DNA and plasmid DNA residues in the RNA. RNA was treated with DNase I according to the reaction system in Table 44. The reaction system was centrifuged briefly after the sample was added, and then heated at 37° C. for 10 minutes, and 72° C. for 10 minutes to inactivate the DNase I, and stored at −80° C. for later use.

TABLE 44

DNase I reaction system

| Reagent | amount/μL |
|---|---|
| DEPC treated water | 10 |
| RNA | 30 |
| DNase I buffer (10×) | 5 |
| DNase I | 5 |
| Total amount | 50 |

Genome DNA and plasmid DNA residues were detected by qPCR and RT-PCR, and RNA could be used for subsequent experiments until no genes of interest was detected by qPCR which indicated that the residues were digested completely. Taking N gene target as an example, the qPCR reaction system was shown in Table 45, the RT-PCR reaction system 1 was shown in Table 46, and the running procedure was shown in Table 47.

TABLE 45 qPCR reaction system

| Components | volume/μL |
|---|---|
| (5×) two step qPCR Mix | 4 |
| 10 μM cCDC-N primer | 0.25 |
| 10 μM FL-N-AP593 | 0.25 |

TABLE 45-continued

| qPCR reaction system | |
|---|---|
| Components | volume/μL |
| ROX | 0.1 |
| DEPC treated water | 10.4 |
| RNA | 5 |

TABLE 46

| RT-PCR reaction system 1 | |
|---|---|
| Components | volume/μL |
| 5×)Probe One Step RT-qPCR Mix | 4 |
| 10 × RTase Mix | 2 |
| 10 μM cCDC-N primer | 0.25 |
| 10 μM FL-N-AP593 | 0.25 |
| ROX | 0.1 |
| DEPC treated water | 8.4 |
| RNA | 5 |

TABLE 47

| QPCR and RT-PCR running procedure | | | | |
|---|---|---|---|---|
| Number of cycles | step | Temperature | Time | Detection or not |
| 1 | reverse transcription | 50° C. | 10 min | no |
| 1 | Pre-denaturation | 95° C. | 2 min | no |
| 40 | denaturation extension | 95° C. 60° C. | 15 sec 30 sec | no yes |

2.3. Sample Dilution and Standard Curve Preparation

The clean RNA was quantified by Biorad ddPCR, and then standard curve was prepared by diluting the RNA in gradient 10 with a dilution solution (TE buffer+0.25 U/μL RNase Inhibitor+1 pg/μL ttRNA). In addition, two low-concentration copy numbers of the standard RNA were obtained by dilution and used for subsequent experiments, wherein the low concentration copy numbers were 100 Copies/μL and 12.5 Copies/μL. The specific steps of RNA dilution were shown in Table 48.

TABLE 48

| RNA dilution steps | | |
|---|---|---|
| No. | Concentration copies/μL | concentration dilution step |
| (1) | $1.0 \times 10^5$ | With a concentration of $1.0 \times 10^5$ copies/μL |
| (2) | $1.0 \times 10^4$ | 10 μL(1) added with 90 μL diluent |
| (3) | $1.0 \times 10^3$ | 10 μL(2) added with 90 μL diluent |
| (4) | 100 | 10 μL(3) added with 90 μL diluent |
| (5) | 50 | 50 μL(4) added with 50 μL diluent |
| (6) | 25 | 50 μL(5) added with 50 μL diluent |
| (7) | 12.5 | 50 μL(6) added with 50 μL diluent |

2.4. RT-PCR Detection Reaction

The diluted standard RNA was used for the drawing of standard curve; at the same time, the copy number of standard was fixed to detect the gradient of quality control. For details of the RT-PCR reaction system, please refer to Table 49. The samples were added after PCR reaction MIX (other components except for the quality control) was prepared, wherein each reaction well was added with 15 μL prepared MIX firstly, and then 5 μL quality control or test sample were added.

TABLE 49

| RT-PCR reaction system 2 | |
|---|---|
| Components | volume/μL |
| 5×)Probe One Step RT-qPCR Mix | 4 |
| 10 × BlazeTaq™ One Step RTase Mix | 2 |
| 10 μM cCDC-N primer | 0.25 |
| 10 μM cCDC N HEX | 0.25 |
| 10 μM FL-N-AP593 | 0.25 |
| 10 μM FL S Primer | 0.25 |
| 10 μM FL S FAM | 0.25 |
| 10 μM GAPDH2 primer | 0.25 |
| 10 μM GAPDH2 CY5B | 0.25 |
| Human 293T RNA | 1 |
| Standard RNA-N | 1 |
| DEPC treated water | 5.25 |
| quality control RNA | 5 |

2.5. Instrument Detection

After the samples were added, the sample signal was detected on the ABI IVVA7 with the same running procedure of Table 47, wherein quality controls or clinical sample S gene were detected in FAM channel; quality controls or clinical sample N gene were detected in VIC (HEX) channel; endogenic human GAPDH gene was detected in CY5 channel, and S gene or N gene in the standard were detected in ROX (AP593) channel.

3. Experimental Results

3.1 Drawing of Standard Curve of Standard N Gene Concentration Gradient.

Figure 27:
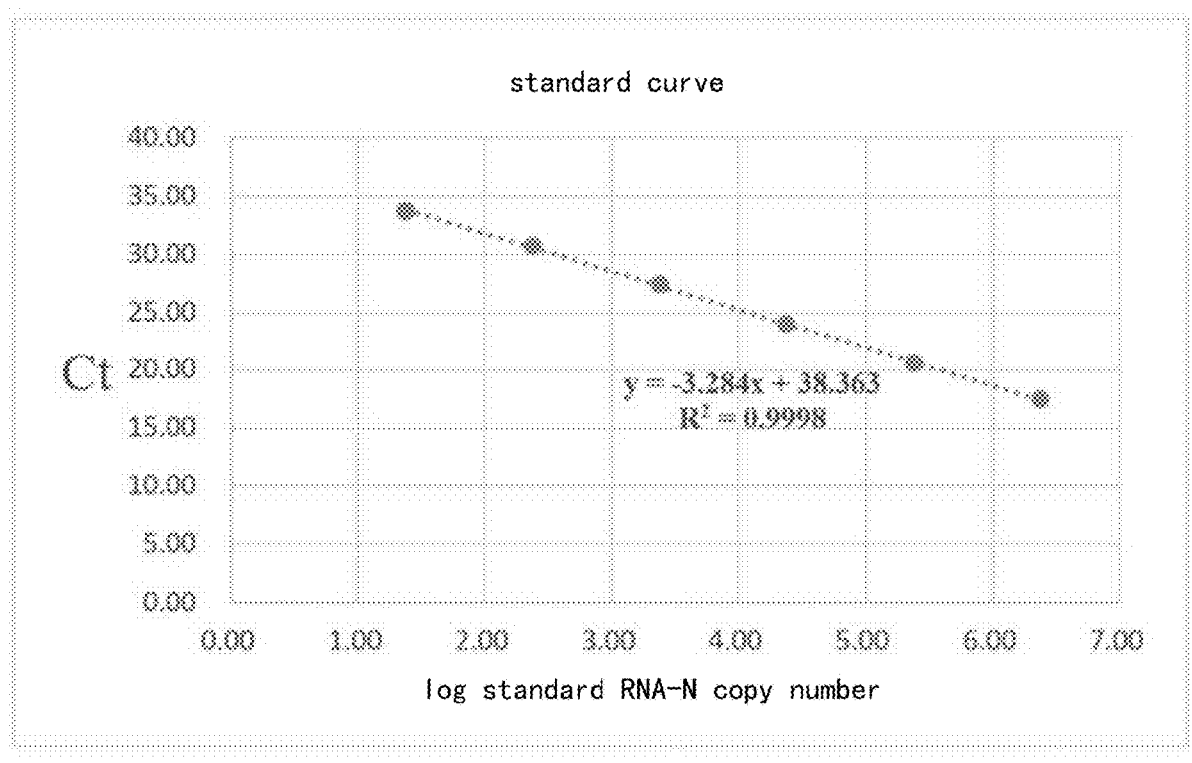
FIG. 27 shows the standard curve of standard N gene concentration gradient.
Figure 28:
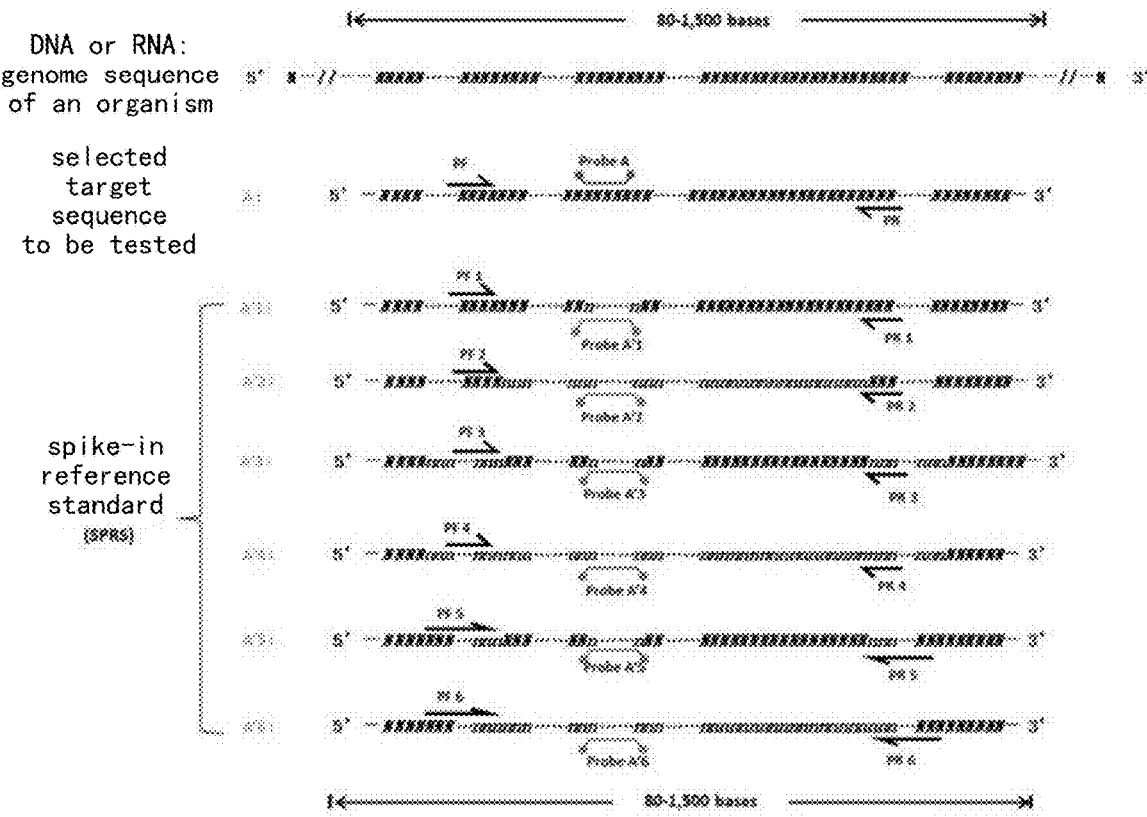
FIG. 28 shows a method for designing positive standards for all species of known DNA or RNA sequences that can be spiked into the test sample or sample collection device (tube), wherein, a: a concept scheme of the method for designing a positive standard; b: an example of "N" gene target inserted in SARS-CoV-2; c: an example of E6 gene target inserted into HPV; d: an example of ACE2 gene target inserted into human genome.

The standard N gene with a concentration of $2.4 \times 10^6$ in the stock solution was diluted by 6 gradients of 10-fold according to Table 48, and then subjected to a single-channel signal detection. The ROX channel was selected to detect the signal intensity of the standard N gene. The concentration gradient standard curve of the standard N gene was calculated by using the logarithm of copy number as an abscissa and the Ct value as an ordinate. The result was shown in FIG. 27 with the formula as y=−3.284x+38.363, wherein y represented the Ct value measured at a certain number of copies, and k was −3.284. Based on said formula, the logarithm of the corresponding copy number can be calculated so as to accurately quantify the virus copy number. $R^2$=0.9998 indicated that the results were credible.

3.2. Parameter Model Determination of Positive Standard and Quality Control that can be Spiked into the Test Sample The copy number of the standard N gene was kept unchanged, and the quality control RNA was detected in gradient by 3 primer pairs and 4 probes. 4-color channels were selected to determine the parameter model of positive standard and quality control that could be spiked in the test sample. The quantification accuracy of the quality control and standard was compared and the sensitivity of quality control was detected. The gradient detection of quality control was performed by selecting the copy number of standard N gene as 100 copies/rxn and 12.5 copies/rxn. The results were shown in Table 50 and Table 51.

TABLE 50 qPCR results 1 of parameter model of positive standard and
quality control that can be spiked into the test sample

| | | Quality Control Concentration copies/rxn | | | | | | |
|---|---|---|---|---|---|---|---|---|
| Detection target | Ct value | 1000 | 500 | 300 | 200 | 100 | 50 | 0 |
| FL-S-FAM | Quality Control RNA | 24.11 | 25.18 | 26.1 | 27.46 | 27.6 | 28.62 | NA |
| cCDC-N HEX | | 25.8 | 26.6 | 26.9 | 29.3 | 28.67 | 30.03 | NA |
| GAPDH2-CY5 | Human 293T RNA | 23.91 | 23.86 | 24.1 | 24.86 | 24.14 | 23.96 | 23.84 |
| N-AP593 | Standard N gene - 100 copies/rxn | 29.05 | 28.62 | 28.3 | 28.87 | 28.59 | 28.59 | 28.46 |

Note:
The detection concentration of the standard N gene was kept as 100copies/rxn; NA indicated that the Ct value was
not detected.

TABLE 51 qPCR results 2 of parameter model of positive standard and
quality control that can be spiked into the test sample

| | | Quality Control Concentration copies/rxn | | | | | |
|---|---|---|---|---|---|---|---|
| Detection target | Ct value | 100 | 50 | 25 | 12.5 | 2.5 | 0 |
| FL-S FAM | Quality Control RNA | 27.59 | 28.92 | 29.66 | 30.67 | 32.88 | NA |
| cCDC-N HEX | | 27.78 | 30.24 | 31.59 | 30.26 | 34.04 | NA |
| GAPDH-CY5 | 293T-RNA | 30.17 | 30.55 | 30.55 | 30.36 | 30.96 | 29.26 |
| FL-N AP593 | Standard N gene- 12.5 copies/rxn | 32.67 | 33.83 | 33.78 | 33.25 | 32.75 | 33.54 |

Note:
The detection concentration of the standard N gene was kept as 12.5copies/rxn; NA indicated that the Ct
value was not detected.

It was found that the average Ct value was 28.62 when the copy number of the standard N gene was 100 copies/rxn, which was close to the Ct value 28.67 of cCDC-N-HEX group when the copy number of quality control RNA was 100 copies, indicating that the quantification was accurate. The average Ct value was 33.3 when the copy number of the standard N gene was 12.5 copies/rxn, which was 2 Ct different from the Ct value of cCDC-N-HEX group when the copy number of quality control RNA was 100 copies. The above results show that the parameter model established in this method is accurate and can be used for the following applications: screening of SARS-cov-2 carrier; being an important basis for diagnosis of COVID-19 for individuals with elevated body temperature in hospital; screening of COVID-19 drugs, determination of treatment plans, and evaluation of efficacy; analysis of dynamic distribution of new coronavirus RNA load (2019-nCoV, Sars-cov-2 RNA Load) by using said model; as a reference for the guidance of drug use in late stage of COVID-19, and being one of the important indicators to identify whether patients with COVID-19 under treatment can be discharged from the hospital and enter a normal living community.

3.3. Experimental Data of SARS-Cov-2 Positive Samples:

The same reaction system as that in 3.2 was used, except that the quality control RNA was replaced with clinical samples for detection. The test results were shown in Table 52. The clinical samples were 5 positive and 5 negative samples tested with a kit approved by China. Among them, samples 1-5 were positive clinical samples, samples 6-10 were negative clinical samples, and sample 11 was a negative control. The results were shown in Table 52, wherein MixC #1 was a 50-molecule positive standard; MixC #3 was a 200-molecule positive standard. When selecting four-color channels to detect clinical samples, no signal was detected for the S target in all samples, that is, No Ct (N was equivalent to No Ct); CY5 and ROX could be detected in all samples, that is, human RNA and spiked-in standard RNA could be detected, indicating that the whole reaction was normal and the result was credible. The results obtained by the product of the present invention were positive for samples 1/2/3/4/5 and negative for samples 6/7/8/9/10, which were different from the results of approved kit, that is, the positive sample No. 2 was identified as a negative sample by the product of the present invention. Therefore, the product of the present invention can be used for detection in combination with products of other companies for comprehensive analysis to prevent virus carriers from entering the society

TABLE 52

Detection results of clinical samples

| | VIC | | CY5 | | RPOX | | |
|---|---|---|---|---|---|---|---|
| sample number | N target MixC#1 | MixC#3 | GAPDH target MixC#1 | MixC#3 | RNA-S target MixC#1 | MixC#3 | Reference Ct |
| 1 (positive) | 32.39 | 32.35 | 31.15 | 30.64 | 22.62 | 20.71 | 29.9 |
| 2 (positive) | | | | | | | |
| 3 (positive) | 30.79 | 31.32 | 28.44 | 28.37 | 22.55 | 20.73 | 29 |

TABLE 52-continued

| | | | | | | | |
|---|---|---|---|---|---|---|---|
| | | | Detection results of clinical samples | | | | |
| | VIC | | CY5 | | RPOX | | |
| sample number | N target MixC#1 | MixC#3 | GAPDH target MixC#1 | MixC#3 | RNA-S target MixC#1 | MixC#3 | Reference Ct |
| 4 (positive) | 33.58 | 34.7 | 30.59 | 30.07 | 22.84 | 20.92 | 32 |
| 5 (positive) | 33.77 | 35.73 | 31.92 | 31.24 | 22.81 | 20.82 | 32 |
| 6 (negative) | NoCt | NoCt | 27.95 | 28.05 | 24.95 | 23.15 | N |
| 7 (negative) | NoCt | NoCt | 30.52 | 30 | 22.85 | 20.89 | N |
| 8 (negative) | NoCt | NoCt | 29.83 | 29.5 | 22.79 | 20.81 | N |
| 9 (negative) | NoCt | NoCt | 28.54 | 28.16 | 22.8 | 20.71 | N |
| 10 (negative) | NoCt | NoCt | 29.25 | 28.54 | 22.77 | 20.77 | N |
| 11 (Negative Control) | NoCt | NoCt | 34.82 | 32.62 | 22.71 | 20.77 | N |

Note:
N target refers to the target to be detected as N; GAPDH target refers to an internal control; RNA-S target refers to a spike-in internal control.

Example 13: Determination of the Number of mRNA Molecules of SARS-Cov-2 Receptor ACE2 in Human 239 Cells 1. Experimental Steps DNA residues were detected by qPCR & RT-PCR, and RNA copy number concentration was detected by One-Step RT-ddPCR. The primers and probes related to plasmid construction and qPCR detection were shown in Table 53.

The preparation of mock virus with spike-in internal control (Example 2), RNA extraction (specific method i in Example 4) and ddPCR quantification method (method iv in Example 4) have been described in the above sections.

TABLE 53

Relevant primers and probes for plasmid construction and qPCR detection

| SEQ ID | Primer Name | Primer Sequence |
|---|---|---|
| 1 | ACE2-F1 | CAAGCTCTTCCTGGCTCCTTC (SEQ ID NO: 84) |
| 2 | ACE2-R1 | GGTCTTCGGCTTCGTGGTTA (SEQ ID NO: 85) |
| 3 | ACE2-HEX-P1 | 5'-HEX-AGCCTTGTTGCTGT AACTGCTGCTCAG-BHQ1-3' (SEQ ID NO: 86) |
| 4 | ACE2-F2 | CAAGCTCGTCCTCTCCTCGTT (SEQ ID NO: 87) |
| 5 | ACE2-R2 | GGTCTTCGGTCTGGTTTGAC (SEQ ID NO: 88) |
| 6 | ACE2-ROX-P2 | 5'-ROX-AATCTGTATGCTGA TGGTCGCTCTGCC-BHQ2-3' (SEQ ID NO: 89) |

The full-length sequence of quality control was shown in SEQ ID NO:50.

The sequence of standard (spike-in internal control) was shown in SEQ ID NO: 51.

2. Experimental Results

1) Spike-In Internal Control

RT-ddPCR quantification of RNA copy number concentration was performed according to SARS-cov-2 experimental method. The results showed that the copy number concentration of each aliquot of quality control RNA (detection probe ACE2-HEX) after mixing was about $2 \times 10^9$ Copies/$\mu$l, and the copy number concentration of the spike-in internal control RNA (detection probe ACE2-ROX) was about $1 \times 10^9$ Copies/$\mu$l.

According to obtained information, there is still no good method to measure the number of mRNA molecules of the gene to be detected in human cells. In the ORF stably transfected cell line of SARS-cov-2 receptor ACE2, the spike-in internal control we designed was used to determine the number of receptor ACE2 mRNA molecules.

Figure 29:
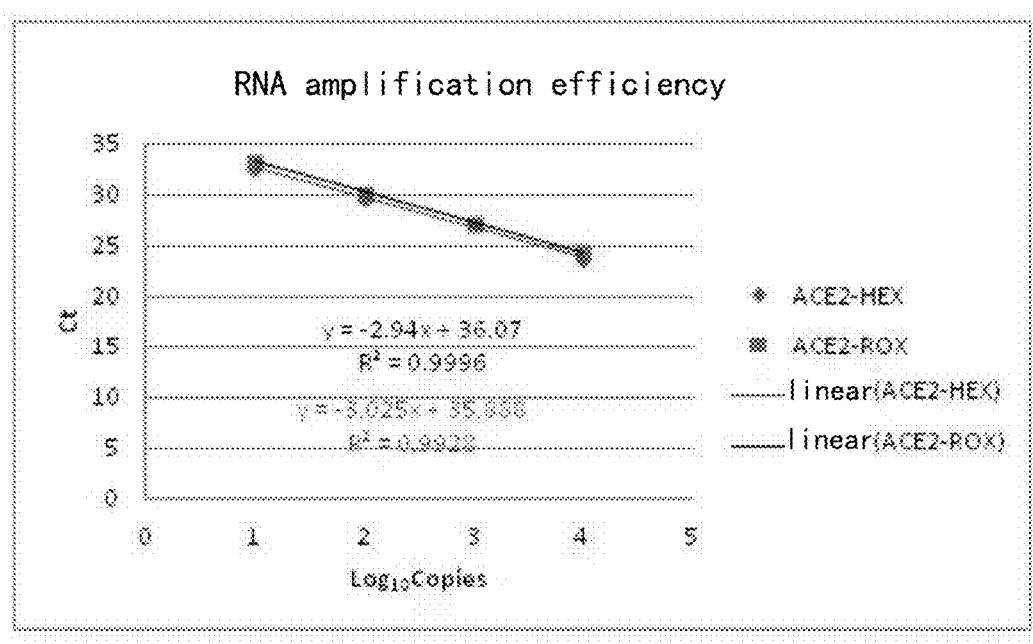
FIG. 29 shows the RNA amplification efficiency, wherein, the abscissa represents $Log_{10}Copies$, and the Copies are 10000, 1000, 100, and 10, and the ordinate represents Ct. Linear fitting is performed on the series of points, and the amplification efficiency E is calculated according to the slope k of the trend line: $E=(10^{(-1/k)}-1)\times100\%$.

2) Detection of Primer Amplification Efficiency for Standards and Quality Controls The concentration of quality control RNA and standard RNA prepared by in vitro transcription was diluted to 10000/1000/100/10/0 copies/rxn, and the amplification efficiencies of primers was tested to confirm that the amplification efficiency of standard primers and quality control primers were consistent. The results were shown in Table 54 and FIG. 29.

TABLE 54

Primer amplification efficiency

| RNA Copies | Log₁₀Copies | ACE2-HEX | ACE2-ROX |
|---|---|---|---|
| 10000 | 4 | 23.64 | 24.37 |
| 1000 | 3 | 27.11 | 27.20 |
| 100 | 2 | 29.69 | 30.11 |
| 10 | 1 | 32.50 | 33.20 |
| NTC | 0 | UTD | UTD |
| | R2 | 0.9928 | 0.9996 |
| | E | 1.14 | 1.19 |

4) SL 221-293T RNA and 293T RNA Quality Detection

The primers and probes in Table 53 were used to detect the quality of the extracted two types of cellular RNAs, and the results were shown in Table 55 and Table 56; with reference to the detection results of NanoDrop ND-1000 micro-ultraviolet spectrophotometer, the extracted RNA was of good quality and can be used for follow-up detection.

TABLE 55

SL 221-293T RNA quality detection

| SL221 RNA-pg/rxn | 5000.00 | | 1666.67 | |
|---|---|---|---|---|
| ACE2-HEX | 22.66 | 22.48 | 23.93 | 24.18 |
| GAPDH-CY5 | 26.20 | 26.19 | 27.60 | 27.90 |

TABLE 56

| 293T RNA quality detection | | | |
|---|---|---|---|
| 293T RNA-pg/rxn | 25.00 | | 12.5 |
| GAPDH-CY5 | 29.64 | 30.96 | 31.2 | 31.77 |

Example 14 Effect of Spike-in Standards on Quantification Results of Intracellular Target ACE2 mRNA 1. Experimental Materials
Reagents:
  5× Probes One-Step RT-qPCR Mix (GeneCopoeia)
  10×BlazeTaq™ RTase Mix (GeneCopoeia)
  Primer (ACE2-1, ACE2-2, GAPDH) (Golden Wisdom)
  Probe (ACE2-HEX, ACE2-ROX, GAPDH-CY5) (Shanghai Bailiger)
  SL 221-293T RNA/293T RNA (GeneCopoeia)
  Equipment: ABI ViiA 7 qPCR instrument
2. Experimental Steps
  1) According to the pre-experimental results of the quality control RNA, spike-in standard RNA and SL 221-293T RNA, and referring to the quantitation data of ddPCR, the quality control RNA, standard RNA and 293T RNA were subjected to a gradient dilution in a biological safety cabinet to obtain 2000/200/20/2 copies/μl of control RNA, 1000/100/50 copies/μl of standard RNA and 1000/333/111/37/12/4/1/0 pg/μl of SL 221-293T RNA/293T RNA.
  2) The RT-qPCR reaction system was prepared in a biological safety cabinet. The targets to be detected were ACE2-HEX and ACE2-ROX; the system was shown in Table 57. In the detection of quality control RNA and standard RNA, 293T RNA should be added to simulate cell detection; in the detection of intracellular ACE2 expression, 293T RNA was not added.

TABLE 57

| Triple RT-qPCR reaction system | |
|---|---|
| components | volume |
| 5 × One-Step RT-qPCR Mix for Probes | 5 μl |
| 10 × BlazeTaq RTase Mix | 2.5 μl |
| ACE2-Primer1 | 0.25 μl |
| ACE2-Primer2 | 0.25 μl |
| GAPDH-Primer | 0.25 μl |
| ACE2-HEX-Primer1 | 0.25 μl |
| ACE2-ROX | 0.25 μl |
| GAPDH-CY5 | 0.25 μl |
| 293T RNA | 1 μl |
| Standard RNA (1000/100/50 copies/μl) | 1 μl |
| Quality Control RNA/SL 293T RNA | 5 μl |
| ddH2O | 10 μl |
| Total | 25 μl |

Figure 30:
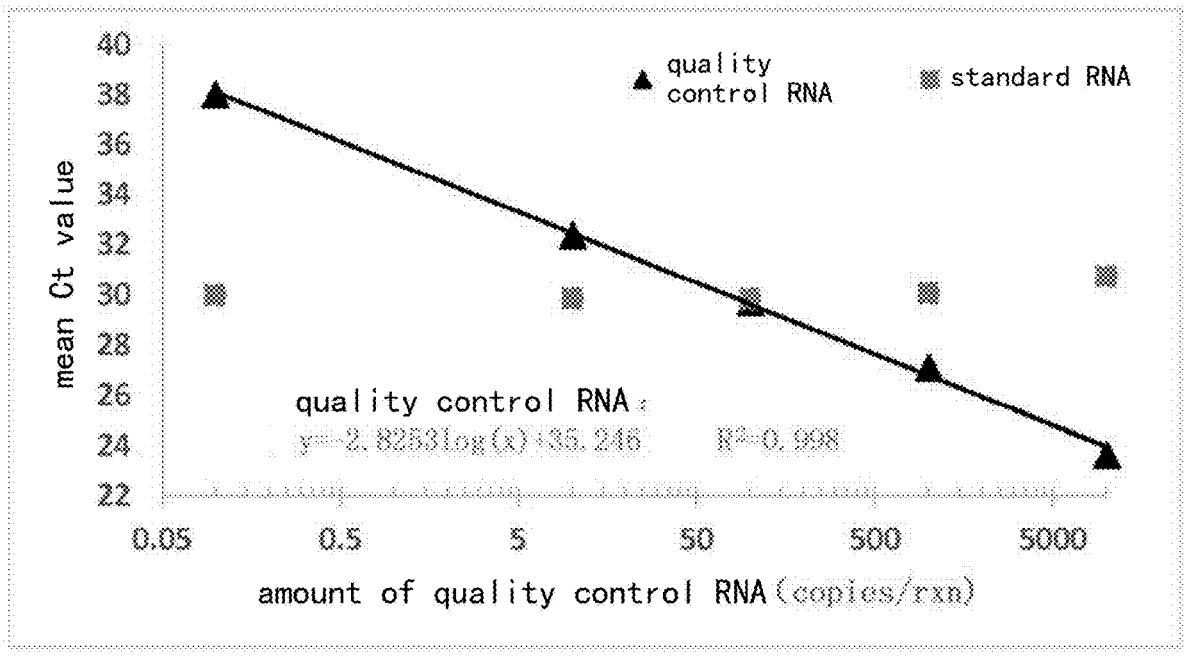
FIG. 30 is a graph of the quantitative standard curve of quality control RNA after the standard RNA is spiked in, wherein the abscissa represents the copy number concentration of the quality control RNA, and the ordinate represents the average Ct value.
Figure 31:
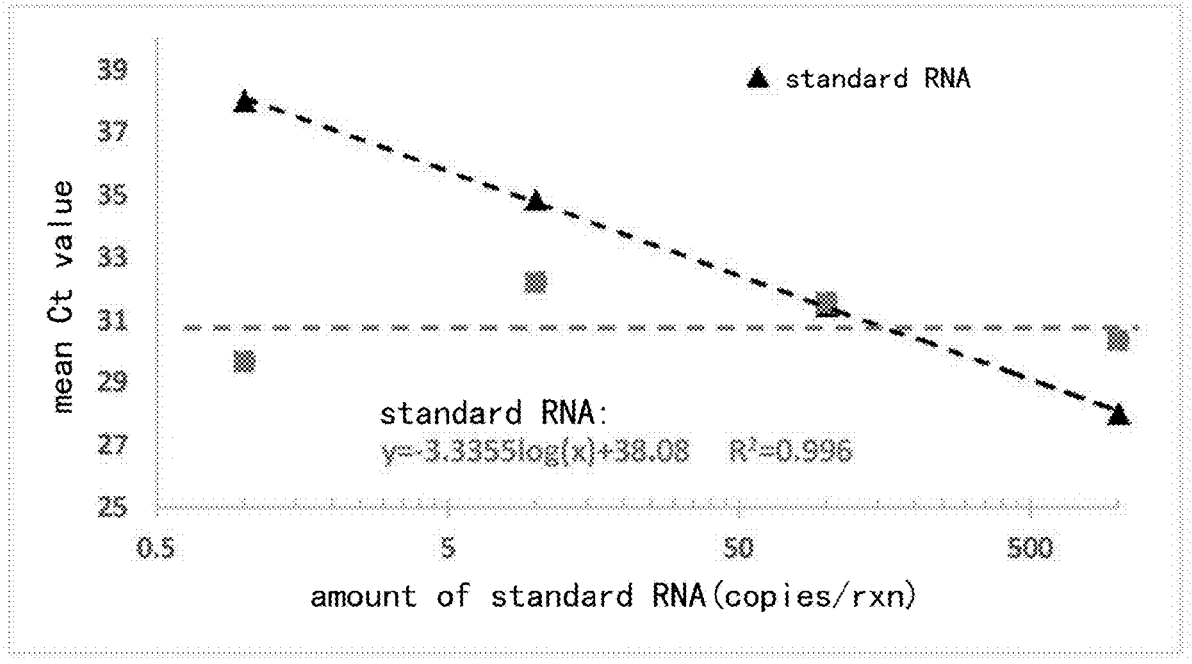
FIG. 31 is a standard curve graph of standard RNA quantification after the quality control RNA is spiked in, wherein the abscissa represents the copy number concentration of standard RNA, and the ordinate represents the average Ct value.

3) After the system was completely prepared, RT-PCR quantitative detection was performed on a qPCR instrument (ABI ViiA7).
3. Experimental Results
  1) Preparation of Standard Curve of Standards and Quality Controls
The standard curves of the standard and quality control were shown in FIG. 30 and FIG. 31.
The detection results were shown in Table 58 when the copy number of the standard spike-in internal control RNA was kept unchanged and the concentration of the quality control RNA was serially diluted. The detection results were shown in Table 59 when the copy number of the quality control RNA was kept unchanged and the concentration of the standard spike-in internal control RNA was serially diluted.

TABLE 58

Detection of quality control RNA with gradient concentration when the copy number of standard RNA being kept unchanged

| Quality Control | Standard RNA-100 copies/rxn | | |
|---|---|---|---|
| RNA-copies/rxn | ACE2-HEX | ACE2-ROX | GAPDH-CY5 |
| 10000 | 23.73 | 30.54 | 28.88 |
| | 23.55 | 30.89 | 28.44 |
| 1000 | 27.25 | 30.11 | 29.38 |
| | 26.97 | 30.00 | 29.35 |
| 100 | 29.62 | 29.86 | 27.82 |
| | 29.76 | 29.73 | 27.91 |
| 10 | 32.19 | 29.90 | 28.18 |
| | 32.54 | 29.75 | 28.20 |
| 0 | UTD | 29.95 | 28.01 |
| | UTD | 29.96 | 28.00 |
| NTC | UTD | UTD | UTD |
| | UTD | UTD | UTD |

TABLE 59

Detection of standard RNA with gradient concentration when the copy number of quality control RNA being kept unchanged

| Standard RNA- | Quality Control RNA-100 copies/rxn | | |
|---|---|---|---|
| copies/rxn | ACE2-ROX | ACE2-HEX | GAPDH-CY5 |
| 1000 | 28.16 | 30.51 | 30.70 |
| | 27.86 | 30.16 | 30.30 |
| 100 | 31.25 | 31.54 | 30.99 |
| | 31.66 | 31.55 | 30.10 |
| 10 | 35.01 | 32.29 | 30.62 |
| | 34.67 | 32.11 | 30.50 |
| 0 | UTD | 29.49 | 30.68 |
| | UTD | 29.80 | 30.70 |
| NTC | UTD | UTD | UTD |
| | UTD | UTD | UTD |

Analysis of the results: When the concentration of the quality control RNA was 100 copies/rxn, the Ct value of ACE2-HEX was not significantly different from that of ACE2-ROX when the concentration of the standard RNA was 50 copies/rxn, with a ΔCt value being 0.1, indicating that the quantification was accurate and the reaction system was good.

2) Detection of Intracellular ACE2 Expression

The expression of ACE2 was detected when the copy number of standard RNA was kept unchanged and the SL 221-293T RNA was diluted in gradient. The results were shown in Table 60.

TABLE 60

Detection of SL 221-293T RNA with gradient concentration when the copy number
of the standard spike-in internal control RNA being kept unchanged

| SL 221 | Standard RNA-ACE2-1000 copies/rxn | | | Standard RNA-ACE2-100 copies/rxn | | | Standard RNA-ACE2-50 copies/rxn | | |
|---|---|---|---|---|---|---|---|---|---|
| RNA-pg/rxn | ACE2-HEX | ACE2-ROX | GAPDH-CY5 | ACE2-HEX | ACE2-ROX | GAPDH-CY5 | ACE2-HEX | ACE2-ROX | GAPDH-CY5 |
| 5000 | 22.08 | 27.72 | 23.65 | 22.60 | 30.54 | 24.48 | 22.19 | 34.30 | 24.42 |
|  | 22.30 | 27.89 | 23.87 | 22.72 | 30.89 | 24.61 | 22.41 | 33.99 | 24.77 |
| 1666.67 | 23.89 | 27.72 | 23.48 | 24.40 | 30.11 | 27.58 | 23.58 | 32.14 | 24.66 |
|  | 24.15 | 28.16 | 25.67 | 24.32 | 30.00 | 26.14 | 23.68 | 32.53 | 25.81 |
| 555.56 | 25.71 | 27.89 | 26.71 | 25.81 | 29.86 | 27.06 | 25.33 | 31.23 | 27.29 |
|  | 25.60 | 27.97 | 26.47 | 25.75 | 29.73 | 26.21 | 25.21 | 31.35 | 27.02 |
| 185.19 | 27.95 | 28.34 | 28.04 | 27.49 | 29.90 | 29.08 | 27.59 | 31.27 | 30.93 |
|  | 27.37 | 28.17 | 28.76 | 27.36 | 29.75 | 28.85 | 27.02 | 31.42 | 28.92 |
| 61.73 | 28.96 | 28.08 | 29.85 | 28.99 | 29.93 | 29.65 | 28.71 | 31.17 | 30.20 |
|  | 28.76 | 27.95 | 31.10 | 28.61 | 29.58 | 31.39 | 28.57 | 31.13 | 30.64 |
| 20.58 | 30.88 | 28.11 | 33.09 | 30.69 | 30.10 | 32.50 | 30.21 | 31.42 | 32.81 |
|  | 30.81 | 28.14 | 31.93 | 31.05 | 29.95 | 34.17 | 30.41 | 31.43 | 32.67 |
| 6.86 | 32.44 | 28.08 | 34.25 | 32.48 | 29.96 | 33.83 | 32.45 | 31.57 | 34.46 |
|  | 32.28 | 28.37 | 33.59 | 31.56 | 29.76 | 34.23 | 31.89 | 31.56 | 34.16 |
| 0.00 | UTD | 28.05 | UTD | UTD | 30.12 | UTD | UTD | 31.36 | UTD |
|  | UTD | 28.23 | UTD | UTD | 30.21 | UTD | UTD | 31.59 | UTD |

Analysis of results: Referring to the detection result of the quality control RNA, the number of transcribed mRNA molecules of ACE2 in cells was 50 copies/10 pg RNA. The total RNA extracted from one cell was about 10 pg, that is, 10 pg/cell. Therefore, the expression of ACE2 in SL 221-293T cells was approximately 50±5 copies/cell.

The results showed that the spike-in internal control of the present invention could be used to accurately determine the copy number of organisms such as RNA virus (2019-nCoV) and the copy number of viral RNA molecules. It can also be widely used to evaluate the transcription levels and the number of related mRNA molecules for endogenous genes in biological cells, or exogenous genes integrated into genome by gene editing methods during physiological changes and changes in different regulatory factors, thus having extensive application value.

We claim:

1. A mock virus vector, wherein a viral backbone is used as the vector; the viral backbone contains one or more quantitative detection nucleic acid fragments and the coding gene of a fluorescent protein for tracking, the quantitative detection nucleic acid fragments has the same length as the nucleic acid target sequence of a test sample, and has the same percentage of base composition as the nucleic acid target sequence of the test sample; wherein the 5' end sequence A and 3' end sequence B of the quantitative detection nucleic acid fragment are the same as or different from the corresponding 5' end sequence A' and 3' end sequence B' of the nucleic acid target sequence of the test sample; the sequence A consists of a 5' end primer sequence for amplifying the nucleic acid target sequence of the test sample and two bases of the nucleic acid target sequence of the test sample directly downstream of the 5' end primer sequence; and the sequence B consists of a 3' end primer sequence for amplifying the nucleic acid target sequence of the test sample and two bases of the nucleic acid target sequence of test sample directly upstream of the 3' end primer sequence; the base sequence between the 5'end sequence A and 3' end sequence B of the quantitative detection nucleic acid fragment and the base sequence between the 5'end sequence A' and 3' end sequence B' of the nucleic acid target sequence of test sample are completely different.

2. The mock virus vector of claim 1, wherein the nucleic acid target sequence of test sample is derived from an organism, and the organism is selected from a virus, a bacterium, a fungus, a plant, an animal including a lower animal and a higher animal.

3. The mock virus vector of claim 2, wherein the virus is selected from the group consisting of DNA viruses and RNA viruses; the bacterium includes tuberculosis, gonorrhea, anthracnose, syphilis, plague, trachoma, etc., and the fungus is selected from the group consisting of mould, yeast, truffles and other mushrooms well-known to humans.

4. The mock virus vector of claim 3, wherein the length of the quantitative detection nucleic acid fragment is 80 bp-60 kb, 80 bp-19.5 kb, 80 bp-17.5 kb, 80 bp-1.5 kb, 80 bp-1 kb, 80 bp-500 bp, or 80 bp-200 bp, and the total length of the linker sequence between the quantitative detection nucleic acid fragments is not more than 8.5 kb, 8 kb or 7 kb.

5. The mock virus vector of claim 1, wherein, when the nucleic acid of test sample derives from SARS-COV-2, the nucleic acid target sequence of test sample is at least two coding genes selected from the following coding genes group consisting of: full length Orf1ab coding gene or fragment thereof, full length S protein coding gene or fragment thereof, full length E protein coding gene or fragment thereof, and full length N protein coding gene or fragment thereof.

6. The mock virus vector of claim 5, wherein the quantitative detection nucleic acid fragment is one or more nucleic acid sequences selected from the group consisting of:

a detection target sequence 1 comprising or at least consisting of sequences selected from SEQ ID NO: 1 to SEQ ID NO: 2 or a combination thereof;

a detection target sequence 2 comprising or at least consisting of SEQ ID NO: 3;

a detection target sequence 3 comprising or at least consisting of SEQ ID NO: 4; and a detection target sequence 4 comprising or at least consisting of sequences selected from SEQ ID NO: 5 to SEQ ID NO: 8 or any combination thereof.

7. The mock virus vector of claim 6, wherein the sequence of the mock virus is shown in SEQ ID NO: 9.

8. A mock virus particle prepared by the mock virus vector of claim 1.

9. Use of the mock virus vector of claim 1 in the following:

(1) qualitative and quantitative detection of nucleic acid targets in samples; or (2) an application for preparing reagents or kits in detecting the nucleic acid target in the sample; or (3) an application for evaluating a therapeutic effect on a patient carrying the nucleic acid target; or (4) an application for evaluating or screening a drug for the treatment of a disease caused by the organism.

10. A qualitative and quantitative reference standard RNA prepared by extracting the mock virus particle of claim 8, wherein the organism is an RNA virus.

11. The qualitative and quantitative reference standard RNA of claim 10, which is used as a reference standard in the process of reverse transcription from RNA to cDNA involved in the detection of RNA viruses.

12. A qualitative and quantitative reference standard, wherein the quantitative reference standard DNA is prepared by extracting the DNA of the mock virus particle of claim 8, wherein the genetic material of the organism is DNA.

13. The qualitative and quantitative reference standard DNA of claim 12, which is used for quality analysis and quality control of amplification efficiency and fluorescence signal in an DNA amplification process involved in a process of detecting an RNA virus or a process of detecting an organism of which the genetic material is DNA.

14. The mock virus vector of claim 1, wherein the viral backbone is a lentiviral backbone or adenoviral backbone.

15. The mock virus vector of claim 14, wherein the lentiviral backbone is selected from the group consisting of a lentivirus vector and an FIV virus vector.

16. The mock virus vector of claim 15, wherein the lentiviral vector includes second-generation or third-generation lentiviral vectors.

17. The mock virus vector of claim 1, wherein, for the base sequence between the 5'end sequence A and 3' end sequence B of the quantitative detection nucleic acid fragment and the base sequence between the 5'end sequence A' and 3' end sequence B' of the nucleic acid target sequence of test sample, there is no subsequence having more than 3 contiguous identical bases between the two base sequences after alignment.

18. The mock virus vector of claim 1, wherein the one or more quantitative detection nucleic acid fragments and the fluorescent proteins are connected by means of linkers, and the length of the linkers is 6-800 bp, 20-800 bp or 6-200 bp.

19. The mock virus vector of claim 18, wherein the linkers contain transcriptional control elements.

20. The mock virus vector of claim 3, wherein the virus is a coronavirus selected from the group consisting of SARS virus, MERS virus, and SARS-COV-2 virus.

*    *    *    *    *